(12) United States Patent
Hoffman et al.

(10) Patent No.: US 10,682,517 B2
(45) Date of Patent: Jun. 16, 2020

(54) SYSTEMS, APPARATUS, METHODS AND COMPUTER-READABLE STORAGE MEDIA FACILITATING AUTHORIZED TELEMETRY WITH AN IMPLANTABLE DEVICE

(71) Applicant: Medtronic, Inc., Minneapolis, MN (US)

(72) Inventors: Matthew J. Hoffman, St. Paul, MN (US); Nicholas C. Wine, Minneapolis, MN (US); Bo Zhang, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/149,409

(22) Filed: Oct. 2, 2018

(65) Prior Publication Data

US 2019/0030349 A1 Jan. 31, 2019

Related U.S. Application Data

(62) Division of application No. 14/941,059, filed on Nov. 13, 2015, now Pat. No. 10,086,208.

(Continued)

(51) Int. Cl.
*A61N 1/372* (2006.01)
*A61B 5/00* (2006.01)
*A61B 5/0205* (2006.01)
*A61N 1/362* (2006.01)
*A61B 5/0432* (2006.01)
*A61B 5/1455* (2006.01)

(52) U.S. Cl.
CPC ........ *A61N 1/37252* (2013.01); *A61B 5/0031* (2013.01); *A61B 5/0205* (2013.01); *A61N 1/37247* (2013.01); *A61B 5/0006* (2013.01); *A61B 5/0432* (2013.01); *A61B 5/14551* (2013.01); *A61B 5/7285* (2013.01); *A61N 1/362* (2013.01)

(58) Field of Classification Search
CPC .................. A61N 1/37252; A61N 1/37247
USPC ............................................. 607/60
See application file for complete search history.

(56) References Cited

U.S. PATENT DOCUMENTS 7,174,130 B2  2/2007 Kurisko
8,395,498 B2  3/2013 Gaskill
(Continued)

FOREIGN PATENT DOCUMENTS

WO    WO11157538 A1    12/2011

*Primary Examiner* — Nadia A Mahmood

(57) ABSTRACT

Techniques for facilitating authorized telemetry with an implantable device are provided. In one embodiment, for example, a method includes comparing, by a first device having a processor, first electronic information with second electronic information. The first electronic information is indicative of a first motion of a second device external to a body in which the implantable device is located, and the second electronic information is indicative of a second motion of the implantable device. The method also includes determining whether a defined level of correlation exists between the first electronic information and the second electronic information, and initiating a telemetry session between the second device and the implantable device based on a determination that the defined level of correlation exists between the first electronic information and the second electronic information.

17 Claims, 24 Drawing Sheets

Related U.S. Application Data

(60) Provisional application No. 62/126,238, filed on Feb. 27, 2015.

(56) References Cited

U.S. PATENT DOCUMENTS

| | | |
|---|---|---|
| 8,649,757 B2 | 2/2014 | Roberts |
| 8,750,799 B2 | 6/2014 | Giles |
| 8,868,794 B2 | 10/2014 | Masoud |
| 9,687,658 B2 | 6/2017 | Wu |
| 9,855,433 B2 | 1/2018 | Shahandeh |
| 2008/0119705 A1 | 5/2008 | Patel |
| 2009/0048644 A1 | 2/2009 | Stahmann |
| 2009/0270949 A1 | 10/2009 | Kalpin |
| 2010/0167646 A1 | 7/2010 | Alameh |
| 2010/0292556 A1 | 11/2010 | Golden |
| 2011/0171905 A1 | 7/2011 | Roberts |
| 2012/0108922 A1 | 5/2012 | Schell |
| 2012/0163663 A1 | 6/2012 | Masoud |
| 2012/0165619 A1 | 6/2012 | Masoud |
| 2012/0172690 A1 | 7/2012 | Anderson |
| 2012/0172941 A1 | 7/2012 | Rys |
| 2013/0110008 A1* | 5/2013 | Bourget ............... A61B 5/11 600/595 |
| 2013/0132855 A1 | 5/2013 | Manicka |
| 2014/0185805 A1 | 7/2014 | Andersen |
| 2014/0214104 A1 | 7/2014 | Greenhut |
| 2014/0330327 A1 | 11/2014 | Thompson-Nauman |
| 2014/0365654 A1 | 12/2014 | Huerto |
| 2015/0133951 A1 | 5/2015 | Seifert |
| 2015/0341785 A1 | 11/2015 | Young |

\* cited by examiner

SYSTEMS, APPARATUS, METHODS AND COMPUTER-READABLE STORAGE MEDIA FACILITATING AUTHORIZED TELEMETRY WITH AN IMPLANTABLE DEVICE

CROSS-REFERENCE TO RELATED APPLICATIONS

This application is a Division of U.S. patent application Ser. No. 14/941,059, filed Nov. 13, 2015, entitled. "SYSTEMS. APPARATUS, METHODS AND COMPUTER-READABLE STORAGE MEDIA FACILITATING AUTHORIZED TELEMETRY WITH AN IMPLANTABLE DEVICE", which claims the benefit of the filing date of U.S. Provisional Application Ser. No. 62/126,238, filed Feb. 27, 2015, and entitled, "SYSTEMS, APPARATUS. METHODS AND COMPUTER-READABLE STORAGE MEDIA FACILITATING AUTHORIZED TELEMETRY WITH AN IMPLANTABLE DEVICE," the content of both of which is incorporated by reference in their entirety.

TECHNICAL FIELD

This disclosure relates generally to implantable devices and, more particularly, to systems, apparatus, methods and computer-readable storage media facilitating authorized telemetry with an implantable device.

BACKGROUND

Contemporary healthcare relies heavily on implantable medical devices (IMDs) to help patients lead normal and healthy lives. For example, IMDs such as pacemakers, implantable cardioverter-defibrillators (ICDs), cardiac resynchronization therapy (CRT) devices, drug delivery systems, and neurostimulators can help manage a broad range of ailments, such as cardiac arrhythmia, diabetes, and Parkinson's disease. Modern IMDs are entrusted with vital tasks in terms of medical care; delivering insulin or painkillers at proper rates, measuring and collecting data on the vital signs and passing the data on to doctors and nurses, and direct stimulation of a critical function of an organ, as is the case with pacemakers, ICDs, CRTs, and neurostimulators.

There is a business desire to use commercially available telemetry protocols to more easily facilitate widespread provisioning of telemetry solutions. When enabling telemetry with an IMD using commercially available telemetry protocols, security is of the utmost importance to maintain a patient's privacy and to prevent any unauthorized or inadvertent programming of the IMD. Accordingly, there is a desire for one or more approaches of restricting and/or policing telemetry communication with an IMD.

SUMMARY

The following presents a simplified summary to provide a basic understanding of one or more embodiments described herein. This summary is not an extensive overview of the embodiments envisaged herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description may include additional or alternative embodiments beyond those described in the Summary section.

Embodiments described herein include systems, apparatus, methods and computer-readable storage media facilitating authorized telemetry with an implantable device. In some embodiments, the implantable device is or includes an IMD. In other embodiments, the implantable device is or includes a device configured to interact with the IMD. In these embodiments, both the implantable device and the IMD can be implanted within a patient.

In an embodiment, a method is provided that includes comparing, by a first device including a processor, first electronic information with second electronic information. The first electronic information is indicative of a first image associated with a second device external to a body in which an implantable device is located, and the second electronic information is indicative of a second image associated with the implantable device. The method further includes determining whether a defined level of correlation exists between the first electronic information and the second electronic information, and initiating a telemetry session between the second device and the implantable device based on a determination that the defined level of correlation exists between the first electronic information and the second electronic information. For example, in some embodiments, the first image and the second image are indicative of one or more electronic images of a patient having the body in which the implantable device is located. The second device can include a camera, and the method can also include receiving, by the first device, the first electronic information from the second device, wherein the first electronic information is generated by the camera of the second device.

In another embodiment, a method is provided that includes comparing, by a first device including a processor, first electronic information with second electronic information. The first electronic information is indicative of a first motion of a second device external to a body in which an implantable device is located, and the second electronic information is indicative of a second motion of the implantable device. The method further includes determining whether a defined level of correlation exists between the first electronic information and the second electronic information, and initiating a telemetry session between the second device and the implantable device based on a determination that the defined level of correlation exists between the first electronic information and the second electronic information. For example, the first motion is associated with first acceleration of the second device and the second motion is associated with second acceleration of the implantable device. In some embodiments, the first motion is associated with a first time period, the second motion is associated with a second time period, and the first time period and the second time period are concurrent.

In another embodiment, a method is provided that includes comparing, by a first device including a processor, first electronic information with second electronic information. The first electronic information is indicative of a speech signal recorded by a second device external to a body in which an implantable device is located, and the second electronic information is indicative of vibration information internal to the body and detected by the implantable device. The method further includes determining whether a defined level of correlation exists between the first electronic information and the second electronic information, and initiating a telemetry session between the second device and the implantable device based on a determination that the defined level of correlation exists between the first electronic information and the second electronic information. In some embodiments, recordation by the second device is performed by a microphone of the second device. The vibration information can be detected by an accelerometer of the implantable device.

In another embodiment, a method is provided that includes comparing, by a first device including a processor, first electronic information received at a second device external to a body in which an implantable device is located with second electronic information associated with the implantable device. The first electronic information and the second electronic information include one or more passwords and the first electronic information is received via a user interface to the second device. The method further includes determining whether the first electronic information and the second electronic information match, and initiating a telemetry session between the second device and the implantable device based on a determination that the first electronic information and the second electronic information match.

In one or more additional embodiments, a computer-readable storage medium is provided. The computer-readable storage medium stores executable instructions that, in response to execution, cause a first device including a processor to perform operations. These operations include comparing first electronic information with second electronic information, wherein the first electronic information is indicative of a speech signal recorded by a second device external to a body in which an implantable device is located, and wherein the second electronic information is indicative of vibration information internal to the body and detected by the implantable device. The operations further include determining whether a defined level of correlation exists between the first electronic information and the second electronic information, and initiating a telemetry session between the second device and the implantable device based on a determination that the defined level of correlation exists between the first electronic information and the second electronic information.

In one or more additional embodiments, a system is provided that includes an implantable device having a processor, and a first device configured to compare first electronic information received at a second device external to a body in which the implantable device is located with second electronic information associated with the implantable device. The first electronic information and the second electronic information include one or more types of secure information. The first electronic information is received via a user interface to the second device. The first device is further configured to: determine whether the first electronic information and the second electronic information have a defined level of similarity, and initiate a telemetry session between the second device and the implantable device based on a determination that the first electronic information and the second electronic information have the defined level of similarity.

In an additional embodiment, an apparatus is provided that includes a comparison device configured to compare first electronic information received at a device external to a body in which an implantable device is located with second electronic information associated with the implantable device. The first electronic information and the second electronic information include one or more types of secure information, and the first electronic information is received via a user interface to the device. The comparison device is further configured to determine whether the first electronic information and the second electronic information have a defined level of correlation. The apparatus further includes a communication device configured to initiate a telemetry session between the device and the implantable device based on a determination that the first electronic information and the second electronic information have the defined level of correlation.

In yet another embodiment, an apparatus is provided that includes a comparison device configured to compare first electronic information received at a device external to a body in which an implantable device is located with second electronic information associated with the implantable device. The first electronic information and the second electronic information include one or more types of secure information, and the first electronic information is received via a user interface to the device. The comparison device is further configured to determine whether the first electronic information and the second electronic information have a defined level of correlation. The apparatus further includes a communication device configured to initiate a telemetry session between the implantable device and a first device based on a determination that the first electronic information and the second electronic information have the defined level of correlation. The first device is distinct from the device.

In another embodiment, another computer-readable storage medium is provided. The computer-readable storage medium stores executable instructions that, in response to execution, cause a first device including a processor to perform operations. The operations include comparing first electronic information with second electronic information, wherein the first electronic information is indicative of morphology of a first aspect of a photoplethysmogram (PPG) for a body in which an implantable device is located, and wherein the second electronic information is indicative of a second aspect of the body and detected by the implantable device. The operations also include: determining whether a defined level of correlation exists between the first electronic information and the second electronic information; and initiating a telemetry session between a second device and the implantable device based on a determination that the defined level of correlation exists between the first electronic information and the second electronic information.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification may be employed. Other advantages and novel features of the specification will become apparent from the following detailed description of the specification when considered in conjunction with the drawings.

DETAILED DESCRIPTION

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

Further, while embodiments described herein variously reference an implantable device or an IMD as implanted or located within a patient or a body or worn by a patient or a body, it is noted and should be understood that in any of these embodiments, the implantable device or the IMD referenced can be implanted or located within the patient or body and/or coupled to or disposed on an exterior surface of the patient or body as appropriate relative to the specific embodiments. All such variations are envisaged and intended to be encompassed herein.

Figure 1:
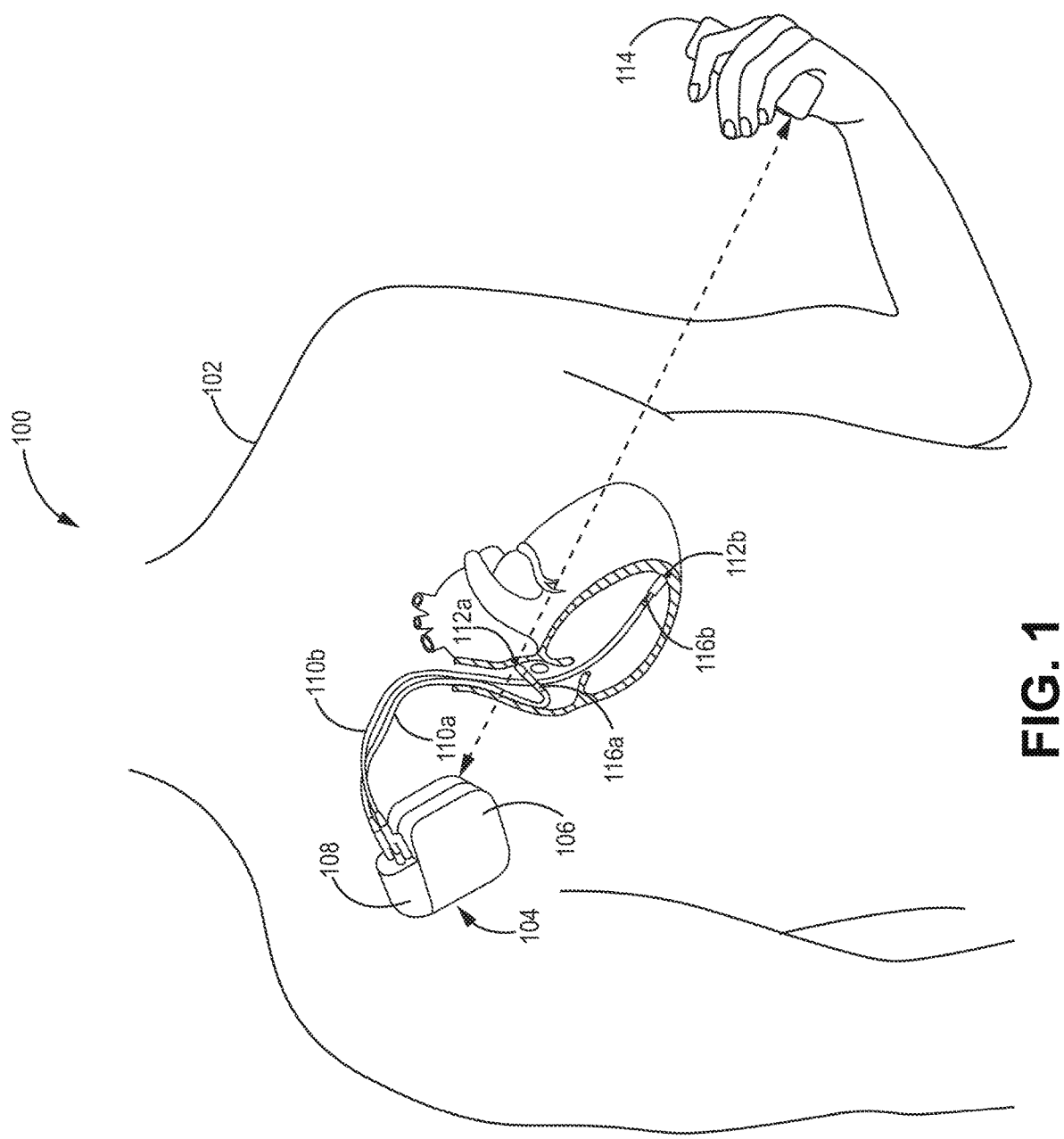
FIG. 1 illustrates a schematic diagram of an example, non-limiting medical device telemetry system facilitating authorized telemetry with an implantable device in accordance with one or more embodiments described herein.

With reference now to the drawings, FIG. 1 illustrates a schematic diagram of an exemplary, non-limiting medical device telemetry system 100 facilitating authorized telemetry between an implantable device and an external device in accordance with one or more embodiments described herein. Embodiments of components, devices, apparatus and/or systems herein can include one or more machine-executable components embodied within one or more machines (e.g., embodied in one or more computer-readable storage media associated with one or more machines), circuitry, hardware (e.g., accelerometers) or a combination of one or more of machine-executable components, circuitry and/or hardware. In some embodiments, the machine-executable components (e.g., processors, computers, computing devices or virtual machines), circuitry and/or hardware can cause or enable the components, devices, apparatus and/or systems to perform one or more operations described herein.

In the embodiment shown, system 100 includes an implantable device 104 implanted within a body 102, and an external device 114. In various embodiments, the implantable device 104 can include any number of different types of implantable devices. The particular, size, shape, placement and/or function of the implantable device 104 may not be critical to the subject disclosure in some embodiments. In one or more embodiments, the implantable device 104 is or includes an IMD. For example, IMDs can include, but are not limited to, cardiac pacemakers, cardiac defibrillators, cardiac re-synchronization devices, cardiac monitoring devices, cardiac pressure monitoring devices, cardiac loop recorders, spinal stimulation devices, neural stimulation devices, gastric stimulation devices, diabetes pumps and/or drug delivery devices. In various embodiments, however, the implantable device 104 can be or include any number of other types of implantable devices that are not IMDs.

For exemplary purposes, implantable device 104 is illustrated in system 100 as an IMD implanted within the chest of a patient and configured to provide medical treatment associated with a heart disease or condition (e.g., an ICD and/or a pacemaker). For example, implantable device 104 can embody a cardiac stimulation device configured to deliver therapy in the form of electrical pulses to cardiac tissue. The implantable device 104 includes a housing 106 within which electrical components and a power source are housed. These electrical components can vary depending on the particular features and functionality of the implantable device 104. In various embodiments, these electrical components can include, but are not limited to, one or more processors, memories, transmitters, receivers, transceivers, sensors, sensing circuitry, therapy circuitry, antennas and/or other components. Housing 106 can be formed from conductive materials, non-conductive materials or a combination thereof.

The implantable device 104 further includes leads 110a,b connected to the housing 106. The leads 110a,b extend into the heart and respectively include one or more electrodes. For example, as depicted in system 100, leads 110a,b each include respective tip electrodes 112a,b and ring electrodes 116a,b located near a distal end of their respective leads 110a,b. When implanted, tip electrodes 112a,b and/or ring electrodes 116a,b are placed relative to or in a selected tissue, muscle, nerve or other location on or within the body 102 of the patient. As depicted in system 100, tip electrodes 112a,b are extendable helically shaped electrodes to facilitate fixation of the distal end of leads 110a,b to the target location on or within the body 102 of the patient. In this manner, tip electrodes 112a,b can be formed to define a fixation mechanism. In other embodiments, one or both of tip electrodes 112a,b may be formed to define fixation mechanisms of other structures. In other instances, leads 110a,b may include a fixation mechanism separate from tip electrodes 112a,b. Fixation mechanisms can be any appropriate type, including, but not limited to, a grapple mechanism, a helical or screw mechanism, a drug-coated connection mechanism in which one or more drugs serves to reduce infection and/or swelling of the tissue and/or another attachment mechanism.

Leads 110a,b are connected at a proximal end of the implantable device 104 via connector block 108. Connector block 108 may include one or more receptacles that interconnect with one or more connector terminals located on the proximal end of leads 110a,b. Leads 110a b are ultimately electrically connected to one or more of the electrical components within housing 106. One or more conductors (not shown) extend within leads 110a,b from connector block 108 along the length of the leads 110a,b to engage the ring electrodes 116a,b and tip electrodes 112a,b, respectively. In this manner, each of tip electrodes 112a,b and ring electrodes 116a,b is electrically coupled to a respective conductor within its associated lead bodies. For example, a first electrical conductor can extend along the length of the body of lead 110a from connector block 108 and electrically couple to tip electrode 112a and a second electrical conductor can extend along the length of the body of lead 110b from connector block 108 and electrically couple to ring electrodes 116b. The respective conductors may electrically couple to circuitry, such as a therapy module or a sensing module, of the implantable device 104 via connections in connector block 108.

In one or more embodiments, the implantable device 104 is configured to deliver therapy to the heart (or other location) via the electrical conductors to one or more of tip electrodes 112a,b and ring electrodes 116a,b. In the case of pacing therapy, for example, the implantable device 104 may deliver pacing pulses via a unipolar electrode configuration, e.g., using tip electrodes 112a,b and a housing electrode of the implantable device 104. In other instances, the implantable device 104 may deliver pacing pulses via a bipolar electrode configuration, e.g., using tip electrodes 112a,b and ring electrodes 116a,b. Implantable device 104 may also receive sensed electrical signals on the electrical conductors from one or more of tip electrodes 112a,b and ring electrodes 116a,b. The implantable device 104 may sense the electrical signals using either a unipolar or bipolar electrode configuration.

The configuration, features and functionality of implantable device 104 are merely provided as an example. In other examples, the implantable device 104 can include more or fewer leads extending from the housing 106. For example, the implantable device 104 can be coupled to three leads. For example, the implantable device 104 can be coupled to a third lead implanted within a left ventricle of the heart of the patient. In another example, the implantable device 104 can be coupled to a single lead that is implanted within a chamber, e.g., an atrium or ventricle of the heart of the patient. In other embodiments, however, the implantable device 104 can be attached to the outside of the heart. In other embodiments, the lead may be an extravascular lead with the electrodes implanted subcutaneously above the ribcage/sternum or underneath or below the sternum. Example extravascular ICDs having subcutaneous electrodes are described in U.S. Patent Publication No. 2014/0214104 (Greenhut et al.) and U.S. Patent Publication No. 2015/0133951 (Seifert et al.), each of which is incorporated herein in its entirety. One example extravascular ICD having substernal electrodes is described in U.S. Patent Publication No. 2014/0330327 (Thompson-Nauman et al.). In some embodiments, the implantable device 104 can include other leads (e.g., atrial lead and/or left ventricular lead). As such, implantable device 104 can be used for single chamber or multi-chamber cardiac rhythm management therapy. In addition to more or fewer leads, each of the leads may include more or fewer electrodes. In instances in which the implantable device 104 is used for therapy other than pacing (e.g., defibrillation or cardioversion), the leads can include elongated electrodes, which may, in some instances, take the form of a coil. The implantable device 104 can deliver defibrillation or cardioversion shocks to the heart via any combination of the elongated electrodes and housing electrode. As another example, the implantable device 104 can include leads with a plurality of ring electrodes (e.g., as used in some implantable neurostimulators), without a tip electrode or with one of the ring electrodes functioning as the tip electrode.

In another embodiment, the implantable device 104 may include no leads, as in the case of an intracardiac pacemaker or a leadless pressure sensor. In the case of an intracardiac pacemaker, the implantable device 104 may include a housing sized to fit wholly within the patient's heart. In one example, the housing may have a volume that is less than 1.5 cubic centimeters (cc) and, in some embodiments, less than 1.0 cc. However, the housing may be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly-assigned U.S. Patent Publication No. 2012/0172690 (Anderson et al.), U.S. Patent Publication No. 2012/0172941 (Kenneth), and U.S. Patent Publication No. 2014/0214104 (Greenhut et al.), each of which is incorporated herein in its entirety. In the case of a leadless pressure sensor, the implantable device 104 may include a housing having a fixation member and a pressure sensing component. One example of a leadless pressure sensor is described in U.S. Patent Publication No. 2012/0108922 (Schell et al.), which is incorporated herein in its entirety.

Implantable device 104 can include various different types of sensors, electrodes and/or circuitry configured to detect one or more signals associated with a physiological state within the body 102 of the patient, motion of the body 102 of the patient, or sound or speech generated or detected within the body 102 of the patient. In some embodiments, the physiological state can include a function of the body 102 and/or a condition of the body 102. These sensors, electrodes and/or circuitry can include, but are not limited to, sensors, electrodes and/or circuitry configured to detect blood pressure, blood flow rate, heart rate, respiratory rate, blood composition, substances within the blood (e.g., oxygen, carbon dioxide or glucose), temperature, patient activity state (e.g., moving, still, asleep, awake or exercising), speech and/or other physical properties associated with the patient. As implantable device 104 is illustrated in system 100, by way of example, these sensors and/or circuitry can be included within the housing 106 and/or included on or in association with the various leads 110*a,b*, tip electrodes 112*a,b* and ring electrodes 116*a,b* of the implantable device 104. For example, in addition to tip electrodes 112*a,b* and ring electrodes 116*a,b*, implantable device 104 can include one or more additional sensors (not shown) that include, but are not limited to, pressure sensors, blood flow sensors, force sensors, blood composition sensors, optical sensors, accelerometers, piezoelectric sensors, biosensors, acoustic sensors and/or other sensors configured to detect states and/or physical activity of the body 102.

Aspects of the systems, apparatuses or processes explained in this disclosure can constitute machine-executable component(s) embodied within machine(s), e.g., embodied in one or more computer-readable storage mediums (or media) associated with one or more machines. Such component(s), when executed by the one or more machines, e.g., computer(s), computing device(s), virtual machine(s), etc. can cause the machine(s) to perform the operations described. Implantable device 104 can include memory (not shown) for storing computer-executable components and instructions. Implantable device 104 can further include a processor (not shown) to facilitate operation of the instructions (e.g., computer-executable components and instructions) by implantable device 104.

In one or more embodiments described herein, when authorized, an external device 114 can communicate with the implantable device 104 to exchange data with the implantable device 104. For example, the external device 114 can read data captured by the implantable device 104 (e.g., electrocardiogram (ECG) data) and/or remotely control the implantable device 104 (e.g., to adjust sensing, pacing therapy and/or defibrillation therapy). In one example, the external device 114 can remotely control the implantable device 104 by programming the implantable device 104. The implantable device 104 may also transmit to external device 114 sensed physiological data, diagnostic determinations made based on the sensed physiological data, implantable device 104 performance data and/or implantable device 104 integrity data.

External device 114 can include any suitable computing device configured to communicate with implantable device 104. For example, external device 114 can include, but is not limited to, a handheld computing device, a wearable computing device, a mobile phone, a smart phone, a tablet personal computer (PC), a personal digital assistant (PDA), a laptop computer, and/or a desktop.

Implantable device 104 and external device 114 can employ various wireless communication protocols to communicate with one another in association with an authorized telemetry session. For example, external device 114 and implantable device 104 can communicate using near field communication (NFC). In another example, external device 114 and implantable device 104 can communicate using any of various types of wireless communication protocols. For example, other communication protocols that can be employed by external device 114 and implantable device 104 to perform telemetry can include, but are not limited to, a BLUETOOTH® technology-based protocol (e.g., BLUETOOTH® low energy (BTLE) protocol), an ultra-wideband (UWB) technology-based protocol, a radio frequency (RF) communication-based protocol, or any other proprietary or non-proprietary communication protocols.

In various embodiments, communication can be facilitated over a personal area network (PAN) or a local area network (LAN) (e.g., a Wireless Fidelity (Wi-Fi) network) that can provide for communication over greater distances than the NFC protocol or provide other advantages (e.g., stronger encryption protocols). In some embodiments, the external device 114 and the implantable device 104 can communicate with one another and/or another device (e.g., a server device or a second external device) over a wide area network (WAN) using cellular or Hyper Text Transfer Protocol (HTTP)-based communication protocols (e.g., session initiation protocol (SIP)).

A first group of embodiments of system 100 is described in connection with authorizing telemetry between the implantable device 104 and the external device 114 based on information that is concurrently detected by the implantable device 104 and the external device 114. In some embodiments, detection by the implantable device 104 and the external device 114 can include, but is not limited to, sensing and/or measuring information or signals by the implantable device 104 and the external device 114. In some embodiments, the detection can be performed when the implantable device 104 and the external device 114 are located within relatively close proximity of one another although such is not required in every embodiment envisaged herein.

The term "concurrently" is used herein to refer to an overlapping time period. In various embodiments, the overlapping time periods can start and stop at different points in time while having at least a portion of time that is overlapping. In some embodiments, the duration of the time periods during which the detecting is performed can vary depending on the type of signal that is being detected by the implantable device 104 and/or the external device 114. In various embodiments, the signal can be detected by any number of different approaches including, but not limited to, sensing, measuring or the like. In some embodiments, when the implantable device 104 and the external device 114 are configured to detect information associated with a distinct sound or speech generated by the body 102 in which the implantable device 104 is implanted, the duration of the time period during which the implantable device 104 and/or the external device 114 performs detection can be determined by the duration of the distinct sound or speech.

A sensor or detection device as described herein can include hardware (e.g., sensor hardware components, sensor circuitry or a processor), software (e.g., computer-executable instructions configured to facilitate processing of sensed data), or a combination of hardware and software configured to detect (e.g., by sensing, detection or measurement) a property (e.g., physiological property) associated with the body 102 in which the implantable device 104 is located, and/or configured to record, indicate or otherwise respond to the detected property.

Employing detection devices and/or sensors, the implantable device 104 and/or the external device 114 can detect, over a defined detection period, one or more different signals associated with a specific physiological state of the body 102 of the patient, a specific movement of the body 102 of the patient, a specific sound/speech detected within the body 102 of the patient and/or a specific sound/speech generated by a user outside the body 102 that is also detected within the body 102 of the patient.

For example, the implantable device 104 can detect, within a defined detection period, a first signal associated with a specific physiological state of the body 102 of the patient, a specific movement of the body 102 of the patient and/or a specific sound/speech generated by the body 102 of the patient. The external device 114 can also detect, within the same detection period, a second signal associated with the specific physiological state of the body 102 of the patient, the specific movement of the body 102 of the patient and/or the specific sound/speech detected within the body 102 of the patient. In some embodiments, the second signal can include or represent an external (e.g., outside the body) effect of the physiological state, movement, or sound/speech. For example, an external effect of speech can include sound generated by the body 102 of the patient and detectable via a microphone (not shown) of the external device 114.

In one embodiment, after or during concurrent detecting of the first and second signals by the implantable device 104 and the external device 114, respectively, the external device 114 is configured to communicate electronic information to the implantable device 104 that is representative of the second signal. In some embodiments, the electronic information is also representative of the detection period over which the second signal was detected. For example, the electronic information can include data corresponding to the raw detected signals and/or processed data corresponding to a characteristic of the physiological state/function of the body 102 in which the implantable device 104 is located, movement of the body 102 in which the implantable device 104 is located and/or sound/speech generated and/or detected within the body 102 in which the implantable device 104 is located. The processed data can be determined based on the raw detected signals.

The implantable device 104 can compare electronic information representative of the first signal with the electronic information representative of the second signal to determine a degree of similarity or correlation between the electronic information for the first and second signals.

Figure 13:
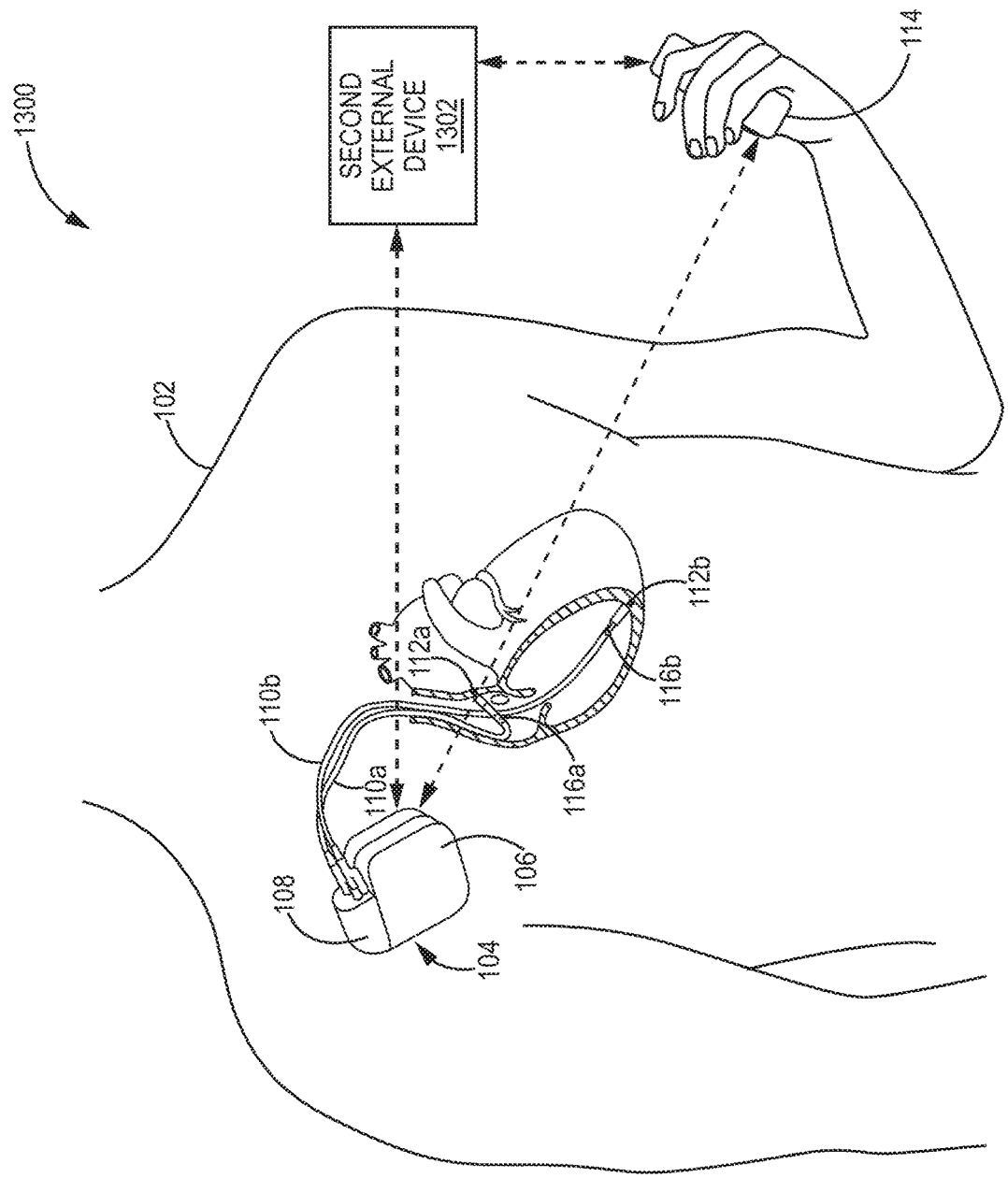
FIG. 13 illustrates a schematic diagram of another example, non-limiting medical device telemetry system facilitating authorized telemetry with an implantable device in accordance with one or more embodiments described herein.

In response to a determination that the electronic information for the first and second signals have a defined degree of similarity or correlation (the degree of which can be dictated by the designer of the implantable device 104 and/or can change from time to time or can change based on different conditions indicating greater or less security risk), the implantable device 104 can initiate a telemetry session with the external device 114 (or another external device as discussed in greater detail with respect to FIG. 13). In response to a determination that the electronic information for the first and second signals fails to exhibit the defined degree of similarity or correlation with one another, the implantable device 104 can forgo authorization and initiation of the telemetry session with the external device 114.

In another embodiment, after or during concurrent detecting of the first and second signals by the implantable device 104 and/or the external device 114, respectively, the implantable device 104 can communicate to the external device 114, electronic information that is representative of the first signal (which is detected by the implantable device 104). In some embodiments, the electronic information representative of the first signal can also identify the defined time period over which the first signal was detected. The external device 114 can then compare electronic information representative of the second signal (which is detected by the external device 114) with the electronic information representative of the first signal. In response to a determination that the electronic information for the first and second signals have a defined degree of similarity or correlation, the external device 114 can authorize and/or initiate a telemetry session with the implantable device 104. In response to a determination that the electronic information for the first and second signals fails to exhibit the defined degree of similarity or correlation, the external device 114 can forgo authorization and initiation of the telemetry session with the implantable device 104.

In one embodiment, the information that is concurrently detected by the external device 114 and the implantable device 104 includes information associated with a rhythm of the heart within the body 102 in which the implantable device 104 is located. According to this embodiment, the implantable device 104 and the external device 114 can include various different types of sensors, and/or circuitry configured to detect information associated with the heart rhythm. The information detected can be processed in various embodiments. For example, the implantable device 104 can include hardware, software, or a combination of hardware and software, that is configured to measure electrical activity of the heart. An electrocardiogram (ECG) is an example of a device that can be employed by the implantable device 104 to record the electrical activity of the heart over a defined period of time, as detected by one or more electrodes (e.g., tip electrodes 112*a,b* or ring electrodes 16*a,b*) connected to one or more parts of the body 102 (e.g., cardiac tissue inside the body 102, skin of the chest outside the body 102 and/or near the heart). An ECG detects electrical impulses generated by the polarization and depolarization of cardiac tissue and translates the impulses into a waveform that corresponds to the rate and regularity of beats of the heart.

In another example, the implantable device 104 can include or be associated with a device (e.g., pulse oximeter) that is configured to detect variation in blood oxygenation level that can be correlated to pulse rate. A pulse oximeter can indirectly monitor the oxygen saturation of the blood in body 102 (as opposed to measuring oxygen saturation directly through a blood sample). The pulse oximeter can utilize the light absorptive characteristics of hemoglobin and the pulsating nature of blood flow through the body 102 to aid in determining the oxygenation status in the body 102. First, there is a color difference between arterial hemoglobin saturated with oxygen, which is bright red, and venous hemoglobin without oxygen, which is dark red. Second, with each pulsation or heartbeat there is generally a slight increase in the volume of blood flowing through the arteries. Because of the increase of blood volume, albeit small, there is generally an associated increase in oxygen-rich hemoglobin. A PPG can be generated based on the amount of oxygen-rich hemoglobin pulsating through the blood vessel volume.

In one embodiment, the implantable device 104 can include a transmittance pulse oximeter. The transmittance pulse oximeter can include a photodetector, a light source, and a circuit that produces, collects, and processes photoplethysmographic signals. The implantable device 104 can activate the transmittance pulse oximeter to generate two wavelengths of light through a part of the body 102 and that is detected by the photodetector. The photodetector can measure the changing absorbance at each of the wavelengths in response to transmittance of the light wavelengths through the body 102. Based on the changes in absorbance, the transmittance pulse oximeter can determine the pulse rate of the patient.

In another embodiment, the implantable device 104 can include a reflectance pulse oximeter to determine pulse rate of the body 102. The reflectance pulse oximeter can also include a photodetector, a light source, and a circuit that produces, collects, and processes PPG signals. With a reflectance pulse oximeter, the incident light is passed through the body and is reflected from the subcutaneous tissue and bone back to the photodetector.

The external device 114 can also include or employ various sensors and/or circuitry configured to process information associated with heart rhythm. In one embodiment, the external device 114 can include a heart rate monitoring device configured to sense electrical activity of the heart when placed against the body 102 near the chest. According to this embodiment, the heart rate monitoring device can operate as an ECG. As discussed above, the electrical signals sensed by the ECG can be used by the external device 114 and/or the heart rate monitoring device to determine the pulse rate of the body 102.

In another embodiment, the external device 114 can include a transmittance or reflectance pulse oximeter configured to determine pulse rate based on detected changes in blood oxygenation levels when the pulse oximeter is contacted with an external part of the body 102 of the patient. For example, the external device 114 can include or be communicatively coupled to a pulse oximeter configured to detect pulse rate in response to placement of the pulse oximeter on the finger or wrist of the body 102 in which the implantable device 104 is located.

In another embodiment, the external device 114 can include a video camera and employ functionalities of the video camera to detect pulse rate within the body 102 in which the implantable device 104 is located. For example, the video camera can capture changes in skin color of the body 102 that can occur based on pulsating blood flow. The pulsating blood flow can be detected in response to placement of a part (e.g., finger) of the body 102 on or near the video camera for a defined detection period. The external device 114 can correlate signals corresponding to changes in skin color to variances in blood oxygenation levels, which can be further correlated to pulse rate.

In yet another embodiment, the external device 114 can capture information regarding pulse rate within the body 102 by detecting changes in reflectance properties of the face associated with the body 102 by using a camera of the external device 114. For example, the increase in blood volume as the blood vessels in the face expand with every heart beat causes more light to be absorbed, resulting in a decrease in the amount of light reflected from the face. External device 114 can employ a camera that is configured to detect signals corresponding to differences in light reflection from the face over a defined detection period. The external device 114 can further correlate these signals to the pulse rate within the body 102.

When or after the implantable device 104 detects first signals associated with a heart rate of the body 102 and the external device 114 detects second signals associated with the heart rate of the body 102 over a defined, overlapping period of time, the first and second signals may correspond to one another. For example, a pulse rate by a body 102 determined by the implantable device 104 based on the electrical signals of an ECG reading by the implantable device 104 or an IMD associated with the implantable device 104 can be the same as, or substantially similar to, a pulse rate determined for the same body 102 by the external device 114 over the defined period of time based on signals captured using a pulse oximeter or camera of the external device 114.

In one or more embodiments, the external device 114 can provide, to the implantable device 104, first electrical information regarding signals detected by the external device 114 and associated with the heart rate of the body 102 (e.g., ECG data, PPG data, image data corresponding to variances in blood oxygenation levels and/or a determined pulse rate). By contrast, in one or more embodiments, implantable device 104 can provide, to the external device 114, second electrical information regarding signals detected by the implantable device 104 and associated with the heart rate of the body. The implantable device 104 and/or the external device 114 can then determine a degree of similarity or correlation between the first and second electrical information. For example, the implantable device 104 and/or the external device 114 can determine a degree to which the first and second electrical information correspond to the same heart rate. In response to a determination that the degree of similarity or correlation between the first and second electrical information is greater than or equal to a threshold value, the implantable device 104 and/or the external device 114 can authorize and/or initiate a telemetry session.

Because the techniques employed by the external device 114 to capture information regarding a heart rate of the body 102 employ a framework in which the external device 114 is touching or is within close proximity to the body 102 in which the implantable device 104 is implanted, correspondence between the different heart rate information captured and determined by the implantable device 104 and the external device 114 can indicate that the external device 114 (or a user of the external device 114) and the patient in which the implantable device 104 is implanted are in a trusted relationship. For example, in one embodiment as depicted in system 100, the user of the external device 114 can be the patient having the body 102 in which the implantable device 104 is located. In another example, the user operating the external device 114 can be a trusted person (e.g., a medical caregiver) or device that interfaces directly with the patient in which the implantable device 104 is implanted. Therefore, correspondence between the different heart rate information captured and determined by the implantable device 104 and the external device 114 can be used to authorize a telemetry session between the implantable device 104 and the external device 114 (or between the implantable device 104 and another external device).

In another embodiment, the information that is concurrently detected by the external device 114 and the implantable device 104 includes information associated with respiration within the body 102 in which the implantable device 104 is located. For example, the implantable device 104 and/or the external device 114 can include hardware, software, or a combination of hardware and software, that is configured to detect signals representative of a respiratory rate of the body 102 of the patient. Respiratory rate refers to the number of breaths (e.g., inhalation-exhalation cycles) taken within a particular amount of time. In another example, the implantable device 104 and/or the external device can include hardware, software, or a combination of hardware and software, that is configured to detect signals representative of respiratory minute volume. A respiratory minute volume is the volume of air that is inhaled (e.g., inhaled volume) or exhaled (e.g., exhaled volume) from the lungs in a defined time period (e.g., one minute).

In accordance with this embodiment, the implantable device 104 and the external device 114 can include various different types of sensors and/or circuitry configured to measure gas volume, gas flow, gas pressure and/or gas concentration. These sensors can include, but are not limited to, volume displacement spirometers, pressure-drop pneumotachometers, hot wire anemometers, turbines, pressure transducers, thermal conductivity meters, infrared (IR) gas analyzers, emission spectroscopy analyzers, and/or gas chromatography (GC) analyzers.

In another embodiment, the implantable device 104 and/or the external device 114 can include or utilize one or more sensors and/or circuitry configured to perform impedance pneumography. Impedance pneumography involves using two or four electrodes in contact with the chest (e.g., either internally or externally) of the body 102. One or more of the electrodes can measure electrical impedance of the thorax of the body 102. Signals associated with electrical impedance of the thorax can be representative of or employed to determine the breathing rate within the body 102.

In another embodiment, the implantable device 104 and/or the external device 114 can include or employ an optical interferometer device to determine a rate of the heart within the body 102. An interferometer device includes optical fibers, and is configured to detect physical changes of optical fiber length due to external perturbations. When in direct or indirect contact with the body 102, mechanical and acoustic activity of cardiac muscle and respiration are indicated in an interferometric signal representative of the respiration rate within the body 102.

In another embodiment, the implantable device 104 and/or the external device 114 can include one or more acoustic sensors to detect information corresponding to a respiration rate within the body 102. For example, the acoustic sensors can detect audio signals associated with breathing (or with cessation of breathing). Based on analysis of the audio signals, the acoustic sensors and/or the implantable device 104 or the external device 114, can determine a respiration rate within the body.

In yet another embodiment, the implantable device 104 and/or the external device 114 can include one or more motion sensors (e.g., an accelerometer, a piezoelectric sensor or a gyroscope) configured to detect motion of the chest, lungs and or diagram of the body 102 in association with breathing or other action (e.g., jumping or running in place). For example, the implantable device 104 can detect motion of one or more aspects of blood or organs inside the body 102, and the external device 114 can detect motion of external portions of the body 102 (e.g., chest or stomach). Motion signals (e.g., signals indicative of displacement, velocity and/or acceleration of the body 102) associated with breathing can reflect a specific pattern or set of periods of movement/non-movement. In an embodiment, the implantable device 104 and/or the external device can deduce a ventilation rate of a body 102 based on the specific pattern or set of periods of movement/non-movement in the motion signals.

In another example, first chest movement data (e.g., corresponding to a pattern or set of expansions/deflations of the lungs of the body 102) detected by the implantable device 104 during a period of ventilation (or breath holding) within the body 102 can be compared with second chest movement data detected by the external device 114 data (e.g., corresponding to a pattern or set of movements/non-movements of rises and falls of the chest of the body 102) during the same period of ventilation (or breath holding) by the patient. The first chest movement data can be compared to the second chest movement to determine whether there is at least a defined degree of similarity between the first chest movement and the second chest movement over a defined time period.

In some embodiments, the first chest movement and the second chest movement can be represented as first electrical information and second electrical information by the implantable device 104 and the external device 114, respectively. In some embodiments, the implantable device 104 and/or the external device 114 can then determine a degree of similarity or correlation between the first and second electrical information. For example, the implantable device 104 and/or the external device 114 can determine a degree to which the first and second electrical information correspond to a same ventilation rate. In response to a determination that the degree of similarity or correlation between the first and second electrical information is greater than or equal to a threshold value, the implantable device 104 and/or the external device 114 can authorize and/or initiate a telemetry session.

The various embodiments discussed above can employ evaluation of the correlation between information associated with any of a number of different types of physiological states of the body 102 (e.g., heart rhythm or ventilation rate) detected by the implantable device 104 and the external device 114 over a same detection period to authorize telemetry between the implantable device 104 and the external device 114 (or between the implantable device 104 and another external device). It should be appreciated, however, that a variety of additional physiological states associated with the body 102 that are capable of being detected by both the implantable device 104 and the external device 114 can serve as a basis for determining whether to authorize telemetry between the implantable device 104 and the external device 114 (or between the implantable device 104 and another external device). For example, in various embodiments, the physiological states can include, but are not limited to, blood pressure, blood composition, temperature or the like.

In another embodiment, in addition to or as an alternative to detection of physiological state of the body 102, the information that is concurrently detected by the external device 114 and the implantable device 104 can include information associated with a movement of the body 102 in which the implantable device 104 is located. According to this embodiment, the implantable device 104 and the external device 114 can each include one or more motion detection sensors or circuitry (e.g., an accelerometer, a gyroscope or a piezoelectric sensor) configured to detect motion signals (e.g., acceleration, orientation, velocity or displacement) corresponding to motion of the body 102 in which the implantable device 104 is located. Information that composes motion data and/or patterns of the motion data can indicate a particular motion of the body 102. For example, information that composes motion data and/or patterns in motion data can reflect sitting, standing, walking, jumping, etc., or can reflect, in some embodiments, more granular motions such as blinking of an eye. Information that composes the motion data and/or patterns in motion data can also correlate to specific positions of the body 102 in a three-dimensional coordinate plane over a duration of a detection period.

In various embodiments, the external device 114 can be held (as depicted in system 100), worn, or otherwise coupled to or in close proximity to the body 102 in which the implantable device 104 is implanted. According to this embodiment, as the body 102 performs a particular motion, the external device 114 and the implantable device 104 can also move in accordance with the motion of the body 102. For example, as the body 102 walks, the implantable device 104 and the external device 114 can experience the walking motion. The implantable device 104 and the external device 114 can therefore each detect information regarding the same walking motion of the body 102 during a defined detection period.

In another embodiment, the external device 114 can include a component that is located remote from the body 102 and configured to detect motion of the body 102. For example, the component can be or include a camera, a laser, or other suitable motion detection device. For example, the external device 114 can include a video camera configured to capture video image data of the body 102 as the body 102 performs a motion. The external device 114 can further include circuitry and/or processing components configured to process the video data to determine or characterize the motion of the body 102. Also according to this embodiment, the implantable device 104 can concurrently detect motion data corresponding to the motion of the implantable device 104 during the detection period. The video data and/or the processed video data and the motion data can later be compared to determine a degree of correlation between the video data (and/or processed video data) and the motion data.

When the implantable device 104 detects first signals associated with motion within a body 102 and the external device 114 detects second signals associated with the motion of the body 102 over a same period of time, the first and second signals can correspond to one another and/or exhibit a known correlation. For example, a motion pattern corresponding to one or more changes in velocity, acceleration, orientation, displacement, etc., for the body 102 captured by the implantable device 104 over a defined duration of time can exhibit similarity to another motion pattern captured by the external device 114 for the body 102 over the same duration of time.

In one or more embodiments, the external device 114 can provide, to the implantable device 104, first electrical information regarding signals detected by the external device 114; or the implantable device 104 can provide, to the external device 114, second electrical information regarding signals detected by the implantable device 104 associated with the motion of the body 102. The device that receives the first or second signal (e.g., the implantable device 104 or the external device 114, depending on the embodiment) can then determine a degree of similarity or correlation between the first and second electrical information. For example, the implantable device 104 and/or the external device 114 can determine a degree to which the first and second electrical information correspond to the same motion or motion pattern. In response to a determination that the degree of similarity or correlation between the first and second electrical information is greater than or equal to a threshold value, the implantable device 104 and/or the external device 114 can authorize and/or initiate a telemetry session.

Because the techniques employed by the external device 114 to capture information regarding motion employ cases in which the external device 114 is attached to (e.g., worn or held) or in close proximity to the body 102 in which the implantable device 104 is located, correspondence between the different motion information captured and determined by the implantable device 104 and the external device 114 can therefore indicate the external device 114 (or a user of the external device 114) and the implantable device 104 (or a body 102 in which the implantable device 104 is implanted)

are in a trusted relationship. Therefore, correspondence between the different motion information captured and determined by the implantable device 104 and the external device 114 can be used to authorize a telemetry session between the implantable device 104 and the external device 114 (or between the implantable device 104 and another external device).

In some embodiments, the external device 114 and/or the implantable device 104 can employ an additional level of security by restricting the particular motion performed by the patient and that is used to authorize telemetry. For example, in addition to determining correspondence between motion data concurrently detected by the implantable device 104 and the external device 114, the implantable device 104 and/or the external device 114 can determine a specific motion (e.g., lying down, clapping hands three times or performing a specific dance move) represented by the motion data. For example, in some embodiments, the motion data can be compared to a table that correlates different motion data with motions. The table can be stored in memory or otherwise accessible to the implantable device 104 in various embodiments. The implantable device 104 and/or the external device 114 can be configured to compare the detected motion to a reference motion that is evaluated to determine whether to provide authorization of the telemetry session. For example, the reference motion can be stored in memory of (or otherwise accessible by) the implantable device 104 or the external device 114. According to these embodiments, the external device 114 and/or the implantable device 104 can be configured to authorize the telemetry session in response to a determination that the motion data detected by the implantable device 104 and the external device 114 exhibits a threshold degree of similarity and/or corresponds to particular reference motion data.

Still in yet another embodiment, the information that is detected by the external device 114 and the implantable device 104 can include information associated with a sound detectable by both the external device 114 and the implantable device 104. For example, the sound can be generated by a body 102 in which the implantable device 104 is located. The sound can be generated by a spoken voice, singing, a melodic hum, etc. In another example, the sound can include a digital sound generated by the external device 114. In yet another example, the sound can include a sound generated by another device, user, musical instrument, etc. within audible range of the implantable device 104 and the external device 114. According to these embodiments, the implantable device 104 and the external device 114 can each include one or more acoustic sensors, digital sound recording devices, or motion detection sensors (e.g., an accelerometer, a gyroscope or a piezoelectric sensor) and associated circuitry to detect and process audio signals. In some embodiments, the external device 114 can detect audio signals associated with sound via an analog or digital acoustic sensor (e.g., a microphone). The implantable device 104 and/or the external device 114 can determine various features of the audio signal (e.g., frequency, bandwidth, period, amplitude or waveform). In some embodiments, the external device 114 and/or the one or more acoustic sensors can further process the audio signals to perform audio fingerprinting or voice to text recognition.

The implantable device 104 can also employ an acoustic sensor to process audio signals associated with a sound generated by the body 102 in which the implantable device 104 is located. For example, using an acoustic sensor, the implantable device 104 can detect sound waves resonated within the body 102 or sound waves traveling through the tissue of the body 102.

In another example, the implantable device 104 can detect vibrations resonating through the body 102 in response to a sound generated by the body 102 in which the implantable device 104 is implanted. For example, to generate the human voice, the human vocal cords vibrate, modulating the flow of air being expelled from the lungs. This process is called phonation. In particular, phonation is the process by which the vocal cord folds to produce certain sounds through quasi-periodic vibration. The vocal cords are open during inhalation, closed when holding one's breath, and vibrating for speech or singing. Accordingly, implantable device 104 can employ various motion sensors (e.g., an accelerometer, piezoelectric device or a gyroscope) to detect vibrations associated with the vibration of the vocal cords when employed to generate sound (e.g., speech, singing or laughing).

When the implantable device 104 detects first signals associated with a particular sound and the external device 114 detects second signals associated with the particular sound over the same period of time, the first and second signals can correspond to one another in some cases. For example, a waveform associated with a particular sound detected by the external device 114 can exhibit similarity to, or correlation with, another waveform detected by the implantable device 104 for the particular sound.

In one or more embodiments, the external device 114 can provide, to the implantable device 104, first electrical information regarding signals detected by the external device 114 associated with the sound. In one or more embodiments, the implantable device 104 can provide, to the external device 114, second electrical information regarding signals detected by the implantable device 104. The implantable device 104 and/or the external device 114 that receives the first or second electrical information can then determine a degree of similarity or correlation between the first and second electrical information. In response to a determination that the degree of similarity or correlation between the first and second electrical information is greater than or equal to a threshold value, the implantable device 104 and/or the external device 114 can authorize and/or initiate a telemetry session.

In some embodiments, the external device 114 and/or the implantable device 104 can employ an additional level of security by restricting the particular sound that is used to authorize telemetry, such as a particular word, phrase, song or melody. For example, in addition to determining correspondence between sound data concurrently detected by the implantable device 104 and the external device 114, the implantable device 104 and/or the external device 114 can determine a specific sound waveform, audio fingerprint, or other distinguishing characteristic of the sound. The implantable device 104 and/or the external device 114 can be configured to compare the detected sound waveform, audio fingerprint, etc., to a reference sound waveform or audio fingerprint that is utilized for authorization of the telemetry session. For example, the reference sound waveform or reference audio fingerprint can be stored in memory of (or otherwise accessible to) the implantable device 104 and/or the external device 114. According to this embodiment, the external device 114 and/or the implantable device 104 can be configured to authorize the telemetry session in response to determination that the sound data detected by the implantable device 104 and/or external device 114 exhibits a threshold degree of similarity to, or corresponds with, the reference sound data (e.g., reference sound wave or reference audio fingerprint) stored in memory of and/or accessible to the implantable device 104 and/or the external device 114.

Figure 2:
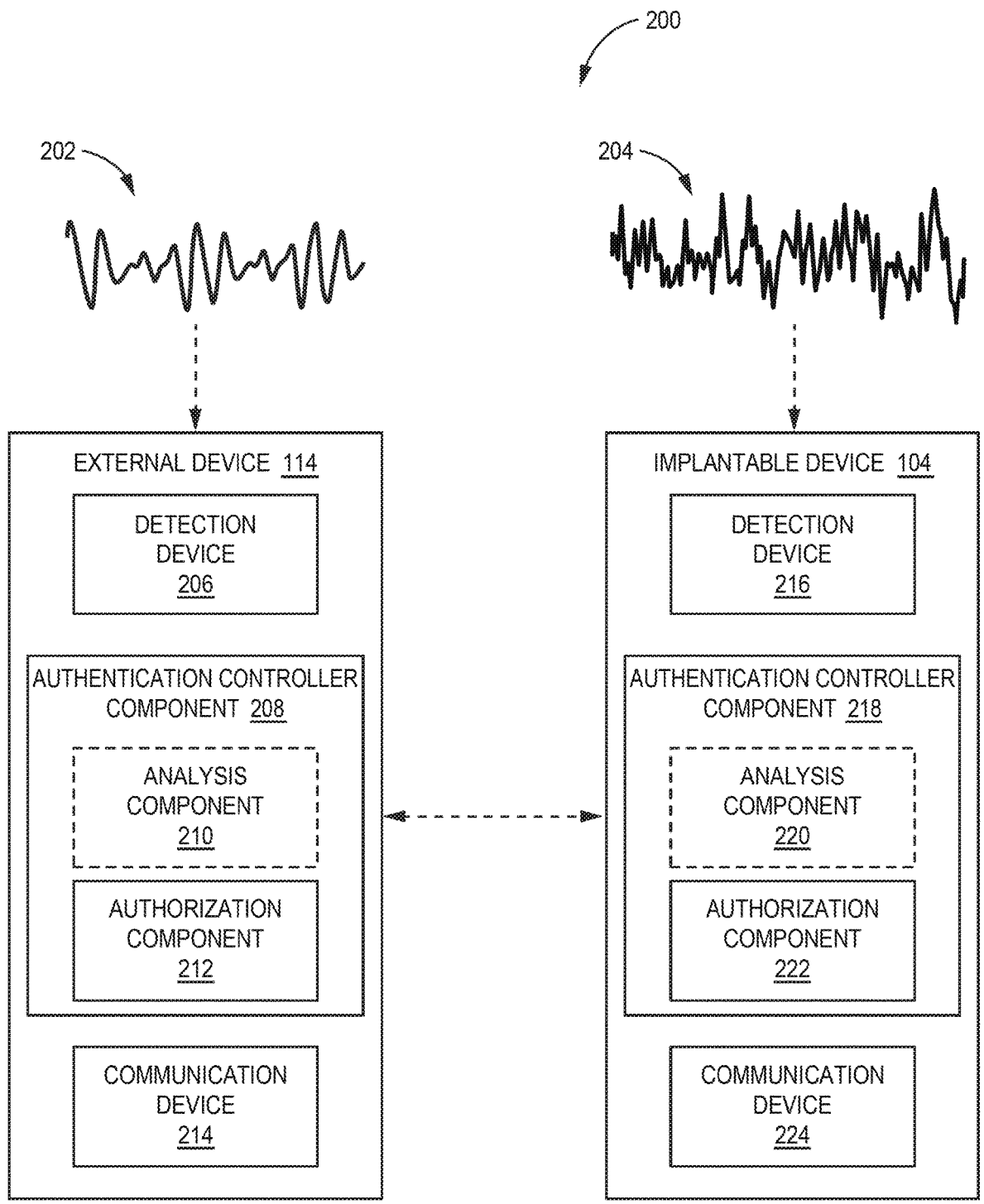
FIG. 2 illustrates a block diagram of a non-limiting system facilitating authorized telemetry with an implantable device and an external device based on concurrent detection, by the implantable device and the external device, of signals associated with a patient in which the implantable device is implanted in accordance with one or more embodiments described herein.

FIG. 2 illustrates a block diagram of a non-limiting system 200 facilitating authorization of telemetry with an implantable device and an external device based on concurrent detection, by the implantable device and the external device, of signals associated with a body of a patient in which the implantable device is implanted in accordance with the first group of embodiments of system 100 described herein. Repetitive description of like elements employed in other embodiments described herein is omitted for sake of brevity.

Similar to system 100, system 200 includes external device 114 and implantable device 104. Although not shown, it is to be appreciated that the implantable device 104 is implanted within a body of a living being (e.g., body 102). For exemplary purposes, system 200 is described with the assumption that the implantable device 104 is implanted within a human being. In other embodiments, the system 200 can apply to or be employed for animals or other living beings.

As depicted in system 200, the external device 114 and the implantable device 104 are configured to perform concurrent detecting of different signals 202 and 204, respectively. As discussed supra, in one or more embodiments, these signals 202 and 204 can include different information associated with a physiological state of a body in which the implantable device 104 is implanted. For example, signals 202 and 204 can each represent raw data that can be correlated to a heart rate, ventilation rate and/or blood pressure. This raw data can vary depending on the implementation of system 200 and the detection devices (e.g., detection device 206 and detection device 216) employed by the external device 114 and the implantable device 104. For example, in embodiments in which external device 114 is configured to detect signals associated with heart rate using a pulse oximeter, signal 202 can include information corresponding to variation in absorbance of wavelengths of light captured by a photodiode in response to transmittance of the different wavelengths of light through blood. Similarly, in embodiments in which the implantable device 104 is configured to detect signals associated with heart rate using an ECG device, signal 204 can include information corresponding to electrical activity of the heart.

In another example, signals 202 and 204 can respectively include raw motion data based on motion of the body in which the implantable device 104 is implanted. For example, in embodiments in which the external device 114 is held, worn, or otherwise attached to the body in which the implantable device 104 is implanted, signal 202 generated by the external device 114 can vary in response to movement of the body. Accordingly, signal 202 can include first motion data (e.g., velocity measurements, acceleration measurements or displacement measurements) corresponding to motion of the external device 114 in response to movement of the body in which the implantable device 104 is implanted. Similarly, signal 204 can include second motion data (e.g., velocity measurements, acceleration measurements or displacement measurements) corresponding to motion of the implantable device 104 in response to the motion of the body in which the implantable device 104 is implanted.

As another example, signals 202 and 204 can each include raw data that can be generated based on a walking motion, a lying down motion (or position), a jumping motion, a spinning motion, a hand raising motion, etc, made by the body in which the implantable device 104 is implanted. This raw data can vary depending on the implementation of system 200 and/or the detection devices (e.g., detection device 206 and detection device 216) employed by the external device 114 and the implantable device 104. For example, when external device 114 is configured to detect motion signals using an accelerometer, signal 202 can include acceleration measurements corresponding to the acceleration of the external device 114 over the duration of the detection period. Similarly, when implantable device 104 is configured to detect motion signals using a piezoelectric device, signal 204 can include information corresponding to changes in pressure, acceleration, strain or force experienced by the implantable device 104.

In yet another example, signals 202 and 204 can each include raw data corresponding to a sound that is concurrently detected by external device 114 and implantable device 104. In one embodiment, the concurrently detected sound includes a voice sound made by the body in which the implantable device 104 is implanted. In another embodiment, the concurrently detected sound can include a sound generated by the external device 114. In yet another embodiment, the concurrently detected sound can include a sound made by another device, person, object, etc. Accordingly, the data of raw signals 202 and 204 can vary depending on the implementation of system 200 and the detection devices (e.g., detection device 206 and detection device 216) employed by the external device 114 and the implantable device 104.

As another example, when external device 114 and implantable device 104 are configured to employ acoustic sensors, signal 202 can include first sound waves received or detected at the external device 114 and signal 204 can include second sound waves received or detected at the implantable device 104 (e.g., through the body). In another example, when the concurrently detected sound includes a voice sound made by the body in which the implantable device 104 is implanted, signal 204 can also include vibration data corresponding to vibration of the vocal cords during production of the sound.

In various embodiments, external device 114 can include a detection device 206, an authentication controller component 208, and a communication device 214. The detection device 206 is configured to detect signal 202 and the like (e.g., signals associated with a physiological state of the body in which the implantable device 104 is implanted, a motion of the external device 114 and/or a sound) using one or more sensors, devices, and/or circuitry within or electrically (or mechanically) coupled to the external device 114. These sensors, devices and/or circuitry can vary depending on the implementation of system 200.

For example, as discussed supra, in one implementation, detection device 206 is configured to detect or measure physiological data associated with a rhythm of the heart of the body in which the implantable device 104 is implanted. In accordance with this implementation, detection device 206 can include, but is not limited to, an ECG device, a transmittance pulse oximeter device and/or a reflectance pulse oximeter device. Detection device 206 can also include a video camera and associated circuitry/software configured to capture and process changes in skin color based on pulsating blood flow in response to placement of a part of the body (e.g., a finger) on the video camera, and/or associated circuitry/software configured to capture and process reflectance properties of the face or body part.

In another implementation, detection device 206 is configured to detect physiological data associated with ventilation of the body in which the implantable device 104 is implanted. In accordance with this implementation, detection device 206 can include different types of sensors, and/or circuitry, configured to measure gas volume, gas flow, gas pressure, or gas concentration. These sensors can include, but are not limited to, volume displacement spirometers, pressure-drop pneumotachometers, hot wire anemometers, turbines, pressure transducers, thermal conductivity meters, IR gas analyzers, emission spectroscopy analyzers, and GC analyzers. In accordance with this implementation, detection device 206 can also include an optical interferometer device, acoustic sensors (e.g., to detect audio signals associated with inhalation and exhalation), and/or motion sensors (e.g., an accelerometer, a piezoelectric sensor, a gyroscope or a pressure sensor) configured to detect motion of the chest, lungs and/or diaphragm in association with inhalation and exhalation.

In another implementation, detection device 206 is configured to detect motion data associated with movement of the external device 114, and more particularly, movement of the external device 114 in response to movement of the body in which the implantable device 104 is implanted or when the external device 114 is held or worn by the body (or otherwise attached to the body). In accordance with this implementation, detection device 206 can include, but is not limited to, an accelerometer, a gyroscope, and/or a piezoelectric sensor (e.g., a piezoelectric displacement sensor, a piezoelectric velocity sensor or a piezoelectric pressure sensor).

In another implementation, detection device 206 is configured to detect motion data associated with movement of the body in which the implantable device 104 is implanted in embodiments in which the external device 114 is not held or worn by the body (and not otherwise attached to the body). In accordance with this implementation, detection device 206 can include, but is not limited to, a camera, a laser, or another suitable motion detection device configured to capture information regarding motion of the body when the body is located at a distance from the detection device 206.

In yet another implementation, detection device 206 is configured to detect audio signals associated with a sound generated within audible range of the external device 114. For example, the sound can include a voice of the body in which the implantable device 104 is implanted, a sound emitted by the external device 114 (e.g., via a speaker (not shown) of the external device 114) or a sound made by another user, device or object within proximity of the external device 114. In accordance with this implementation, detection device 206 can include, but is not limited to, one or more analog acoustic sensors, one or more digital acoustic sensors, and/or one or more motion sensors configured to detect vibrations associated with sound (e.g., an accelerometer or a piezoelectric device).

The detection device 206 can be further configured to generate electronic output data corresponding to the signal 204 detected by the detection device 206. In some embodiments, the electronic output data can include raw data corresponding to one or more parameters of the signal 204, which can vary depending on the implementation of the detection device 206. For example, in embodiments in which detection device 206 includes an ECG, the raw data can include information indicative of voltage variations associated with electrical impulses generated by the polarization and depolarization of cardiac tissue over the detection period. In another example, in embodiments in which the detection device 206 includes an accelerometer, the raw data can include information indicative of one or more changes in acceleration over the detection period. In other embodiments, the electronic output data can include partially processed or processed raw data signals. For example, in embodiments in which the detection device 206 includes an ECG, an electronic output representative of partially processed data can include a waveform corresponding to the electrical impulses generated by the polarization and depolarization of cardiac tissue over the detection period. The detection device 206 can further be configured to generate an electronic output based on additional processing of the raw detected signal 204. Continuing with the ECG example, the detection device 206 can be configured to generate electronic output data identifying a detected heart rate based on the signal 204 detected by detection device 206.

In various embodiments, the electronic output data provided by the detection device 206 can be generated by circuitry designed to output specific types of information or electrical signals based on changes in mechanical, electrical or electromechanical features or components of one or more sensors, devices or circuits that can be included in, or otherwise associated with, the detection device 206.

In various embodiments, communication device 214 facilitates communication between the external device 114 and another device (e.g., implantable device 104 or another device). For example, communication device 214 can include or be various hardware and software devices associated with establishing and/or conducting a telemetry session between the external device 114 and the implantable device 104.

Communication device 214 can be configured to communicate with another device using various wireless communication protocols. For example, communication device 214 can include a transmitter and/or receiver configured to transmit and/or receive electrical wireless signals. As another example, communication device 214 can be configured to communicate with another device using various wireless communication protocols including, but not limited to, NFC, BLUETOOTH® technology, ZigBee®, radio frequency (RF) communications, SIP-based communications, cellular communication, or other forms of communication including both proprietary and non-proprietary communication protocols.

The authentication controller component 208 is configured to facilitate various operations of external device 114 in connection with facilitating an authorized telemetry session between external device 114 and implantable device 104 (or another external device). In various embodiments, the authentication controller component 208 can include analysis component 210 and authorization component 212.

In association with systems 100, 200 and the first group of embodiments, the authentication controller component 208 can activate detection device 206 in association with input received at the external device 114 requesting establishment of a telemetry session between external device 114 and implantable device 104 (or another external device). According to this example, in response to receipt of the input, the authentication controller component 208 can activate detection device 206 to cause the detection device 206 to detect or measure a type of signal the detection device 206 is configured to detect (e.g., an ECG based signal, a pulse oximeter based signal, an image data or video signal, an audio signal or a motion signal).

In another embodiment, in embodiments in which the detection device 206 includes or employs hardware and/or software configured to detect several different types of signals, the authentication controller component 208 can control the operation of the detection device 206 to detect a particular desired type of signal. The authentication controller component 208 can also control the duration of the detection period in some embodiments. By way of example, but not limitation, the authentication controller component 208 can transmit a signal to the detection device 206 that causes the detection device 206 to perform a particular detection operation and/or causes the detection device 206 to perform detection for a defined period of time.

Depending on the type of signal the detection device 206 is configured to detect, the authentication controller component 208 can also cause information to be output (e.g., via an audible signal or via a prompt on a user interface of the external device 114) from the external device 114 to cause the body in which the implantable device 104 is implanted to perform a particular action (e.g., sing a song, speak a word or walk in place). For example, in association with activating the detection device 206, the authentication controller component 208 can output information to cause the body in which the implantable device 104 is implanted to perform a particular physical action for the duration of the detection period to facilitate capturing distinct physiological reaction signals and/or motion signals (e.g., a heart rate resultant from the physical action, a ventilation rate resultant from the physical action or a detectable motion pattern).

The authentication controller component 208 can also facilitate initializing an authentication process between external device 114 and implantable device 104 based on concurrent detecting of signals 202 and 204 by the external device 114 and the implantable device 104, respectively. For example, in some embodiments, detection device 216 of the implantable device 104 can be configured to detect signals such as signal 204. In other embodiments, the detection device 216 can be configured to react to a particular signal 204 and begin detecting for a defined detection period. Signal 204 can be detected concurrently with detection of signal 202 in some embodiments. According to these embodiments, the particular signal 202 and/or the period over which the signal 202 is captured by the external device 114 can be controlled at the external device 114 (e.g., by the authentication controller component 208 and/or based on input received at the external device 114). Signal 202 can then be correlated to a detected signal 204 (which can be received at the external device 114 from the implantable device 104 in some embodiments).

In some embodiments, the authentication controller component 208 can transmit (e.g., using communication device 214), a request message to the implantable device 104 requesting performance of a concurrent sensing authentication process in association with authorizing and/or establishing a telemetry session between the external device 114 and the implantable device 104 (or another external device). For example, this request message can be generated and sent in response to input received at the external device 114 requesting pairing between the implantable device 104 and the external device 114 (or another external device).

According to this embodiment, the communication device 214 can employ a particular frequency (e.g., a non-commercial frequency) to send the request message as an RF data signal that is recognizable by the implantable device 104 as a request to pair with the implantable device 104. In one implementation, in response to transmission of the RF data signal by the external device 114 and reception and identification of the RF data signal by the implantable device 104 (e.g., via the authentication controller component 218), the implantable device 104 and the external device 114 can activate respective detection devices 206 and 216 and begin detecting signals 202 and 204 over a defined detection period. In some embodiments, the duration of the detection period and/or the start time of the detection period can be included in the RF data signal or defined in memory of the external device 114 and the implantable device 104, respectively.

In another implementation, in response to transmission of the RF communication signal by the external device 114 and reception and identification of the RF data signal by the implantable device 104, the implantable device 104 can send an acknowledgment message (e.g., using an RF data signal) back to the external device 114 acknowledging receipt of the request to perform the concurrent sensing. In an embodiment, in response to sending the acknowledgment message, the implantable device 104 (e.g., via authentication controller component 218) can activate detection device 216 to begin detecting for a defined detection period (e.g., for one minute after sending the acknowledgment message). In addition, in response to reception of the acknowledgment message by the external device 114 (e.g., via communication device 214), the authentication controller component 208 can activate detection device 206 to begin detecting for a defined detection period (e.g., for one minute after reception).

In another embodiment, the defined detection period can be determined and provided by the implantable device 104 in the acknowledgment message (e.g., via authentication controller component 218). For example, the acknowledgment message can state the detection period as being from time T1 to time T2. Upon the occurrence of time T1 (e.g., which may be a defined start time within about one minute of sending the acknowledgment message), both the external device 114 and the implantable device 104 can begin detecting as directed by respective authentication controller components 208 and 218, respectively.

A variety of other techniques can be employed to inform and direct the external device 114 and/or the implantable device 104 when to begin concurrently detecting signals 202 and 204 in association with gathering authorization information to facilitate a telemetry session between the respective devices. For example, the respective detection devices 206 and 216 can be configured to begin detecting for a defined detection period in response to detection of a specific synchronization signal. According to this example, the synchronization signal can be provided by the external device 114 to the implantable device 104, or vice versa, or the synchronization signal can be provided by another device or entity. In another example, the respective detection devices 206 and 216 can be configured to begin detecting for a defined duration in response to concurrent detection of one or more magnetic fields.

Analysis component 210 is configured to perform various analytical functions of external device 114 in connection with facilitating an authorized telemetry session between external device 114 and implantable device 104. In association with systems 100, 200 and the first group of embodiments, the analysis component 210 is configured to perform various analytical functions associated with determining a degree of similarity or correlation between signals 202 and 204.

For example, in one embodiment, after or during concurrent detecting, of signals 202 and 204 by the external device 114 and the implantable device 104, respectively, the implantable device 104 is configured to communicate electronic information to the external device 114 representative of signal 204 and that can identify the detection period over which signal 204 was detected. According to this embodiment, analysis component 210 is configured to compare signals 202 and 204, and/or electronic information corresponding to signals 202 and 204 based on association of signals 202 and 204 with the same detection period. For example, using the information representative of signal 204 and the information identifying the period over which signal 204 was detected, analysis component 210 can compare the information representative of signal 204 with information corresponding to detected signal 202. The analysis component 210 can further determine whether signals 202 and 204 have a defined degree of similarity to, or correlation with, one another. For example, the analysis component 210 can determine whether the signals 202 and 204 have a defined degree of similarity/correlation that is greater than or equal to a minimum degree of similarity/correlation. The defined degree of similarity can vary depending on the implementation of system 200. For example, system 200 can require signals 202 and 204 to have a 100% degree of similarity/correlation, a 90% degree of similarity/correlation, a 60% degree of similarity/correlation, or any other degree of similarity/correlation. In some embodiments, the required degree of similarity/correlation can change from time to time or at scheduled times based on a change in the programming of the implantable device 104 or the external device 114 and/or based on the type of signal detected, security risk, environment in which the detection is performed (e.g., physician office versus home location) or any number of factors.

For example, in an embodiment, the information representative of signals 202 and 204 employed by analysis component 210 to perform the comparison includes raw data associated with signals 202 and 204. For example, signal 204 can include data identifying voltage variations associated with electrical impulses in cardiac tissue. Signal 202 can include similar raw data or another form of raw data associated with a heart rhythm. Analysis component 210 can compare this raw data for signals 202 and 204 to determine whether signals 202 and 204 have a defined degree of similarity or correlation.

In yet another embodiment, analysis component 210 can process the raw data of signals 202 and/or 204 to determine information corresponding to the raw data signals (e.g., a heart rate, a ventilation rate, a waveform, an audio fingerprint of the waveform, a motion pattern or a particular motion represented by the motion pattern). The analysis component 210 can then analyze and compare the processed information corresponding to the raw data signals 202 and 204 to determine whether the processed information for signals 202 and 204 have a defined degree of similarity or correlation.

In various embodiments, implantable device 104 can receive signal 202. Analysis component 220 can process raw data of signals 202 and 204 and/or signals 202 and 204, analyze the raw data or signals or perform any number of functions to determine whether the raw data of signals 202 and 202 and/or signals 202 and 204 have a defined degree of similarity or correlation.

Authorization component 212 is configured to perform various operations of external device 114 in connection with facilitating an authorized telemetry session between external device 114 and implantable device 104. In association with systems 100, 200 and the first group of embodiments, authorization component 212 is configured to initiate, conduct or otherwise approve/enable a telemetry session with the implantable device 104 in response to a determination that signals 202 and 204 exhibit a defined degree of similarity or correlation (e.g., as determined by analysis component 210 and/or analysis component 220).

For example, in various embodiments wherein comparative analysis of signals 202 and 204 is performed by analysis component 210, in response to a determination that signals 202 and 204 (or electronic information representative of signals 202 and 204) exhibit a defined degree of similarity or correlation, authorization component 212 can send an authorization communication to the implantable device 104 indicating that the external device 114 has authorized the requested telemetry session. In response to reception of the authorization communication, authorization component 212 and/or authorization component 222 can facilitate the exchange of security information between the implantable device 104 and the external device 114 in association with establishing the authorized telemetry session. For example, communication devices 224 and 214 can exchange security information (e.g., device identifiers for the external device 114 and the implantable device 104) and/or session keys in accordance with suitable existing pairing technology. In an embodiment, the session keys can be set to expire after a defined duration of time.

The authentication controller component 208, analysis component 210 and/or authorization component 212 can be further configured to facilitate various additional operations of external device 114 in connection with facilitating an authorized telemetry session between external device 114 and implantable device 104 (or another external device) based on several additional mechanisms discussed herein with respect to second, third and fourth groups of embodiments of system 100, discussed infra. The various additional features and functionalities of the authorization component 212 with respect to the second, third, and fourth groups of embodiments of system 100 are discussed in greater detail with respect to FIGS. 7, 13, 17 and 18.

In various embodiments, implantable device 104 can include a detection device 216, a communication device 224, and an authentication controller component 218 having an analysis component 220 and an authorization component 222.

Communication device 224 can include one or more of the structure, features and/or functionalities of communication device 214. For example, communication device 224 can include a transmitter and/or receiver configured to transmit and/or receive electrical wireless signals. As another example, communication device 224 can be configured to communicate with another device using various wireless communication protocols including, but not limited to, NFC, BLUETOOTH® technology, RF communications, SIP-based communications, cellular communication, or other forms of communication including both proprietary and non-proprietary communication protocols.

In association with FIG. 2 and system 200, the operations of detection device 216, authentication controller component 218, analysis component 220, and authorization component 222, are described with respect to their roles at implantable device 104 in connection with the first group of embodiments of system 100 (e.g., in connection with facilitating an authorized telemetry session between external device 114 and implantable device 104 (or another external device) based on concurrent detection of signals 202 and 204 by the external device 114 and the implantable device, respectively). However, similar to their corresponding components in external device 114, detection device 216, authentication controller component 218, analysis component 220, and authorization component 222, can be further configured to facilitate various additional operations of implantable device 104 in connection with facilitating an authorized telemetry session between implantable device 104 and external device 114 (or another external device), based on several additional mechanisms discussed herein with respect to second, third and fourth groups of embodiments of system 100, discussed infra. The various additional features and functionalities of detection device 216, authentication controller component 218, analysis component 220, and authorization component 222, with respect to the second, third, and fourth groups of embodiments of system 100 are discussed in greater detail with respect to FIGS. 7, 13, 14, 17 and 19.

Detection device 216 can include one or more of the structure, features and/or functionalities of detection device 206. For example, detection device 216 can include an ECG device, a pulse oximeter device, volume displacement spirometers, pressure-drop pneumotachometers, motion detection devices, acoustic sensors, etc. However, it should be appreciated that certain detection devices and circuitry that can be included in detection device 206 may not be suitable for inclusion in implantable device 104. For example, detection device 216 may not include a video camera, or camera configured to capture and process changes in facial absorbance properties. In addition, the specific structure and electrical/mechanical configuration of sensors, devices and associated circuitry configured to detect the same signals (e.g., an ECG device or a pulse oximeter device) with the external device 114 and the implantable device 104 can vary. For example, an ECG device configured to be included with an implantable device 104 and implanted inside the body may have a different structure and electrical/mechanical configuration than another ECG device configured to be included with and/or employed by (e.g., as an auxiliary device) external device 114.

Authentication controller component 218, analysis component 220, authorization component 222, can also include one or more of the structure, features and functionalities of authentication controller component 208, analysis component 210, and authorization component 212, respectively. For example, authentication controller component 218 is configured to facilitate various operations of implantable device 104 in connection with facilitating an authorized telemetry session between the implantable device 104 and external device 114 (or another external device) based on concurrent detection of signals 202 and 204 by the external device 114 and the implantable device 104, respectively (i.e., the authentication mechanism described for system 200 and the first group of embodiments of system 100). In an embodiment, authentication controller component 218 can facilitate concurrent detecting by the external device 114 and the implantable device 104 for a defined detection period in accordance with one or more embodiments described for the authentication controller component 208.

For example, authentication controller component 218 can receive a request message from external device 114 that indicates the external device 114 is requesting performance of a concurrent detecting authentication process to initiate a telemetry session between the external device 114 and the implantable device 104 (or between the implantable device 104 and another external device). In response to the request, authentication controller component 218 can control detection device 216 to capture signal 204 over a defined detection period. Authentication controller component 218 can also send an acknowledgement message back to the external device 114 to facilitate concurrent detecting of the external device 114 and the implantable device 104, as described in association with the description of the authentication controller component 208.

With respect to the embodiments described for system 200, analysis component 220 can include one or more of the same or similar structure, features and/or functionalities as analysis component 210. For example, like analysis component 210, analysis component 220 can compare signals 202 and 204, and/or electronic information corresponding to the raw data of signals 202 and 204 and/or processed information corresponding to signals 202 and 204 to determine a degree of similarity to, or correlation between, signals 202 and 204. Analysis component 220 can also process the raw data of signals 202 and/or 204 to determine information corresponding to the raw data signals (e.g., a heart rate, a ventilation rate, a waveform, an audio fingerprint of the waveform, a motion pattern or a particular motion represented by the motion pattern).

Analysis component 210 and analysis component 220 are respectively presented with dashed line boxes to indicate that they can be included or excluded from the authentication controller components 208 and 218, respectively, based on the particular embodiment of system 200. For example, as discussed supra, in one embodiment, after concurrent detecting of signals 202 and 204 by the external device 114 and the implantable device 104, respectively, the external device 114 is configured to communicate electronic information to the implantable device 104 representative of signal 202. In some embodiments, the electronic information can also identify the detection period over which signal 202 was detected. According to this embodiment, the implantable device 104 can employ analysis component 220 to compare the received electronic information representative of signal 202 with electronic information representative of signal 204 based on association with signals 202 and 204 with the same detection period. Based on the comparison, the analysis component 220 is configured to determine a degree of similarity or correlation between signal 202 and signal 204. Because the analysis is being performed by the implantable device 104 in this embodiment, analysis component 210 need not be included in the external device 114.

In another embodiment, after concurrent detecting of signals 202 and 204 by the external device 114 and the implantable device 104, respectively, the implantable device 104 is configured to communicate electronic information to the external device 114 representative of signal 204 and that can identify the detection period over which signal 204 was detected. According to this embodiment, the external device 114 can employ analysis component 210 to compare the received electronic information representative of signal 204 with electronic information representative of signal 202 based on association with signals 202 and 204 with the same detection period. Based on the comparison, the analysis component 210 is configured to determine a degree of similarity or correlation between signal 202 and signal 204. Because the analysis is being performed by the external device 114 in this embodiment, analysis component 220 need not be included in the implantable device 104.

Similar to the authorization component 212, the authorization component 222 is configured to perform various operations of implantable device 104 in connection with facilitating an authorized telemetry session between external device 114 and implantable device 104. For example, in association with systems 100, 200 and the first group of embodiments, authorization component 222 is configured to initiate, conduct or otherwise approve/enable a telemetry session with the external device 114 (or another external device) in response to a determination that signals 202 and 204 exhibit a defined degree of similarity or correlation (e.g., as determined by analysis component 210 and/or analysis component 220).

FIGS. 3, 4, 5 and 6 illustrate flow diagrams of example, non-limiting methods for facilitating authorized telemetry with an implantable device and an external device based on concurrent detection, by the implantable device and the external device, of signals associated with a body of a patient in which the implantable device is implanted in accordance with the first group of embodiments of system 100 described herein. The methods 300, 400, 500, 600 are described with reference to FIGS. 1 and 2 in which the implantable device (e.g., implantable device 104) is embodied in methods 300, 400, 500, 600 as an IMD. Repetitive description of like elements employed in other embodiments described herein is omitted for sake of brevity.

Figure 3:
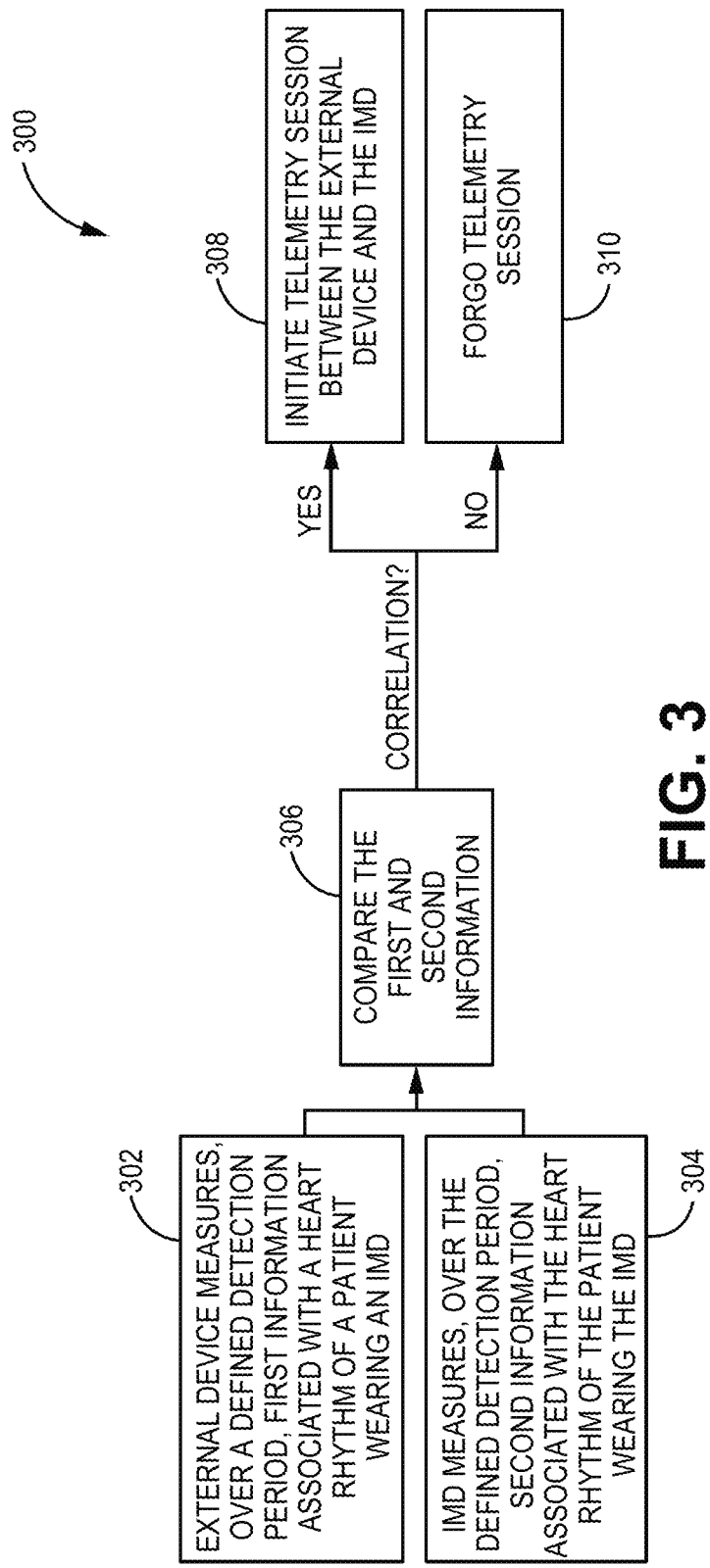
FIG. 3 illustrates a flow diagram of an example, non-limiting method of facilitating authorized telemetry with an IMD and an external device based on concurrent detection, by the IMD and the external device, of information associated with a heart rhythm of a patient in which the IMD is implanted in accordance with one or more embodiments described herein.

FIG. 3 illustrates a flow diagram of an example, non-limiting method 300 facilitating authorized telemetry with an IMD and an external device based on concurrent detection, by the IMD and the external device, of information associated with a heart rhythm of a body of a patient in which the IMD is implanted in accordance with one or more embodiments described herein.

At 302, an external device (e.g., external device 114), measures, over a defined detection period, first information associated with a heart rhythm of a patient wearing an IMD. For example, the external device can activate a camera of the external device and capture image data of indicative of a change in blood color over a defined duration of time in response to placement of a part of a body of the patient (e.g., the patient's finger) over a lens of the camera. As described herein, a patient wearing an IMD can be a patient in which a IMD is implanted, for example. The external device 114 can determine the heart rate of the patient based on the change in blood color. At 304, the IMD measures, over the defined detection period, second information associated with the heart rhythm of the patient wearing the IMD. For example, the IMD can activate an ECG device or a pulse oximeter to capture signals (e.g., electrical activity of the heart, or change in blood oxygenation levels, respectively) that can be correlated to the heart rate of the body of the patient.

The external device can send the first information to the IMD or the IMD can send the second information to the external device. In some embodiments, in lieu of or in addition to the external device sending first information to the IMD or the IMD sending second information to the external device, a tertiary device can receive both the first information and the second information.

In any embodiment, at 306, the device having the first and second information can compare the first and second information. The first and second information is analyzed to determine a degree of similarity or correlation between the first and second information. The degree of similarity can be compared to a defined degree of similarity to determine whether a particular correlation exists. For example, the defined degree of similarity at which a correlation can be determined to have occurred can be approximately 100% (e.g., both heart rate measurements are approximately the same) or approximately 50% (e.g., half of the heart rate measurements are approximately the same). In another example, the defined degree of similarity at which a correlation can be determined to have occurred can accommodate a slight variation in the first and second information (e.g., both heart rate measurements differ by less than 10%).

In response to a determination that the first and second information have the defined degree of similarity or correlation, at 308 the IMD and/or the external device can initiate a telemetry session with one another. Although not shown, in some embodiments, in response to a determination that the first and second information have the defined degree of similarity or correlation, at 308 the IMD and/or the external device can continue an ongoing telemetry session with one another. In response to a determination that the first and second information fail to exhibit the defined degree of similarity or correlation, at 310 the IMD and/or the external device can forgo a telemetry session.

Figure 4:
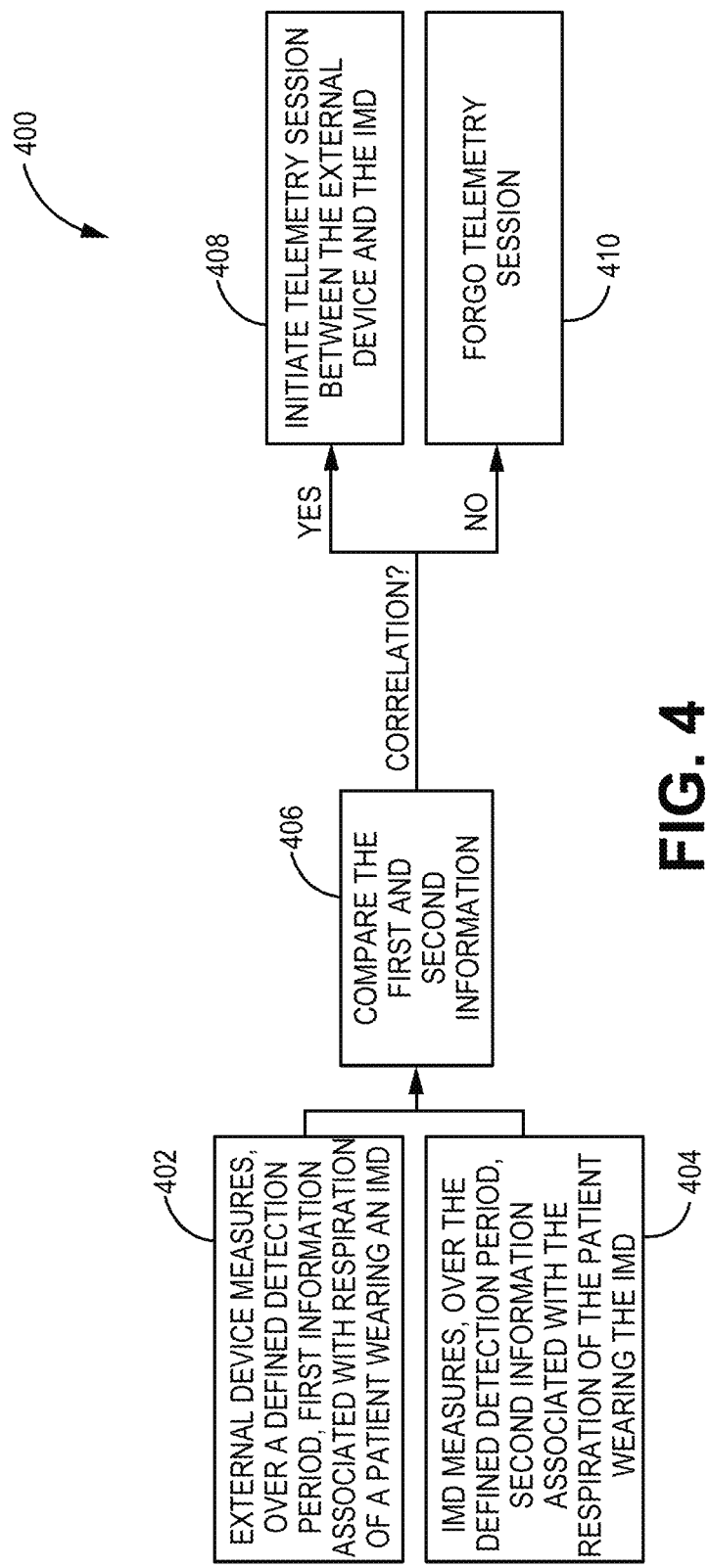
FIG. 4 illustrates a flow diagram of an example, non-limiting method of facilitating authorized telemetry with an IMD and an external device based on concurrent detection, by the IMD and the external device, of information associated with respiration of a patient in which the IMD is implanted in accordance with one or more embodiments described herein.

FIG. 4 illustrates a flow diagram of an example, non-limiting method 400 facilitating authorized telemetry with an IMD and an external device based on concurrent detection, by the IMD and the external device, of information associated with respiration of a body of a patient in which an IMD is implanted in accordance with one or more embodiments described herein.

At 402, an external device (e.g., external device 114) measures, over a defined detection period, first information associated with respiration of a patient wearing an IMD. For example, the external device can detect audio signals associated with breathing of the patient via a microphone of the external device. The external device 114 can further correlate the audio signals with the ventilation rate of the patient. At 404, the IMD measures, over the defined detection period, second information associated with the respiration of the patient wearing the IMD. For example, the IMD can detect signals associated with electrical impedance of the patient's thorax (e.g., pneumography data). The IMD can further correlate the electrical impedance signals with the ventilation rate.

The external device can send the first information to the IMD or the IMD can send the second information to the external device. In some embodiments, in lieu of or in addition to the external device sending first information to the IMD or the IMD sending second information to the external device, a tertiary device can receive both the first information and the second information.

In either embodiment, the device having the first and second information can compare the first and second information at 406. For example, the first and second information is analyzed to determine a degree of similarity or correlation between the first and second information. For example, the IMD, external device and/or tertiary device can compare the ventilation rates determined by the IMD and external device over the same detection period. Based on the comparison, a determination can be made as to whether the first and second information (e.g., the respective ventilation rate measurements) exhibit a defined degree of similarity or correlation (e.g., whether the ventilation rates are the same or substantially the same). In response to a determination that the first and second information have the defined degree of similarity or correlation, at 408 the IMD and/or the external device can initiate a telemetry session with one another. In response to a determination that the first and second information fail to exhibit the defined degree of similarity or correlation, at 410 the IMD and/or the external device can forgo a telemetry session.

Figure 5:
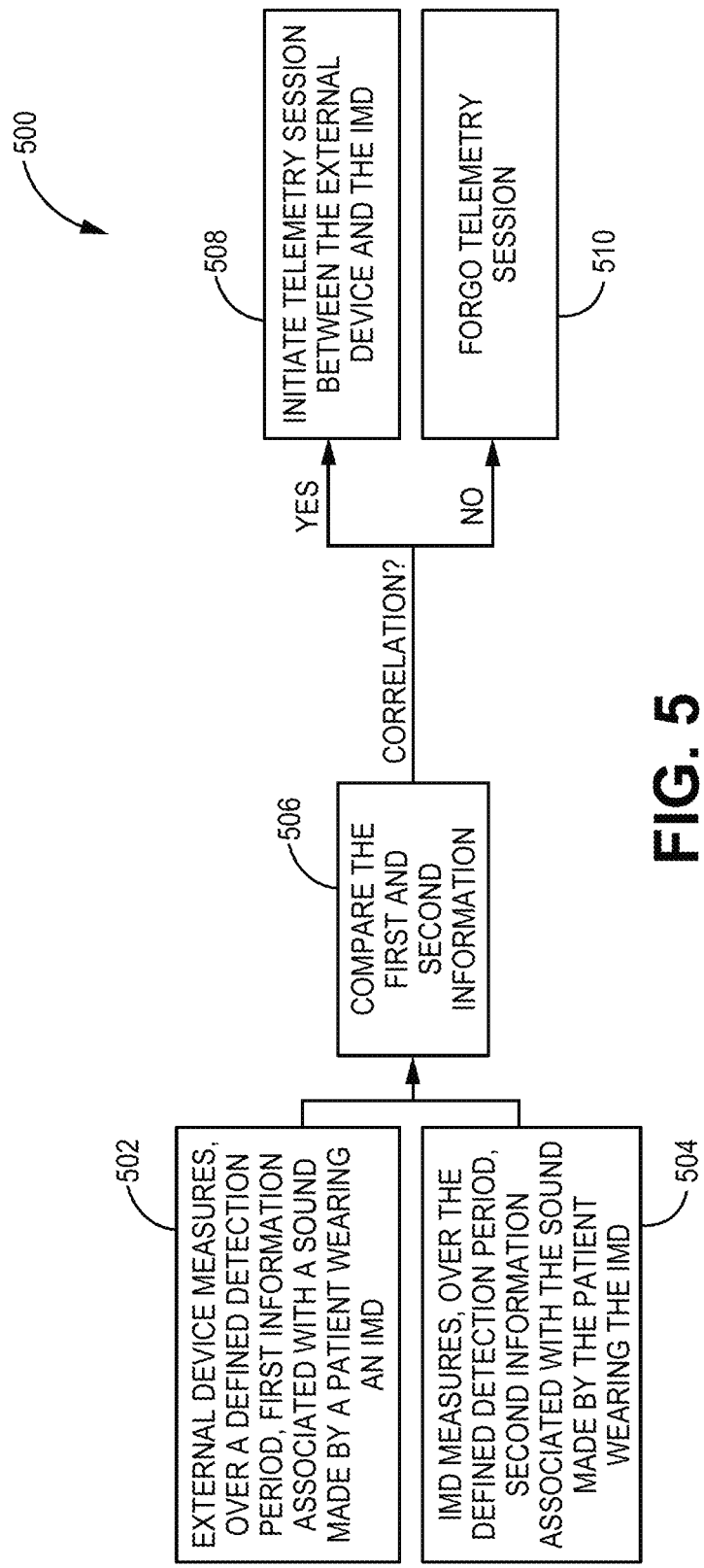
FIG. 5 illustrates a flow diagram of an example, non-limiting method of facilitating authorized telemetry with an IMD and an external device based on concurrent detection, by the IMD and the external device, of information associated with a sound made by a patient in which the IMD is implanted in accordance with one or more embodiments described herein.

FIG. 5 illustrates a flow diagram of an example, non-limiting method 500 facilitating authorized telemetry with an IMD and an external device based on concurrent detection, by the IMD and the external device, of information associated with a sound made by a body of a patient in which an IMD is implanted in accordance with one or more embodiments described herein.

At 502, an external device (e.g., external device 114) measures, over a defined detection period, first information associated with a sound made by a patient wearing an IMD. For example, the external device can detect (e.g., via a microphone) audio signals corresponding to a word or phrase spoken by the patient. At 504, the IMD measures, over the defined detection period, second information associated with the sound made by the patient wearing the IMD. For example, the IMD can detect (e.g., via acoustic and/or vibration sensors) audio signals and/or vibration resonating within the body and associated with the word or phrase spoken by the patient.

The external device can send the first information to the IMD or the IMD can send the second information to the external device. In some embodiments, in lieu of or in addition to the external device sending first information to the IMD or the IMD sending second information to the external device, a tertiary device can receive both the first information and the second information.

The device having the first and second information (e.g., IMD, external device or tertiary device) can compare the first and second information at 506. For example, the first and second information can be compared and analyzed to determine a degree of similarity or correlation between the first and second information. For example, the IMD or the external device can compare the audio signals captured by the respective devices.

Based on the comparison, a determination can be made as to whether the first and second information (e.g., the respective audio signals) exhibit a defined degree of similarity or correlation (e.g., whether the audio signals are the same or substantially the same or whether the audio signals correlate with one another). In response to a determination that the first and second information have the defined degree of similarity or correlation, at 508 the IMD and/or the external device can initiate a telemetry session with one another. In response to a determination that the first and second information fail to exhibit the defined degree of similarity or correlation, at 510 the IMD and/or the external device can forgo a telemetry session.

Figure 6:
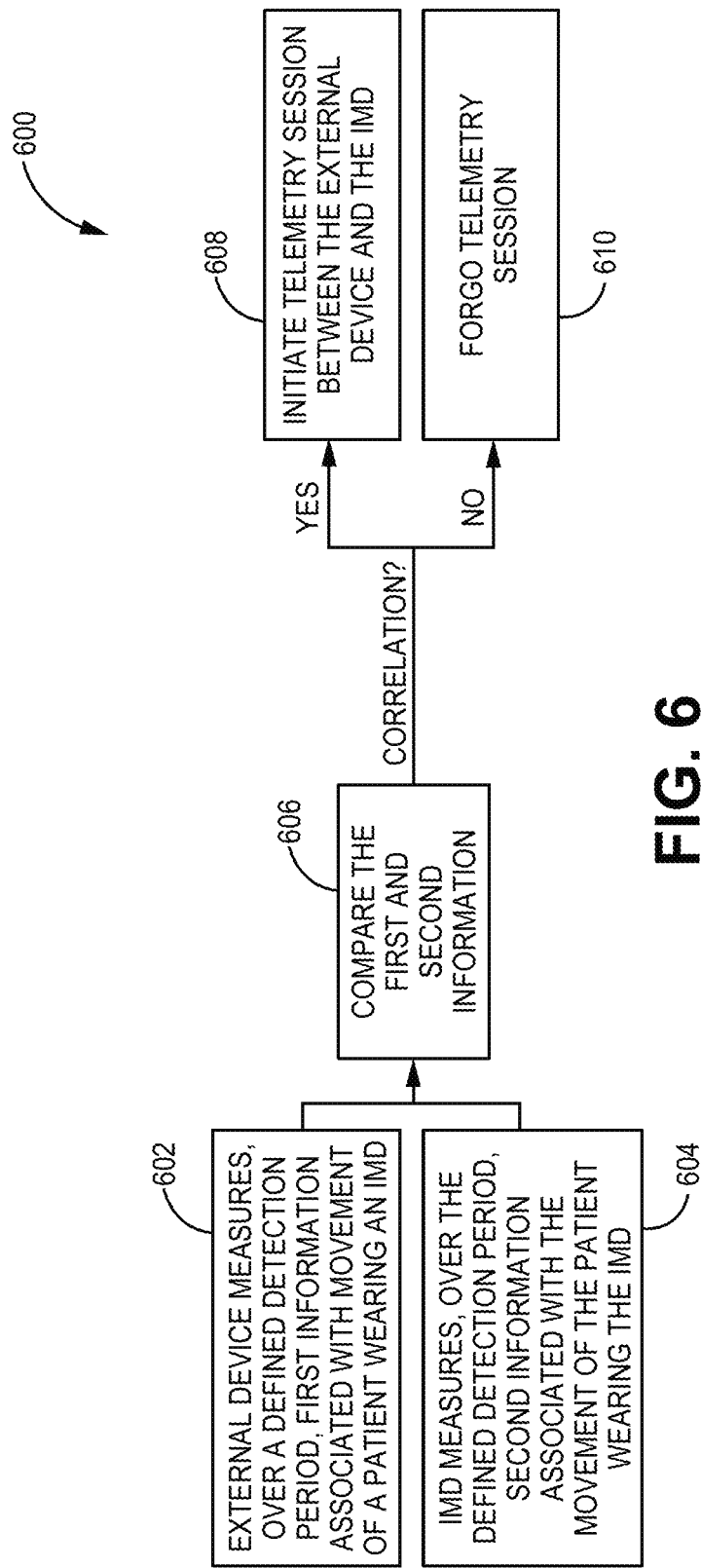
FIG. 6 illustrates a flow diagram of an example, non-limiting method of facilitating authorized telemetry with an IMD and an external device based on concurrent detection, by the IMD and the external device, of information associated with movement of a patient in which the IMD is implanted in accordance with one or more embodiments described herein.

FIG. 6 illustrates a flow diagram of an example, non-limiting method 600 facilitating authorized telemetry with an implantable device and an external device based on concurrent detection, by the IMD and the external device, of information associated with movement of a body of a patient in which the IMD is implanted in accordance with one or more embodiments described herein. Repetitive description of like elements employed in other embodiments described herein is omitted for sake of brevity.

At 602, an external device (e.g., external device 114), measures, over a defined detection period, first information associated with movement of the patient wearing the IMD. For example, the external device can detect and capture motion signals corresponding to motion performed by the body of the patient using one or more motion sensors at the external device (e.g., via an accelerometer or piezoelectric device). In some embodiments, the particular motion can vary from time to time as the external device requests to pair with the IMD.

At 604, the IMD measures, over the defined detection period, second information associated with the movement of the patient wearing the IMD. For example, the IMD can also detect and capture motion signals corresponding to the motion performed by the using one or more motions sensors of the IMD.

The external device can send the first information to the IMD or the IMD can send the second information to the external device. In some embodiments, in lieu of or in addition to the external device sending first information to the IMD or the IMD sending second information to the external device, a tertiary device can receive both the first information and the second information.

The device having the first or second information can compare the first and second information at 606. For example, the first and second information can be compared and analyzed to determine a degree of similarity or correlation between the first and second information. For example, the IMD or the external device can compare the respective motion signals captured by the respective devices. Based on the comparison, the IMD or the external device can determine whether the first and second information (e.g., the respective motion signals) exhibit a defined degree of similarity or correlation. In response to a determination that the first and second information have the defined degree of similarity or correlation, at 608 the IMD and/or the external device can initiate a telemetry session with one another. In response to a determination that the first and second information fail to exhibit the defined degree of similarity or correlation, at 610 the IMD and/or the external device can forgo a telemetry session.

With reference back to FIG. 1, a second group of embodiments of system 100 is described in connection with authorizing telemetry between the implantable device 104 and the external device 114 based on generation of a unique signal by the body in which the implantable device 104 is implanted. Similar to the first group of embodiments, the unique signal or signals can be based on a physiological state of the body 102 in which the implantable device 104 is implanted, a motion of the body 102 in which the implantable device 104 is implanted, and/or a sound made by the body 102 in which the implantable device 104 is implanted.

Unlike the first group of embodiments, the signals generated by on the body 102 in which the implantable device 104 is implanted may not be compared to concurrently detected corresponding signals by the external device 114. To the contrary, the signals can be compared to unique keys or passwords that are employed to determine whether to authorize and/or initiate a telemetry session between the implantable device 104 and the external device 114. In particular, the body 102 in which the implantable device 104 is implanted can select or be assigned a specific action to perform. The performance of the action can cause a signal to be generated. The signal can be associated with or described in terms of particular physiological actions, motion actions and/or sounds detectable by the implantable device 104. Reference information defining or identifying the particular physiological, motion and/or sound signals associated with the specific action can be stored in the memory of (or otherwise accessible by) the implantable device 104. In some embodiments, the implantable device 104 can access the reference information by accessing a database or repository of information stored at a location on a communication network to which the implantable device 104 can be communicatively coupled.

For example, in embodiments in which the implantable device 104 detects one or more physiological, motion, and/or sound signals in response to performance of a particular action by the body in which the implantable device 104 is implanted, the implantable device 104 can compare the detected signals with the reference information to determine whether the detected signals correspond to, or substantially correspond to, the reference information. In response to a determination that the detected signals correspond to the reference information, the implantable device 104 can identify a device associated with the reference information with which the implantable device 104 is configured to initiate or conduct a telemetry session. The implantable device 104 can initiate and/or conduct an authorized telemetry session with the external device 114.

In some embodiments, the implantable device 104 can also retrieve or access additional information associated with the reference information and/or the external device 114 that can be used by the implantable device 104 to initiate and/or establish the telemetry session with the external device 114. For example, this additional information can include, but is not limited to, an identifier for the external device 114, an access key, a session key, and/or protocol defining authorized data exchange between the implantable device 104 and the external device 114.

In an embodiment, the body in which the implantable device 104 is implanted can perform a physical action that is correlated to a specific physiological reaction of the body 102 in which the implantable device 104 is implanted (e.g., a rise in heart rate, a particular heart rate above a threshold heart rate or a particular ventilation rate). For example, the action can include jumping, sitting, running and/or squatting. According to this example, in response to a determination that the heart rate and/or change in heart rate corresponds to authorization data representative of a reference heart rate or a reference change in heart, the implantable device 104 can authorize and/or initiate a telemetry session with a device associated with the authorization data (e.g., the external device 114).

In another example, the action can include holding of breath by the body 102 in which the implantable device 104 is implanted for a defined duration of time. According to this example, the implantable device 104 can detect that the breath has been held for a defined duration of time. In response to a determination that signals associated with ventilation in the body 102 (e.g., no or low ventilation for a defined period of time) correspond to authorization data representative of reference ventilation data (e.g., no or low ventilation for the defined period of time), the implantable device 104 can authorize and/or initiate a telemetry session with a device associated with the authorization data (e.g., the external device 114).

In yet another embodiment, the body in which the implantable device 104 is implanted can generate a particular sound (e.g., a spoken word, a spoken phrase, a hum, a melody or a song) that is correlated to a specific audio signal pattern and/or vibration pattern detectable by the implantable device 104 (e.g., via one or more acoustic or vibration sensors). According to this embodiment, in response to a determination that the detected sound and/or vibration signal corresponds to authorization data representative of a reference sound and/or vibration signal (e.g., a sound wave pattern or a motion pattern), the implantable device 104 can authorize and/or initiate a telemetry session with a device (e.g., the external device 114) associated with the authorization data.

Still in yet another embodiment, the body in which the implantable device 104 is implanted can generate a combination of specific physiological, motion and/or audio signals based on a combination of physiological, motion and/or speech actions. For example, the body in which the implantable device 104 is implanted can perform an action that includes a jumping jack followed by speaking the words "activate my IMD." The implantable device 104 can be configured to detect the unique combination of physiological (e.g., rise in heart rate), motion (e.g., jumping jack motion), and audio signals (e.g., sound waves corresponding to the spoken words) associated with the action using various sensors and associated circuitry and compare the detected signal combination to reference authorization data corresponding to the signal combination. Similar to the embodiments described above, in response to a determination that a detected signal combination corresponds to authorization data representative of a reference signal combination, the implantable device 104 can authorize and/or initiate a telemetry session with a device (e.g., the external device 114) associated with the authorization data.

A third group of embodiments of system 100 is described in connection with authorizing telemetry between the implantable device 104 and the external device 114 based on a unique authentication signal that is generated by the external device 114 and detected by the implantable device 104 in embodiments in which the implantable device 104 is located within relatively close proximity to the external device 114. The unique authentication signal can embody a unique password or key provided by the external device 114 to authorize and/or establish a telemetry session between the implantable device 104 and the external device 114 (or between the implantable device 104 and another external device). For example, the unique authentication signal can correspond to a unique audio signal, a unique light signal, or a unique radio frequency (RF) signal. The external device 114 can generate the unique authentication signal based on information stored in memory of the external device 114, or accessible to the external device 114 via a network, that defines the unique authentication signal and/or provides computer readable instructions regarding how to command hardware of (or a component accessible to) the external device 114 to generate the unique authentication signal.

The implantable device 104 is configured to detect the unique authentication signal and compare it to reference authentication information that can identify the unique authentication signal. The reference authentication information can be stored in memory of the implantable device 104 or accessible to the implantable device 104 via a network. In response to a determination that the detected authentication signal corresponds to, or substantially corresponds to, the reference authentication information, the implantable device 104 can authorize and/or initiate a telemetry session between the implantable device 104 and the external device 114 (or between the implantable device 104 and another external device). Likewise, in response to a determination that the detected authentication signal fails to correspond to, or substantially correspond to, the reference authentication information, the implantable device 104 can forgo a telemetry session between the implantable device 104 and the external device 114 (or between the implantable device 104 and the external device 114).

In an embodiment, the unique authentication signal used to facilitate authorizing a telemetry session with the implantable device 104 includes a unique audio signal generated by the external device 114. For example, the unique audio signal can include an audio signal indicative of a ringtone, a song, a melody, a recorded voice, etc. For instance, a user of the external device 114 (or the external device itself 114) can select, designate or otherwise be assigned a unique audio signal that serves as key to gain access to an implantable device 104. The external device 114 can also store a unique audio signal selected by the user of the external device 114.

In this embodiment, the external device 114 can include a speaker and/or an audio player configured to emit the unique audio signal. In embodiments in which the implantable device 104 is located within relatively close proximity to the external device 114 (e.g., within range to detect an audible signal from the external device 114), the implantable device 104 can detect the unique audio signal using one or more analog or digital acoustic sensors (e.g., a microphone). The implantable device 104 can compare the detected audio signal to reference information defining one or more characteristics of a reference audio authentication signal (e.g., a reference audio fingerprint or a reference waveform). The reference information can be stored in memory of the implantable device 104 or accessible to the implantable device 104 via a network. The implantable device 104 is further configured to determine a degree of similarity between the detected audio signal and the reference information. In response to a determination that the detected audio signal has a defined degree of similarity to the reference information, the implantable device 104 can authorize a telemetry session with the external device 114 (or another external device).

In another embodiment, the unique authentication signal used to facilitate authorizing a telemetry session with an implantable device 104 includes a unique light signal generated by the external device 114. For example, the unique light signal can include or be light of a specific wavelength. In another example, the specific light signal can correspond to a light pattern that includes two or more variations in light behaviors or characteristics over a defined duration of time. These light behaviors or characteristics can include, but are not limited to, light on and light off patterns (e.g., pulsation) and light intensity. For example, a unique light pattern can include a combination of successive permutations of light on- and light off-patterns. The durations of time that the light is on or off in association with the light pulsation pattern can change or vary and/or can change from time to time to create a number of possibilities for unique light patterns. In addition to a unique pulsation pattern, a unique light pattern can also include variances in light color/wavelength and/or intensity for different light signals.

A unique light signal can also include overlapping or simultaneous emission of two or more light colors. For example, the external device 114 can include a light emitting diode (LED) panel that includes a plurality of LEDs, such as an LED panel associated with a display screen of the external device 114. The external device 114 can further cause the LEDs to emit different light colors at the same time or at different times in accordance with a unique light pattern.

In this embodiment, the external device 114 can include a light source configured to generate the unique light signal corresponding to a unique authentication signal (e.g., one or more LEDs, an LED panel or one or more organic LEDs). For example, in embodiments in which the external device 114 is a smart phone or tablet that includes a display screen and/or a camera with an apparatus configured to emit a flash, the display screen and/or light source can be employed to provide the light signal of the external device 114.

In some embodiments, the implantable device 104 can include one or more photodiodes configured to detect and/or interpret the unique light signal. In an embodiment, during generation of the unique light signal, the light source of the external device 114 can be placed against or in close proximity to the area of the body 102 in which the implantable device 104 is located to facilitate detection of the light signal by the implantable device 104. In another embodiment, the light source of the external device 114 can be aimed towards the implantable device 104 while being distanced away from the body 102 within a maximum detectable distance range (e.g., about 1.0 meter) from the body 102.

The implantable device 104 can compare the detected light signal to reference information defining one or more characteristics of a reference light authentication signal stored in memory of the implantable device 104 or accessible to the implantable device via a network. The implantable device 104 can further determine a degree of similarity between the detected light signal and the reference light authentication signal. In response to a determination that the detected light signal has a defined degree of similarity with the reference light authentication signal, the implantable device 104 can authorize a telemetry session with the external device 114 (or between the implantable device 104 and another external device). In response to a determination that the detected light signal fails to have the defined degree of similarity with the reference light authentication signal, the implantable device 104 can forgo a telemetry session with the external device 114 (or between the implantable device 104 and another external device).

In another embodiment, the unique authentication signal used to facilitate authorizing a telemetry session with the implantable device 104 includes a unique RF signal, such as an RF burst, generated by the external device 114. RF is a rate of oscillation in the range of around 3 kHz to 300 GHz. RF currents applied to the body 102 do not cause the painful sensation of electric shock as do lower frequency currents. A unique RF signal can correspond to a signature RF pattern that is defined by one or more variable RF signal components including, but not limited to, frequency, bandwidth, signal duration, and/or modulation. For example, a unique RF signal can include a unique pulsed RF waveform or series of waveforms characterized by a particular pulse width or variation in pulse width. In another example, a unique RF signal can include a particular bandwidth or variation in bandwidth over a defined emission period (typically hundreds of microseconds to a few milliseconds long). The unique RF signal can further include characteristics that are distinguishable by the implantable device 104 from RF signals carrying information.

According to this embodiment, the external device 114 can include an RF transmitter and associated circuitry to generate the unique RF signal. Likewise, the implantable device 104 can include an RF receiver and associated circuitry configured to receive and process the RF signal to identify distinguishing characteristics of the RF signal (e.g., a signature pattern in the RF signal). The implantable device 104 can further compare the detected RF authentication signal to information defining characteristics of a reference RF authentication signal and determine a degree of similarity between the detected RF authentication signal and the reference RF authentication signal. In response to a determination that the respective signals exhibit a threshold degree of similarity, the implantable device 104 can authorize telemetry between the implantable device 104 and the external device 114 (or another external device). In response to a determination that the respective signals fail to exhibit a threshold degree of similarity, the implantable device 104 can forgo authorization of telemetry between the implantable device 104 and the external device 114 (or another external device).

In another embodiment, the unique signal can include human tapping of a unique tapping pattern applied to the body 102 in which the implantable device 104 is implanted. According to this embodiment, the implantable device 104 can employ one or more sensors to detect the tapping pattern on the body 102. The implantable device 104 can further compare the tapping pattern with a reference motion or vibration pattern. The implantable device 104 can authorize and/or initiate a telemetry session with the external device 114 in response to a determination that the detected tapping pattern has a defined degree of similarity with the reference pattern.

In various embodiments, aside from employing a unique RF transmission as a password or secret key that is used by the implantable device 104 to authorize telemetry between the implantable device 104 and the external device 114 (or another device), external device 114 can use a distinguishing RF transmission to activate a "pairing mode" of implantable device 104. For example, rather than performing continuous or continual detecting in association with receiving and interpreting a unique authentication signal (e.g., a unique motion-based signal, a unique audio signal, a unique light signal or a unique RF signal), that is used by the implantable device 104 to authorize a telemetry session, the implantable device can be configured to perform the appropriate detecting when in a pairing mode. According to this example, the implantable device 104 can enter pairing mode in response to a particular trigger signal and activate the sensors of the implantable device 104, sensory circuitry and/or detection device. The implantable device 104 can further be configured to remain in pairing mode for a defined window of time and/or until a unique authorization signal is detected.

In one embodiment, the trigger signal that causes the implantable device 104 to enter pairing mode is a distinguishable RF signal. For example, the external device 114 can transmit an RF signal of a specific frequency or duration (e.g., non-commercial frequency such as 400 Megahertz (MHz)) that serves as a pairing mode activation signal. The implantable device 104 can be further configured to detect, such as via an RF antenna, and interpret the pairing mode activation signal. In response to detection of the pairing mode activation signal, the implantable device 104 can enter pairing mode. For example, activation of pairing mode can include the activation of commercial RF signal detection by the antenna and associated circuitry or another antenna and associated circuitry of the implantable device 104.

A fourth group of embodiments of system 100 is described in connection with authorizing telemetry between the implantable device 104 and the external device 114 based on security information, received or captured at the external device 114 and transmitted to the implantable device 104. Similar to the second and third groups of embodiments, the security information can embody a unique password or key that can be provided by the external device 114 to the implantable device 104 to authorize and establish a telemetry session between the implantable device 104 and the external device 114 (or between the implantable device 104 and another external device).

In one embodiment, the security information can include image data of a unique physical feature of the body 102 in which the implantable device 104 is located. For example, using a camera or scanner of the external device 114, the external device 114 can capture biometric image data of the body 102 in which the implantable device 104 is located. This biometric image data can include, but is not limited to, information representative of image data of the face associated with the body 102, information representative of an iris of an eye of the body 102, and/or information representative of a fingerprint associated with the body 102. In another example, the image data can include information representative of a unique tattoo on the skin of the body 102. In another example, the image data can include information representative of a particular part of the body 102 (e.g., foot or palm). In another example, the image data can include information representative of a particular hand symbol (e.g., a peace sign or a sign language symbol).

After or during reception of the image data, the implantable device 104 can compare the received image data to reference image data stored in memory of the implantable device 104 or accessible to the implantable device 104 via a network. In response to a determination that the received image data corresponds to, or substantially corresponds to, the reference image data, the implantable device 104 can authorize and/or establish a telemetry session with the external device 114 (or between the implantable device 104 and another external device).

In some embodiments, the external device 114 can be configured to attach a time stamp to the captured image data corresponding to the time when the image data was captured. The implantable device 104 can further be configured to authorize and/or establish a telemetry session with the external device 114 (or another external device) in response to a determination of correspondence between the received image data and the reference image data, and in response to the time stamp associated with the image data being within a defined window of time (e.g., within the past one minute, within the past five minutes or within the past 10 minutes) relative to the point in time at which the image data was received by the implantable device 104. By restricting telemetry authorization to image data associated with a recent time stamp, system 100 can minimize the ability for a hijacking external device to re-use outdated image data, thus adding an element of security to system 100.

In another embodiment, security information can include security data (e.g., unique identifier) captured by the implantable device 104 from a microchip implanted within the body 102 in which the implantable device 104 is located. According to this embodiment, the external device 114 can include a scanner configured to read the security data from the microchip when the external device 114 is located within close proximity to the implanted microchip. The external device 114 can further provide the security data to the implantable device 104. In response to reception of the security data, the implantable device 104 can compare the security data to reference security data stored in the memory of the implantable device 104 or accessible to the implantable device 104 via a network. In response to a determination that the received security data corresponds to, or substantially corresponds to, the reference security data, the implantable device 104 can authorize and/or establish a telemetry session with the external device 114 (or another external device).

Still in yet another embodiment, the security information can include a password input to the external device 114. In some embodiments, the password can be input by the user of the external device 114 (e.g., via a keypad, touch screen or a voice detection device). In some embodiments, the password can be or be included in electronic information received at the external device 114 from another external device over a wired or wireless communication channel.

According to these embodiments, the external device 114 can provide the password to the implantable device 104 and the implantable device 104 can compare the password to a reference password stored in memory of the implantable device 104 or accessible to the implantable device 104 via a network. In response to a determination that the received password corresponds to, or substantially corresponds to, the reference password, the implantable device 104 can authorize and/or establish a telemetry session with the external device 114 (or between the implantable device 104 and another external device).

Figure 7:
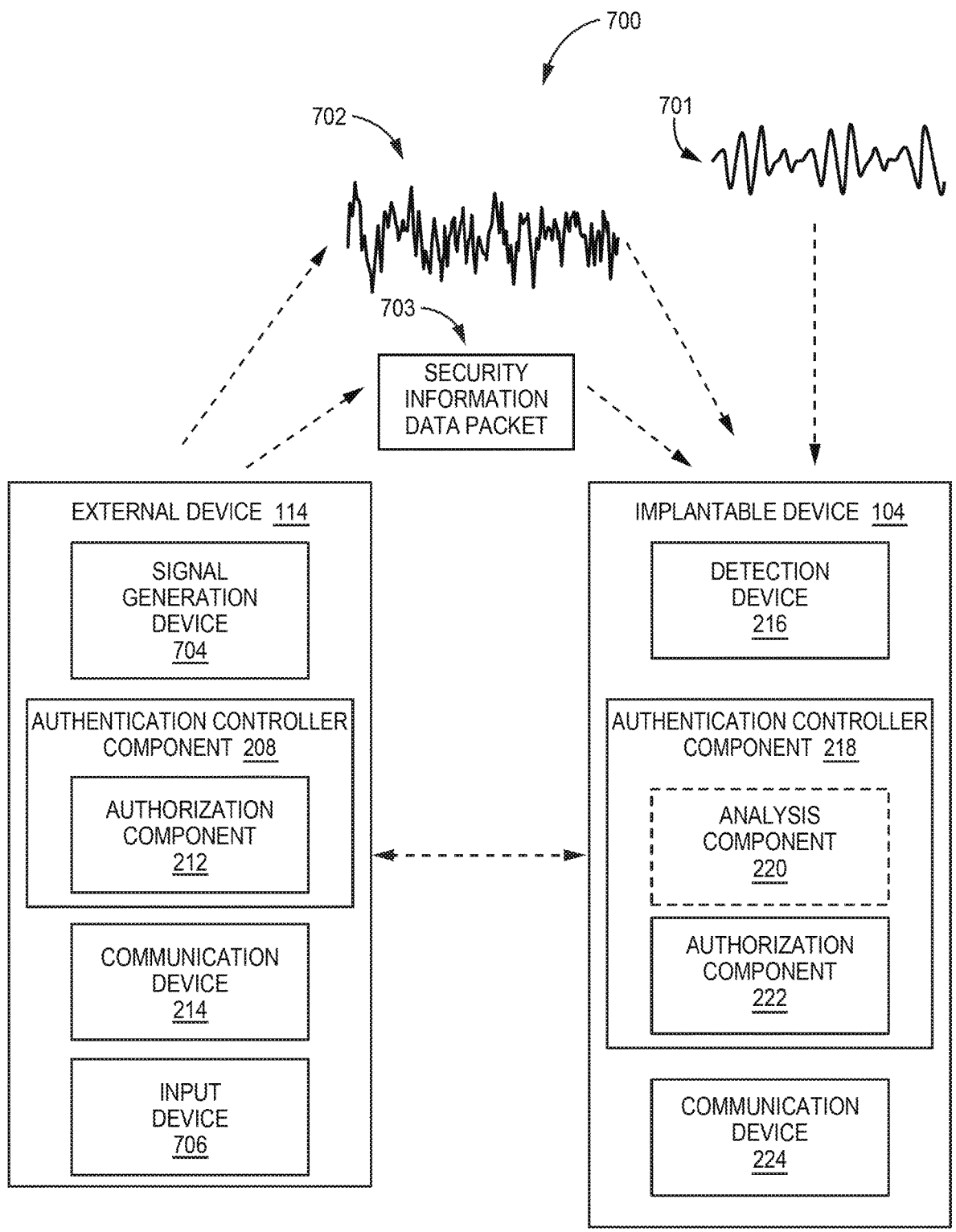
FIG. 7 illustrates a block diagram of a non-limiting system facilitating authorized telemetry with an implantable device based on comparison of a signal or security information, received by the implantable device, to reference information corresponding to the signal or the security information in accordance with one or more embodiments described herein.

FIG. 7 illustrates a block diagram of a non-limiting system 700 facilitating authorized telemetry with an implantable device based on comparison of a signal or security information, received by the implantable device, to reference information corresponding to the signal or security information in accordance with the second, third and fourth groups of embodiments of system 100. Although not shown, it is to be appreciated that the implantable device 104 is implanted within a body of a living being. For exemplary purposes, system 700 is described with the assumption that the implantable device 104 is implanted within a human being. In other embodiments, the implantable device 104 can be implanted within any other living being, such as an animal, for example.

Similar to system 100 and system 200, system 700 includes external device 114 and implantable device 104. In accordance with system 700, the external device 114 and the implantable device 104 can include one or more of the same or similar components as previously described with respect to system 200 and/or system 100. However, in various embodiments, as described below, one or more of signal 701 can be utilized in system 700, signal 702 can be utilized in system 700 and/or security information data packet 703 can be utilized in system 700.

In various implementations associated with system 700 and the second, third and fourth groups of embodiments, these components can include one or more of the structures, features and/or functionalities previously described. Repetitive description of like elements employed in other embodiments described herein is omitted for sake of brevity. In some implementations associated with system 700 and the second, third and fourth groups of embodiments of system 100, various components can include alternative or additional structures, features, and functionalities, which are described infra where applicable in association with the following description of system 700.

System 700 depicts implantable device 104 receiving one or more signals and/or information, including signal 701, signal 702 and security information data packet 703. Signal 701 is or includes a unique signal transmitted from the external device 114 to the implantable device 104 to facilitate authorization of telemetry, by the implantable device 104, between the implantable device and the external device (or between the implantable device 104 and another external device). Signal 702 can include the unique signal described with reference to the second group of embodiments for FIG. 1. For example, in some embodiments, signal 701 can be based on a physiological state/function of the body 102 in which the implantable device 104 is located, a motion of the body 102 in which the implantable device 104 is located, and/or a sound made by the body in which the implantable device 104 is implanted. In some embodiments, signal 701 can be based a combination of two or more of: a physiological state/function of the body 102 in which the implantable device 104 is located, a motion of the body 102 in which the implantable device 104 is located, and/or a sound made by the body in which the implantable device 104 is implanted.

Detection device 216 of the implantable device 104 can employ one or more of the sensors, devices, and/or associated circuitry previously described to detect and/or process signal 701. In this embodiment, signal 701 can correspond to a unique key or password that is employed to authorize and/or initiate a telemetry session between the implantable device 104 and the external device 114.

Analysis component 220 is configured to compare signal 701 with reference information defining or corresponding to the particular physiological, motion and/or sound signals associated with authorization of telemetry between the implantable device 104 and the external device 114 (or another external device). The analysis component 220 can determine whether the signal 701 and/or data generated based on the signal 701 has a defined degree of similarity with the reference information. In an embodiment, the reference information can be stored by the implantable device 104 in memory. In other embodiments, the implantable device 104 can access the reference information by accessing a database or repository of information stored at a location on a communication network to which the implantable device 104 can be communicatively coupled. In some embodiments, the reference information can further be associated with information identifying the external device 114 as the device with which the implantable device 104 is configured to initiate a telemetry session in response to the determination that the signal 701 has a defined degree of similarity with the reference information.

In response to a determination that signal 701 exhibits a defined degree of similarity with the reference information, authorization component 222 can initiate (or, in some embodiments, continue) telemetry with external device 114 (or with another external device). In some embodiments, authorization component 222 can access or utilize additional information (e.g., access key, session key or protocol defining authorized data exchange) associated with the reference information to facilitate initiating and/or establishing the telemetry session with the external device 114 (or the other external device).

As described above with reference to systems 100, 700 and/or the second group of embodiments, the authentication controller component 208 can facilitate various operations of external device 114 in connection with facilitating an authorized telemetry session between external device 114 and implantable device 104 (or another external device). For example, authentication controller component 208 can notify the implantable device 104 that the external device 114 (or another device) would like to establish a telemetry session with the implantable device 104, activate detection device 216 to monitor for receipt of signal 701 and/or generate or send (e.g., via communication device 224) an acknowledgment message to the external device 114 indicating that the implantable device 104 has activated the detection device 216 and awaiting receipt of signal 701.

In an embodiment, in response to reception of the acknowledgement message, the authentication controller component 208 can generate notification at the external device 114 of an identification of, and/or timing for, a particular action (e.g., movement or speech) requested to be performed and transmitted to the implantable device 104 via the signal 701.

While signal 701 is generated at the external device 114 based on one or more of a physiological state/function of the body 102 in which the implantable device 104 is located, a motion of the body 102 in which the implantable device 104 is located, and/or a sound made by the body in which the implantable device 104 is implanted, signal 702 is or includes a unique signal based on a unique authentication signal generated by the external device 114.

In these embodiments, signal 702 is associated with implementation of system 700 in accordance with the third group of embodiments of system 100. As previously described, the third group of embodiments of system 100 facilitate authorizing telemetry between the implantable device 104 and the external device 114 based on the unique authentication signal. By way of example, but not limitation, signal 702 can correspond to a unique audio signal, a unique light signal, a RF signal and/or a unique password or key generated by the external device 114 via signal generation device 704.

Signal generation device 704 can include hardware, software, or a combination of hardware and software to facilitate generating signal 702. For example, signal generation device 704 can include a speaker and/or an audio player configured to generate and/or emit the unique audio signal. In another example, signal generation device 704 can include or employ one or more light sources (e.g., an LED or an LED panel). Signal generation device 704 can include an RF transmitter or transceiver and associated circuitry to generate the unique RF signal. In some embodiments, the communication device 214 and the signal generation device 704 can share the same RF transmitter or transceiver.

Detection device 216 can include hardware, software, or a combination of hardware and software configured to process a signal as previously described with reference to FIG. 2. By way of example, but not limitation, detection device 216 can include one or more motion sensors (e.g., an accelerometer, a piezoelectric device or a pressure sensor) to detect vibration associated with a unique audio signal and/or an RF receiver or transceiver configured to receive and/or process unique RF signals.

Analysis component 220 is configured to compare detected signal 702 to reference information stored at the memory of the implantable device 104 or otherwise accessible to the implantable device 104 over a network. The reference information can vary depending on the type of information included in signal 702. For example, in embodiments in which the signal 702 includes a unique audio signal, the reference information can include a set of defined audio parameters, a defined reference audio fingerprint or a defined set of motion parameters associated with the vocal cords of the particular, expected producer of the audio signal.

Analysis component 220 is configured to compare the signal 702, or electronic information corresponding to signal 702, to the reference information stored in the memory of the implantable device 104 or accessible to the implantable device 104 via a network. In response to a determination that signal 702 exhibits a defined degree of correspondence to the reference information, authorization component 222 can initiate telemetry with external device 114 (or another external device).

Security information data packet 703 includes security information received or captured at the external device 114, and/or transmitted to the implantable device 104 to facilitate authorization of telemetry between the implantable device 104 and the external device 114. Security information data packet 703 can include the various types of security information described for the fourth group of embodiments of system 100 described with reference to FIG. 1. For example, security information data packet 703 can include biometric data (e.g., an image of an eye iris, a body part, a distinguishing tattoo or a fingerprint). In another example, security information data packet 703 can include a password or key (e.g., a password or key received at the external device 114 as input to the external device 114 by the user of the external device 114).

In various embodiments, external device 114 can include an input device 706 configured to receive user input in association with receiving the information corresponding to the security information data packet 703. For example, input device 706 can include a keypad, a touch screen, or a voice detection device. In some embodiments, the input device 706 can include a camera or scanner configured to capture image data. In some embodiments, the input device 706 can include a graphical user interface configured to display information and/or otherwise output information from the external device 114.

The external device 114 is configured to provide security information data packet 703 to the implantable device 104 (e.g., using communication device 214). Upon reception of the security information data packet 703 (e.g., via communication device 224), analysis component 220 is configured to compare the data included in the security information data packet 703 with reference information, as previously described in association with FIG. 1. In response to a determination that the security information data packet 703 corresponds to, or substantially corresponds to, the reference information, the authorization component 222 is configured to authorize and facilitate telemetry between the implantable device 104 and the external device 114 (or between the implantable device 104 and another external device).

FIGS. 8, 9, 10, 11 and 12 illustrate flow diagrams of example, non-limiting methods for facilitating authorized telemetry with an implantable device based on comparison of a signal or security information, received by the IMD, to reference information corresponding to the signal or security information in accordance with the second, third and fourth groups embodiments described herein. The methods of FIGS. 8, 9, 10, 11 and 12 are described with reference to FIGS. 1 and 7 wherein the implantable device (e.g., implantable device 104) is embodied in the respective methods as an IMD. Repetitive description of like elements employed in other embodiments described herein is omitted for sake of brevity.

Figure 8:
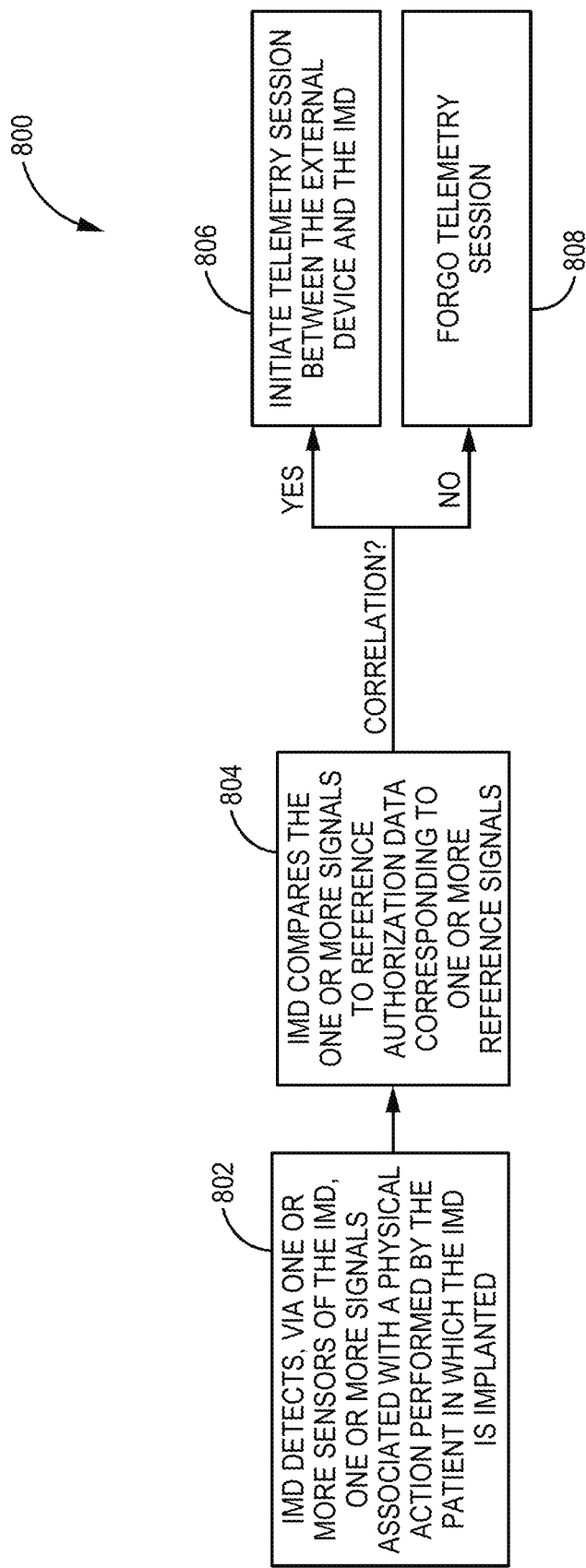
FIG. 8 illustrates a flow diagram of an example, non-limiting method of facilitating authorized telemetry with an implantable device and an external device based on detection, by the implantable device, of information associated with a physiological state of a patient in which the implantable device is implanted in accordance with one or more embodiments described herein.

FIG. 8 illustrates a flow diagram of an example, non-limiting method 800 facilitating authorized telemetry with an implantable device and an external device based on detection, by the IMD, of information associated with a physical action performed by the body of the patient in which the IMD is implanted in accordance with the second group of embodiments described herein.

With reference to FIGS. 1, 2, 7 and/or 8, at 802, an IMD detects, via one or more sensors of the IMD (or via detection device 216), one or more signals associated with a physical action performed by the patient in which the IMD is implanted (e.g., a physical action performed by or via body 102). For example, the patient can perform a specific physical action known to the patient as corresponding to a "password" or "code" associated with initiating and/or conducting an authorized telemetry session between the IMD and a particular external device (e.g., external device 114). For example, the patient can take a deep breath while stretching one or more arms above the head of the patient.

At 804, the IMD compares the one or more detected signals to reference authorization data corresponding to one or more reference signals to determine a degree of similarity or correlation between detected signals and the reference signals (e.g., via the analysis component 220). In some embodiments, the reference authorization data is or includes the reference information described herein with reference to FIG. 7, for example.

In some embodiments, the reference authorization data can be previously-stored in the IMD or accessed by the IMD (e.g., via a network), and can be information indicative of the physical action. This information can include information representative of one or more reference physiological, motion, and/or audio signals associated with the physical action.

In response to a determination that the detected signals have a defined degree of correlation with the reference signals, at 806 the IMD can initiate a telemetry session with the external device (e.g., via the authorization component 222). In response to a determination that the detected signals fail to exhibit the defined degree of correlation with the reference signals, at 810 the IMD can forgo a telemetry session with the external device.

Figure 9:
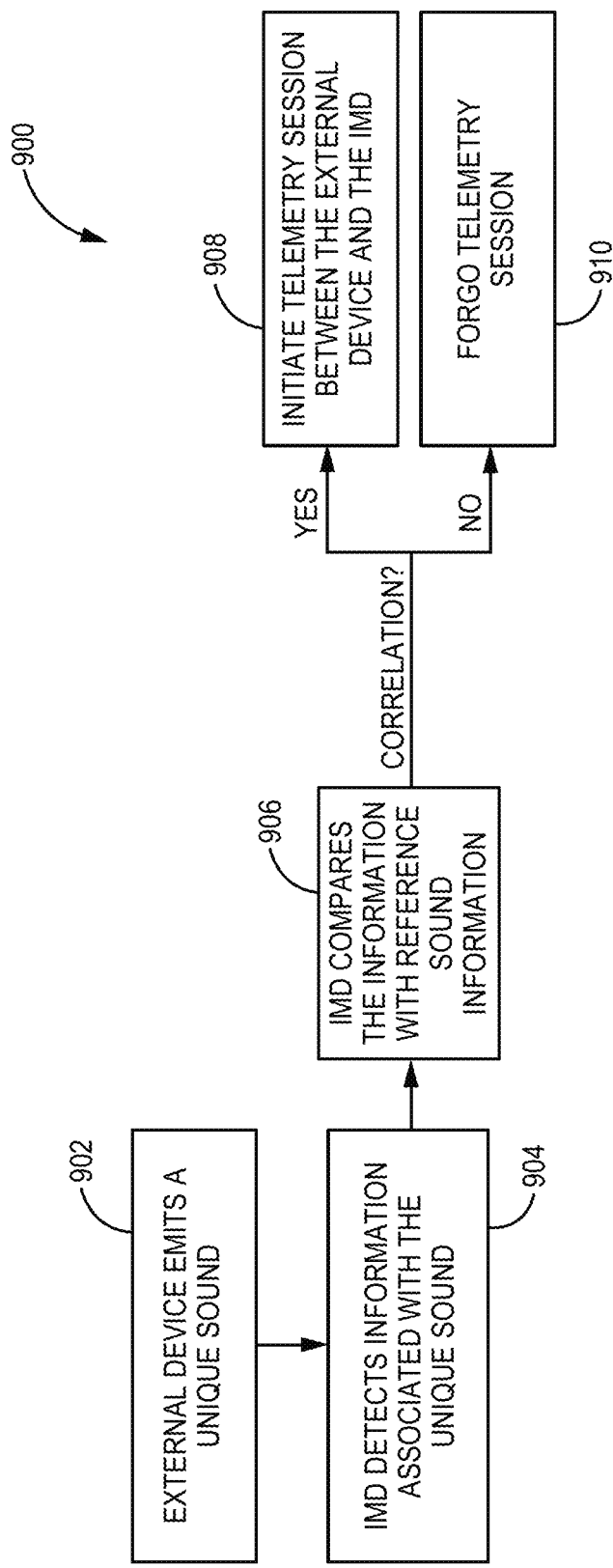
FIG. 9 illustrates a flow diagram of an example, non-limiting method of facilitating authorized telemetry with an implantable device and an external device based on a unique sound emitted by the external device in accordance with one or more embodiments described herein.

FIG. 9 illustrates a flow diagram of an example, non-limiting method 900 of facilitating authorized telemetry with an IMD and an external device based on a unique sound emitted by the external device in accordance with one or more embodiments described herein.

With reference to FIGS. 1, 2, 7 and/or 9, at 902, an external device (e.g., external device 114) emits a unique sound (e.g., via signal generation device 704). For example, the unique sound can include a unique ringtone or an original song. At 904, the IMD detects information associated with the unique sound (e.g., via detection device 216). For example, the IMD can detect characteristics associated with a waveform for the unique sound and/or determine an audio fingerprint for the unique sound. At 906, the IMD compares the information with reference sound information (e.g., via analysis component 220). For example, the IMD can compare measurements of frequency, amplitude, phase shift and/or an audio fingerprint of the unique sound with reference sound information defining reference measurement data and/or a reference audio fingerprint.

In response to a determination that the detected information has a defined degree of correlation with the reference sound information, at 908, the IMD can initiate a telemetry session with the external device (e.g., via authorization component 222). In response to a determination that the detected information fails to exhibit the defined degree of correlation with the reference sound information, at 910 the IMD can forgo a telemetry session with the external device.

Figure 10:
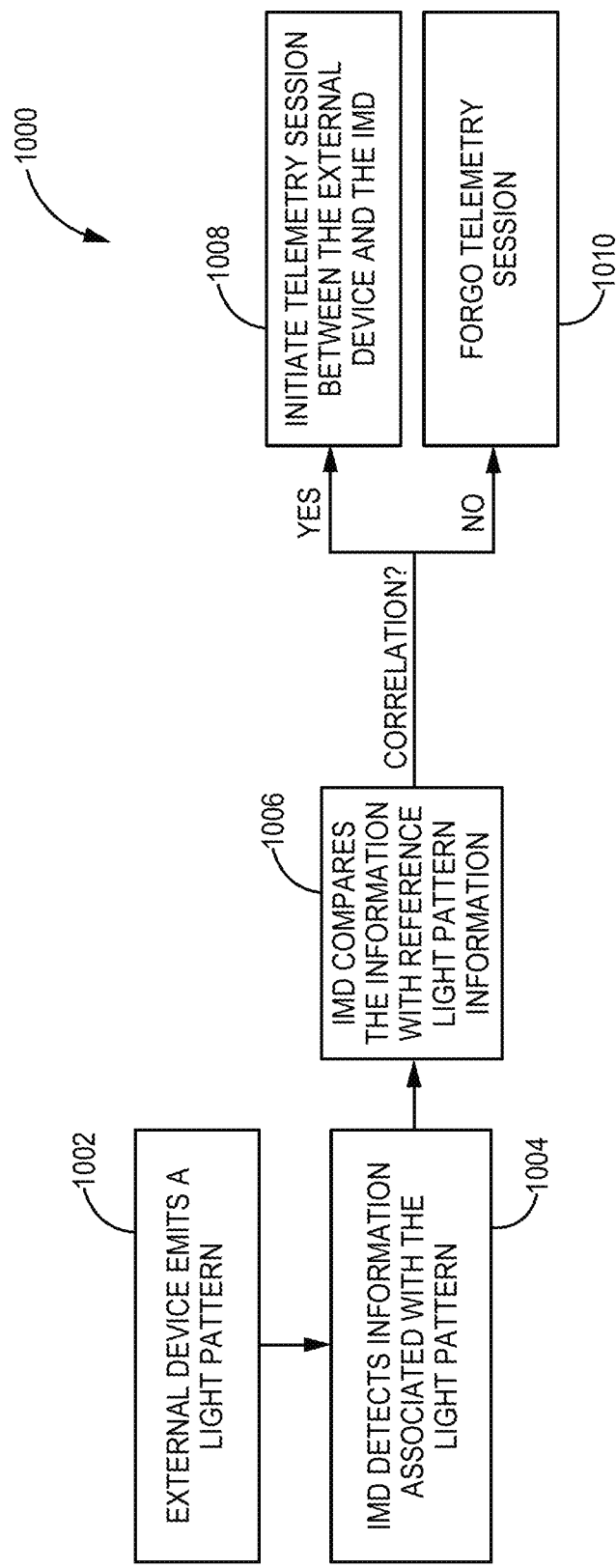
FIG. 10 illustrates a flow diagram of an example, non-limiting method of facilitating authorized telemetry with an implantable device and an external device based on a light pattern emitted by the external device in accordance with one or more embodiments described herein.

FIG. 10 illustrates a flow diagram of an example, non-limiting method 1000 of facilitating authorized telemetry with an IMD and an external device based on a light pattern emitted by the external device in accordance with one or more embodiments described herein.

With reference to FIGS. 1, 2, 7 and/or 10, at 1002, an external device (e.g., external device 114) emits a unique light pattern (e.g., via signal generation device 704). For example, the unique light pattern can include a sequence of light-on and light-off pulses with additional variation in color and/or intensity. At 1004, the IMD detects information associated with the unique light pattern (e.g., via detection device 216). At 1006, the IMD compares information associated with the light pattern with reference light information (e.g., via analysis component 220). In response to a determination that the detected information has a defined degree of correlation with the reference light information, at 1008, the IMD can initiate a telemetry session with the external device (e.g., via authorization component 222). In response to a determination that the detected information fails to exhibit the defined degree of similarity or correlation with the reference light information, at 1010 the IMD can forgo a telemetry session with the external device.

Figure 11:
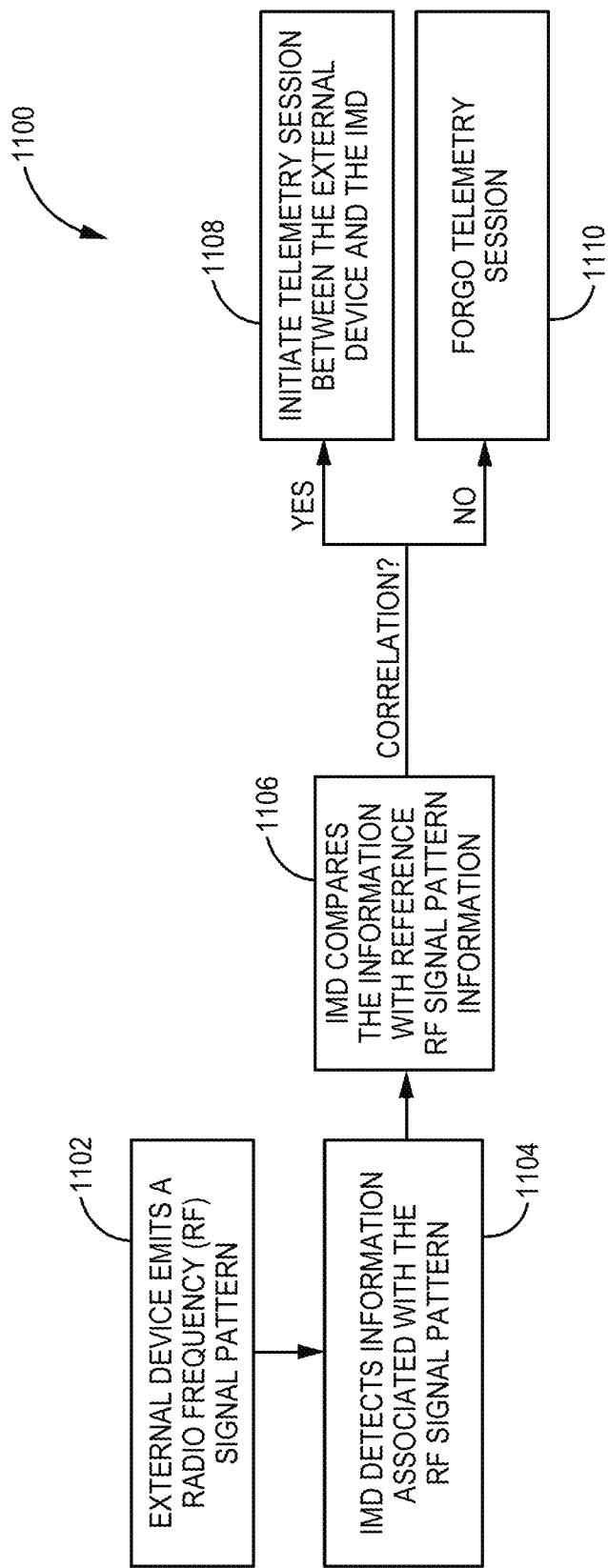
FIG. 11 illustrates a flow diagram of an example, non-limiting method of facilitating authorized telemetry with an implantable device and an external device based on a radio frequency signal pattern emitted by the external device in accordance with one or more embodiments described herein.

FIG. 11 illustrates a flow diagram of an example, non-limiting method 1100 of facilitating authorized telemetry with an IMD and an external device based on an RF pattern emitted by the external device in accordance with one or more embodiments described herein.

With reference to FIGS. 1, 2 and/or 11, at 1102, an external device (e.g., external device 114) emits a unique RF signal pattern (e.g., via signal generation device 704). For example, the unique RF signal pattern can include an RF signal having defined variations in frequency and/or bandwidth. At 1104, the IMD detects information associated with the unique RF signal pattern (e.g., via detection device 216). At 1106, the IMD compares the information with reference RF signal pattern information (e.g., via analysis component 220). In response to a determination that the detected information has a defined degree of correlation with the reference RF signal pattern information, at 1008, the IMD can initiate a telemetry session with the external device (e.g., via authorization component 222). In response to a determination that the detected information fails to exhibit the defined degree of similarity or correlation with the reference RF signal information, at 1110 the IMD can forgo a telemetry session with the external device.

Figure 12:
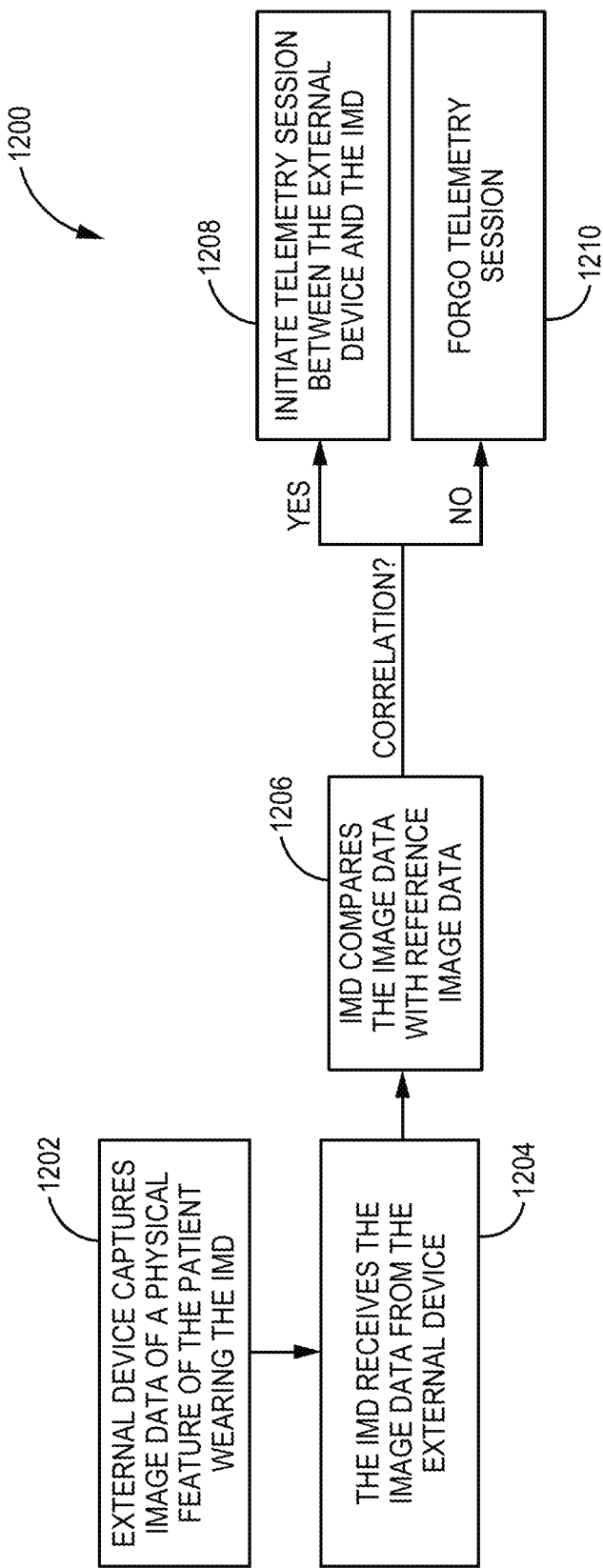
FIG. 12 illustrates a flow diagram of an example, non-limiting method of facilitating authorized telemetry with an implantable device and an external device based on image data of a physical feature of a patient in which the implantable device is implanted in accordance with one or more embodiments described herein.

FIG. 12 illustrates a flow diagram of an example, non-limiting method of facilitating authorized telemetry with an IMD and an external device based on image data of a physical feature of the body of the patient in which the IMD is implanted in accordance with one or more embodiments described herein.

With reference to FIGS. 1, 2, and/or 12, at 1202, an external device (e.g., external device 114) captures image data of a physical feature of the patient wearing the IMD (e.g., via input device 706). For example, using a camera on the external device, the user of the external device can take a picture of the face of the patient wearing the IMD. The image data can further include a time stamp indicating the time at which the image data was taken. At 1204, the IMD receives the image data from the external device (e.g., via communication device 214). At 1206, the IMD compares the image data with reference image data (e.g., via analysis component 220). For example, the IMD can perform facial recognition to identify unique features of the face and compare the unique features with reference image data identifying a set of reference facial features. At 1208, in response to a determination that the image data has a defined degree of correlation with the reference image data, the IMD can initiate a telemetry session with the external device (e.g., via authorization component 222). In response to a determination that the image data fails to exhibit the defined degree of correlation with the reference image data, at 1210 the IMD can forgo a telemetry session with the external device.

Referring now to FIG. 13, illustrated is a schematic diagram of another example, non-limiting medical device telemetry system 1300 facilitating authorized telemetry with an implantable device in accordance with one or more embodiments described herein. System 1300 includes one or more of the various structure, features and/or functionalities of system 100 with the addition of a second external device 1302. Repetitive description of like elements employed in other embodiments described herein is omitted for sake of brevity.

In accordance with one or more embodiments of system 1300, the implantable device 104, external device 114, and/or second external device 1302 can be configured to communicate with one another using any number of a variety of networks (not shown) and/or wireless communication protocols. For example, in one or more embodiments, the devices of system 1300 can communicate using NFC, or another type of communication protocol over a PAN or a LAN (e.g., a Wi-Fi network) that can provide for communication over greater distances than NFC protocol or that can provide various advantages (such as increased security). Other communication protocols that can be employed by system 1300 can include, but are not limited to, BLU- ETOOTH® technology-based protocols (e.g., BTLE protocol), UWB standard protocols, RF communication protocols, and/or other proprietary and non-proprietary communication protocols. In another embodiment, the devices of system 1300 can communicate with one another (and/or another device) over a WAN using cellular or HTTP based communication protocols (e.g., SIP).

Second external device 1302 can include one or more of the various structures, features and/or functionalities of external device 114. Second external device 1302 can also include, but is not limited to, a handheld computing device, a wearable computing device, a mobile phone, a smart phone, a tablet PC, PDA, a laptop computer, and/or a desktop.

Many of the various embodiments associated with facilitating telemetry with an implantable device 104 described supra note that the authentication/authorization process between the external device 114 and the implantable device 104 can facilitate telemetry between the implantable device 104 and the external device 114 or between the implantable device 104 and another device. In one or more embodiments, the second external device 1302 can be the other device with which telemetry with the implantable device 104 can be facilitated.

For example, with reference to FIGS. 1, 2 and/or 13, in accordance with system 1300, the external device 114 and/or the implantable device 104 can detect and compare concurrently detected signals (e.g., signals 202 and 204). In one embodiment, based on correspondence between these signals detected by the external device 114 and the implantable device 104, the implantable device 104 can authorize and/or initiate a telemetry session with the second external device 1302.

In another example, in any of the embodiments described herein, in lieu of or in addition to the IMD performing analysis of the signal transmitted from the external device 114, the second external device 1302 can perform analysis of the signal transmitted from the external device 114. By way of example, but not limitation, the external device 114 and the implantable device 104 can each transmit concurrently detected signals to the second external 1302 device for comparative analysis by the second external device 1302. Based on correspondence between these signals as determined by the second external device 1302, the second external device 1302 can be configured to authorize and/or initiate a telemetry session between the implantable device 104 and the external device 114 and/or between the implantable device 104 and the second external device 1302 in various embodiments.

In accordance with some of the embodiments associated with system 1300, the second external device 1302 need not perform the signal detecting functions described with reference to the detection devices 206 and 216 or the signal generation functions described with reference to signal generation device 704. This embodiment can facilitate the integration of certain signal detection and signal generation devices (e.g., various medical devices and health monitoring devices) that may not be configured to perform various telemetry operations with an implantable device 104, but can provide highly specified signal detection and/or signal generation functions generally not suitable for integration into mainstream commercial devices that employed for telemetry with an implantable device 104. Example mainstream commercial devices include, but are not limited to, smart phones, tablets, laptop PCs, desktop PCs, etc. that are configured to employ commercially available telemetry protocols to communicate with an IMD.

In yet another embodiment of system 1300, the external device 114 can be configured to generate/provide a trigger signal that causes the implantable device 104 to enter a pairing mode. For example, as discussed infra, the external device 114 can generate a distinguishable RF signal (e.g., at a non-commercial frequency of sufficient strength) that is detected and interpreted by the implantable device 104 as a signal to activate pairing mode. In response to detection of the trigger signal, the implantable device 104 can enter pairing mode and activate the appropriate sensors/circuitry/antennas etc., used by the implantable device 104, to detect/receive unique signals (e.g., signals 204, 202, 701, and/or 702) and/or security information (e.g., security information data packet 703) used by the implantable device 104 to authorize telemetry.

In some embodiments, after generation/provision of the trigger signal, the external device 114 can generate/provide the unique signal and/or security information (as previously discussed). However, in other embodiments, the second external device 1302 can be configured to generate/provide the unique signal/security information after the implantable device 104 has entered pairing mode. According to these embodiments, the second external device 1302 can include the various features and functionality of external device 114 and the external device 114 can merely function as a device that provides the trigger signal. The various embodiments associated with system 1300 are described in greater detail with reference to FIG. 14.

Figure 14:
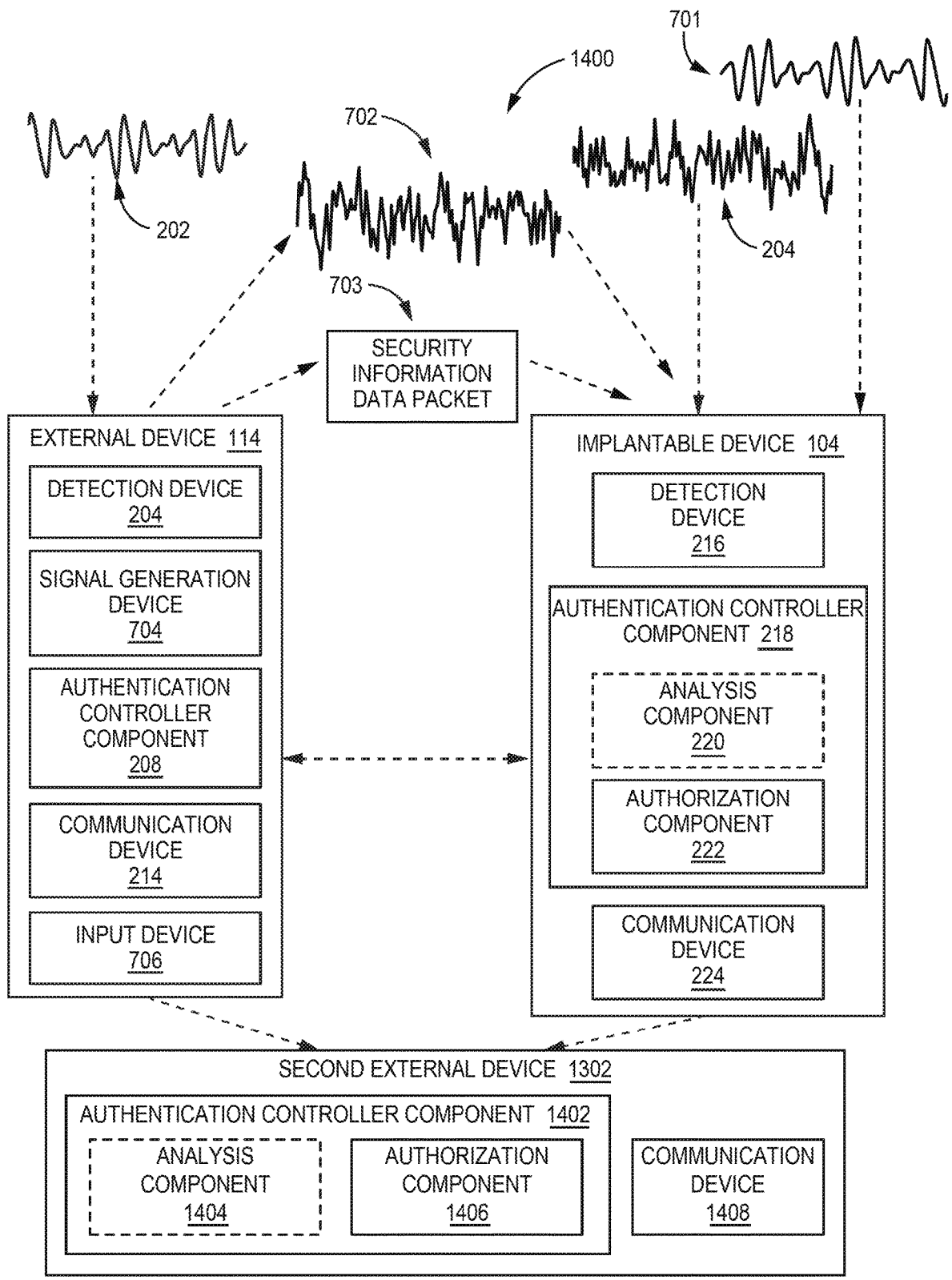
FIG. 14 illustrates a block diagram of a non-limiting system facilitating authorized telemetry with an implantable device and a second external device based on communication of security information between the implantable device and a first external device in accordance with one or more embodiments described herein.

FIG. 14 illustrates a block diagram of a non-limiting system 1400 facilitating authorized telemetry with an implantable device and a second external device based on communication of security information between the implantable device and an external device in accordance with one or more embodiments described herein. Although not shown, it is to be appreciated that the implantable device 104 is implanted within a body of a living being. For exemplary purposes, system 700 is described with the assumption that the implantable device 104 is implanted within a human being. In some embodiments, the implantable device 104 can be implanted within an animal.

System 1400 includes one or more of the structure, features and/or functionality of system 1300 with the addition of various components included in the respective devices of system 1300 that facilitate the various implementations of systems 1300 and 1400. In accordance with system 1400, in various different embodiments, the external device 114 and the implantable device 104 can include one or more of the same or similar components, structure, features and/or functionality as previously described with respect to systems 100, 200 and 700. In various different embodiments, as shown, system 1400 can also include signals 202, 204, 701, 702 and/or security information data packet 703, the various structures, features and functionalities of which are described supra. Repetitive description of like elements employed in other embodiments described herein is omitted for sake of brevity.

Second external device 1302 can include one or more of the structure, features and functionalities of external device 114 or implantable device 104. For example, second external device 1302 can include authentication controller component 1402, which can include analysis component 1404 and authorization component 1406. Authentication controller component 1402, analysis component 1404, and authorization component 1406, can include one or more of the structures, features and functionalities as authentication controller component 208 or 218, analysis component 210 or 220, and authorization component 212 or 222, respectively.

Communication device 1408 can also include one or more of the structure, features, and functionality as communication device 214 or communication device 224. Repetitive description of like elements employed in other embodiments described herein is omitted for sake of brevity.

In one embodiment of system 1400, the external device 114 and the implantable device 104 can concurrently detect first and second signals, respectively, regarding a physiological state of the body 102 in which the implantable device 104 is implanted, a motion of the body 102, and/or a sound detectable by both the external device 114 and the implantable device 104 (e.g., signal 202 and signal 204, respectively). The external device 114 can further provide the first signal, or electronic information representative of the first signal, to the implantable device 104 and the implantable device 104 can perform comparative analysis between the first and second signals in accordance with the various embodiments described herein (e.g., via analysis component 220). However, in response to a determination that the first and second signals share a defined degree of similarity, rather than initiating a telemetry session with the external device 114, the implantable device 104 can be configured to authorize and/or initiate a telemetry session with the second external device 1302 (e.g., via authorization component 222) in accordance with the various embodiments described herein.

In some embodiments, the implantable device 104 can detect a signal (e.g., signal 701 or signal 702 or security information data packet 703) that is transmitted from the external device 114 to the implantable device 104. The implantable device 104 can perform comparative analysis between the detected signal 701, 702 or received security information data packet 703 and authentication reference information for the detected signal or the security information data packet, in accordance with the various embodiments described herein (e.g., via analysis component 220). However, in response to a determination that the detected signal 701, 702 or the received security information data packet 703 has a defined degree of similarity with the respective authentication reference information for the detected signal or the security information data packet, rather than initiating a telemetry session with the external device 114, the implantable device 104 can be configured to authorize and/or initiate a telemetry session with the second external device 1302 (e.g., via authorization component 222), in accordance with the various embodiments described herein. In some embodiments, the authentication reference information associated with a detected signal (e.g., signal 701 or signal 702) or the received security information data packet (e.g., security information data packet 703) can be associated with or include information identifying the second external device 1302 (e.g., a device identifier) as the assigned device with which the implantable device 104 is configured to initiate and/or conduct a telemetry session.

In another embodiment, second external device 1302 is configured to receive concurrently detected signals from the implantable device 104 and the external device 114, respectively (e.g., via communication device 1408). The second external device 1302 can be further configured to compare the first and second signals via analysis component 1404 (e.g., using one or more of the various techniques previously described with respect to analysis component 210 and/or analysis component 220).

In one embodiment, in response to a determination by the second external device 1302 that the first and second signals have a defined degree of similarity, the second external device 1302 can authorize and/or initiate a telemetry session between the implantable device 104 and the external device 114 (e.g., via authorization component 1406). For example, the second external device 1302 can send the implantable device 104 and/or the external device 114 respective authentication information (e.g., device identifiers for the external device 114 and the implantable device 104) and/or session keys in accordance with suitable existing pairing technology. In an embodiment, the session keys can be set to expire after a defined duration of time. However, in response to a determination by the second external device 1302 that the first and second signals fail to have the defined degree of similarity, the second external device 1302 can forgo authorization and initiation of a telemetry session between the implantable device 104 and the external device 114.

In another embodiment, in response to a determination by the second external device 1302 that the first and second signals have a defined degree of similarity (e.g., via analysis component 1404), the second external device 1302 can authorize and/or initiate a telemetry session between the implantable device 104 and the second external device 1302. For example, the second external device 1302 can send the implantable device 104 a communication indicating authorization for the telemetry session has been provided (e.g., via communication device 1408). In response to the communication, the implantable device 104 can send the second external device 1302 authentication information (e.g., device identifiers for the implantable device 104) and/or session keys in accordance with suitable existing pairing technology. In an embodiment, the session keys can be set to expire after a defined duration of time. However, in response to a determination by the second external device 1302 that the first and second signals fail to have the defined degree of similarity, the second external device 1302 can forgo authorization and initiation of a telemetry session with the implantable device 104.

In accordance with this embodiment, the external device 114 can include a device configured to detect one or more of the various physiological, motion and/or audio based signals described herein. However, the external device 114 can be configured to perform minimal processing functions associated with conducting telemetry with the implantable device 104. For example, the external device can include a personal heart rate monitor configured to be worn on the body 102 (e.g., under clothing of a patient) that provides for determining heart rate. In another example, external device 114 can include a personal vital signs monitoring device that can determine the blood pressure, temperature and/or heart rate of the body 102 of the patient. External device 114 can transmit the signal indicative of detected information to the second external device 1302 and/or to the implantable device 104 in various embodiments. In embodiments in which the external device 114 transmits the signal only to the implantable device 104, the implantable device 104 can be further configured to relay this information to the second external device 1302.

Figure 15:
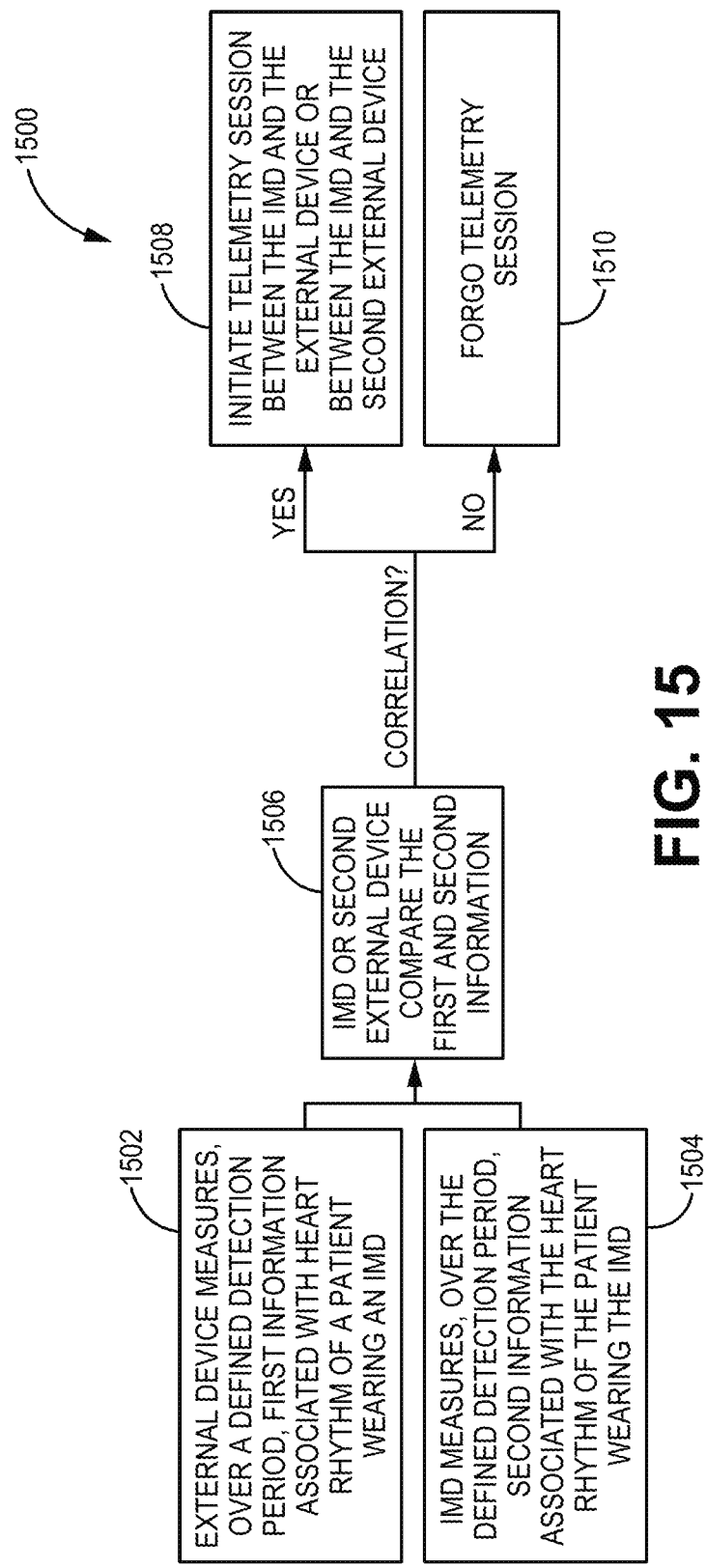
FIG. 15 illustrates a flow diagram of an example, non-limiting method of facilitating authorized telemetry with an implantable device and a second external device based on concurrent detection, by the implantable device and a first external device, of information associated with a heart rhythm of a patient in which the implantable device is implanted in accordance with one or more embodiments described herein.

FIG. 15 illustrates a flow diagram of an example, non-limiting method 1500 facilitating authorized telemetry with an IMD and an external device or a second external device based on concurrent detection, by the IMD and the external device, of information associated with a heart rhythm of the body of the patient in which the IMD is implanted in accordance with one or more embodiments described herein.

With reference to FIGS. 1, 13, 14 and/or 15, at 1502, an external device (e.g., external device 114), measures, over a defined detection period, first information associated with heart rhythm of a patient wearing an IMD (e.g., implantable device 104). For example, the external device can activate a camera of the external device and capture image data of the change in patient blood color over a defined duration of time in response to placement the finger of the patient over at least a portion of the lens of the camera. The external device 114 can further estimate the heart rate of the body of the patient based on the change in blood color.

At 1504, the IMD measures, over the defined detection period, second information associated with the heart rhythm of the patient wearing the IMD. For example, the IMD can activate an ECG device or a pulse oximeter to capture signals (e.g., electrical activity of the heart, or change in blood oxygenation levels, respectively) that can be correlated to the heart rate of the body of the patient.

At 1506, the IMD or a second external device (e.g., second external device 1302), compare the first and second information to determine a degree of correlation between the first and second information. For example, in one embodiment, the external device can send the first information to the IMD and the IMD can then compare the first and second information. In another embodiment, both the external device and the IMD can send the first and second information, respectively, to the second external device. The second external device can then compare the first and second information.

In response to a determination that the first and second information have a defined degree of correlation, either by the IMD or the second external device, at 1508 a telemetry session is initiated between the IMD and the external device or between the IMD and the second external device. Either scenario can be authorized and/or initiated by the second external device. At 1510, in response to a determination that the first and second information fail to have the defined degree of correlation, the telemetry session is forgone.

Figure 16:
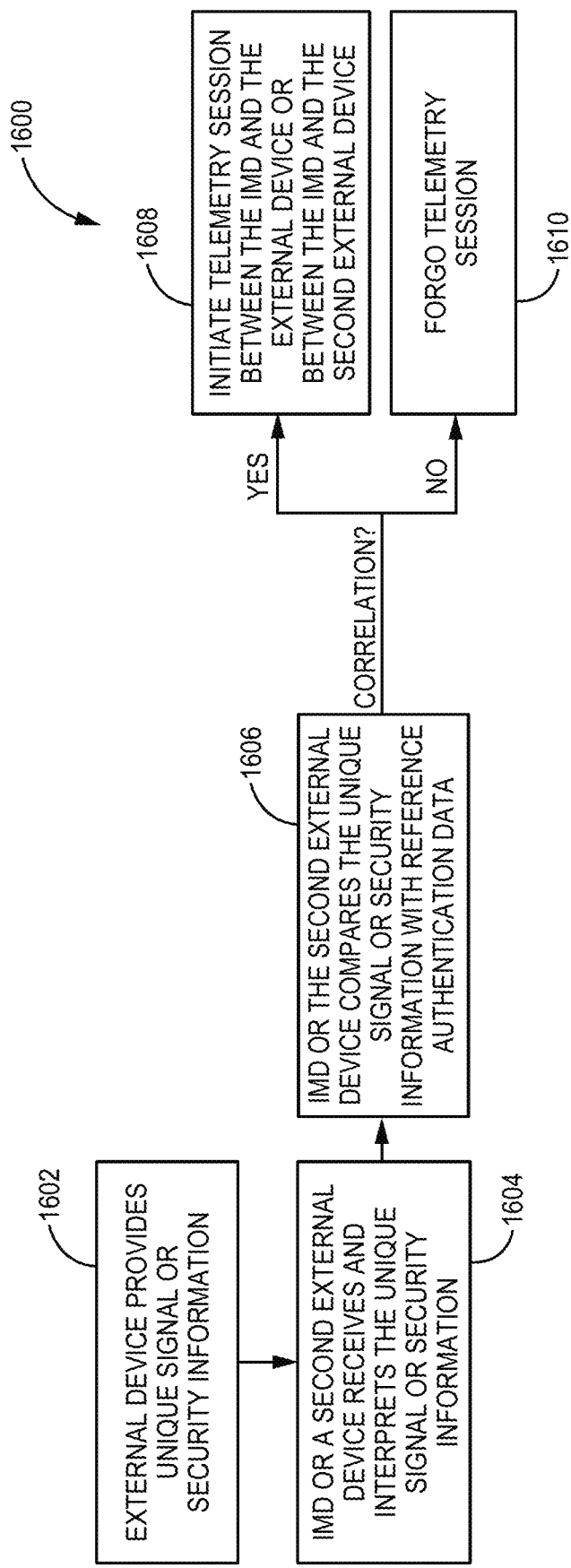
FIG. 16 illustrates a flow diagram of an example, non-limiting method of facilitating authorized telemetry with an implantable device and a second external device based on communication of security information between the implantable device and a first external device in accordance with one or more embodiments described herein.

FIG. 16 illustrates a flow diagram of an example, non-limiting method 1600 of facilitating authorized telemetry with an IMD and a second external device based on communication of security information between the IMD and a first external device in accordance with one or more embodiments described herein.

With reference to FIGS. 1, 13, 14 and/or 16, at 1602, an external device (e.g., external device 114) provides a unique signal (e.g., signal 702) or security information (e.g., security information data packet 703) to an IMD (e.g., implantable device 104) or a second external device (e.g., second external device 1302). At 1604, the IMD or the second external device receives and interprets the unique signal or security information.

At 1606, the IMD or the second external device can compare the unique signal or security information with reference authentication data. In response to a determination (either by the IMD or the second external device) that the unique signal or the security information have a defined degree of correlation with the reference authentication data, at 1608 a telemetry session is initiated between the IMD and the external device or between the IMD and the second external device. Either scenario can be authorized and/or initiated by the second external device. At 1610, in response to a determination that the unique signal or the security information fail to have the defined degree of similarity or correlation, initiation of a telemetry session is forgone.

Figure 17:
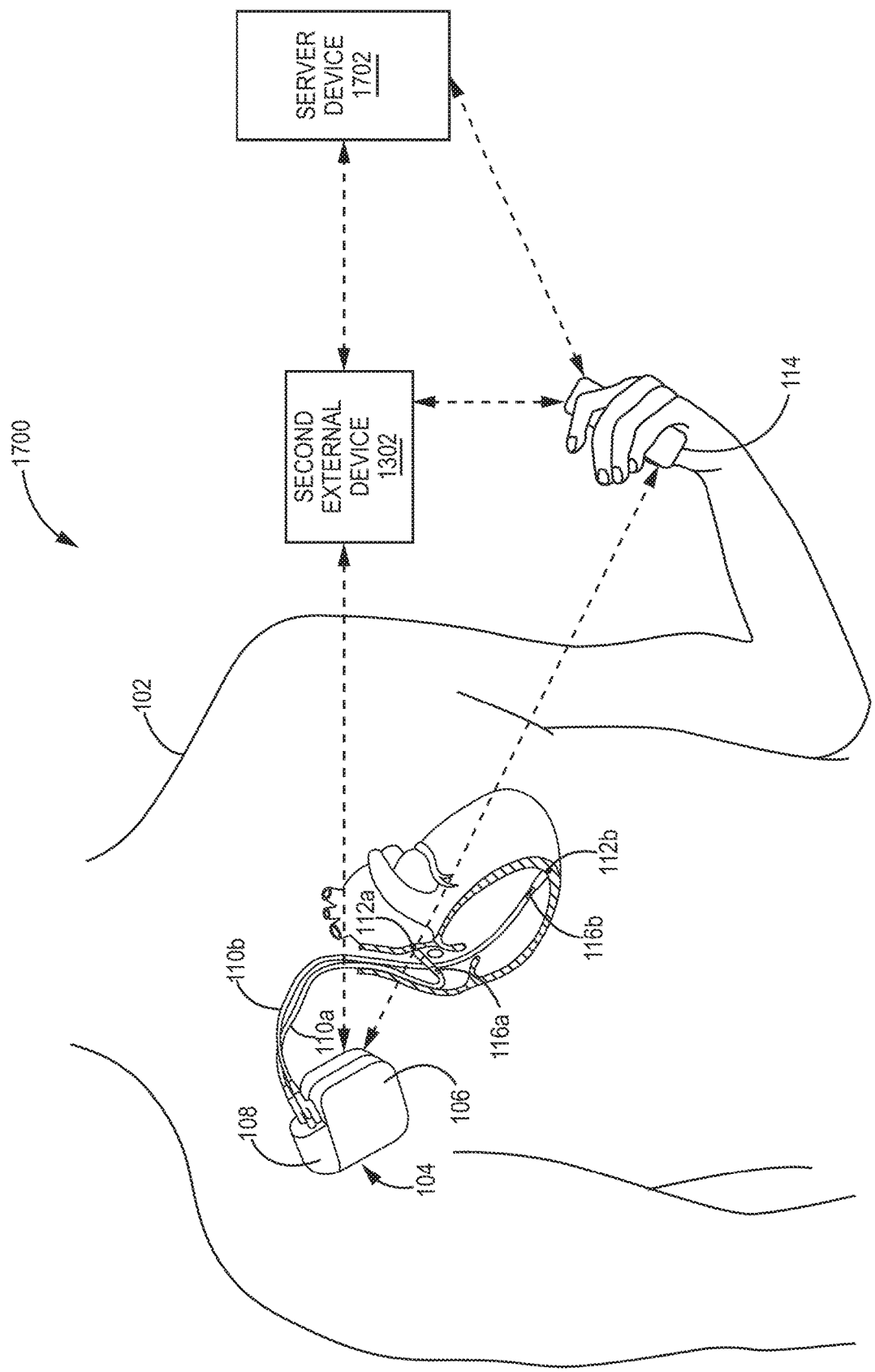
FIG. 17 illustrates a schematic diagram of another example, non-limiting medical device telemetry system facilitating authorized telemetry with an implantable device in accordance with one or more embodiments described herein.

Referring now to FIG. 17, illustrated is a schematic diagram of another example, non-limiting medical device telemetry system 1700 facilitating authorized telemetry with an implantable device in accordance with one or more embodiments described herein. System 1700 can include one or more of the various structures, features and/or functionalities of system 100 with the addition of a server device 1702. Repetitive description of like elements employed in other embodiments described herein is omitted for sake of brevity.

In some embodiments, external device 114 and/or second external device 1302 is configured to communicate with a server device 1702 via one or more of the networks described above. For example, the external device 114 can receive information from the server device 1702 indicative of instructions dictating a particular audio signal, RF signal, or light signal to be transmitted by the external device 114 to the implantable device 104 in association with authorizing a telemetry session with the implantable device 104. As another example, after the implantable device 104 and the external device 114 or the second external device 1302 have established an authorized telemetry session using one or more of the authorization methods described herein, the external device 114 and/or the second external device 1302 can communicate data between the implantable device 104 and the server device 1702 via a network. This data can include, but is not limited to, control commands issued by the server device 1702, sent from the server device 1702 to the implantable device 104 (or to the second external device 1302) via the external device 114. In another embodiment, the data can also include information transmitted from the implantable device 104 to the server device 1702 via the external device 114 or via the second external device 1302.

In some embodiments, the server device 1702 can store computer-readable storage media on which instructions facilitating operations of an application service provider can be stored. The application service provider can be configured to facilitate operations of an IMD application stored on the external device 114 that can be employed by the external device 114 to interact with the implantable device 104.

Figure 18:
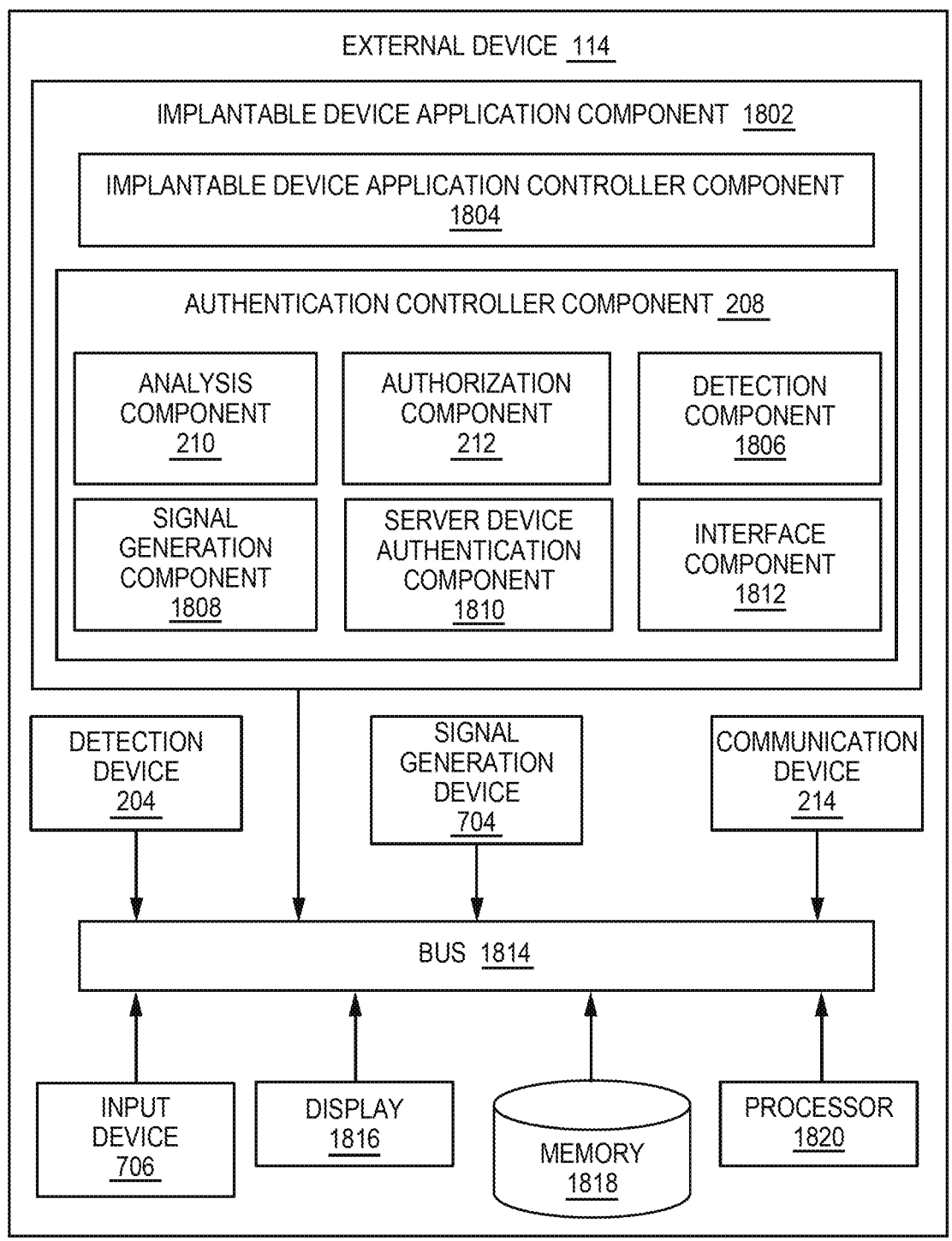
FIG. 18 illustrates an example, non-limiting block diagram of an external device configured to facilitate telemetry with an implantable device in accordance with one or more embodiments described herein.

FIG. 18 illustrates an example, non-limiting block diagram of an external device 114 configured to facilitate telemetry with an implantable device 104 in accordance with one or more embodiments described herein. In various embodiments, one or more of the structures, features and/or functionalities of external device 114 as presented in FIGS. 1-18 can be included in and/or employed by the second external device 1302. Repetitive description of like elements employed in other embodiments described herein is omitted for sake of brevity.

For example, with reference to FIGS. 1, 17 and 18, the external device 114 can include an implantable device application component (e.g., implantable device application component 1802) that can facilitate interaction with an implantable device (e.g., implantable device 104) via a variety of different embodiments (e.g., reading and displaying information read from the implantable device, programming the implantable device or controlling functions of the implantable device). In some embodiments, the implantable device application component 1802 can also include functionality to cause the external device 114 to perform or facilitate one or more of the various authorization methods disclosed herein to enable authorized communication between the implantable device and the external device 114 (or the second external device 1302).

External device 114 can also include memory 1818 that stores computer-executable components, and a processor 1820 that executes the computer-executable components (e.g., the implantable device application component 1802 and/or the various components of the implantable device application component) stored in the memory. External device 114 further includes a display 1816 and a bus 1814 that couples the various components including, but not limited to, implantable device application component 1802

(and the various components of the implantable device application component 1802), detection device 206, signal generation device 704, communication device 214, input device 706, display 1816, memory 1818 and/or processor 1820.

The implantable device application controller component 1804 can facilitate one or more of a variety of potential application functions provided via the implantable device application component 1802 that may be unrelated to authentication/authorization of telemetry between the external device 114 and the implantable device 104. For example, these functions can include, but are not limited to, those associated with facilitating interfacing between the implantable device 104 and the external device (e.g., reading/receiving data from the implantable device 104 and/or controlling or programming the implantable device after a telemetry session has been authorized via the authorization techniques described herein). In another example, these functions can facilitate interfacing between the external device 114 and the server device 1702 in one or more ways as described herein. In another example, these functions can facilitate remote storing and/or tracking of patient medical information as relates to the IMD (e.g., cloud-based computing functionalities).

Authentication controller component 208 can be configured to facilitate the various authorization and authentication functions described herein in connection with facilitating an authorized telemetry session between external device 114 and an implantable device (or another external device), as previously described with reference to systems 200, 700 and 1400. In one or more embodiments, authentication controller component 208 can further include detection component 1806, signal generation component 1808, server device authentication component 1810 and interface component 1812.

Authentication controller component 208 can employ detection component 1806 in association with controlling operation of the detection device 206. For example, detection component 1806 can issue commands to the detection device 206 that control activation and/or deactivation of detection device 206. Similarly, authentication controller component 208 can employ signal generation component 1808 in association with controlling operation of the signal generation device 704. For example, signal generation component 1808 can issue commands to the signal generation device that control when the signal generation device generates and/or emits a unique audio signal, RF signal or light signal.

Server device authentication component 1810 is configured to facilitate authenticating and/or authorizing the external device 114 (or a user of the external device 114) in association with providing the external device 114 (or the user of the external device 114) access to the various features and functionalities of implantable device application component 1802, including, but not limited to, features associated with establishing an authorized telemetry session with the implantable device 104. For example, the server device 1702 can provide different users a variety of services associated with the implantable device application component 1802. For instance, in embodiments in which the implantable device 104 is or includes an IMD, one of these services can include retaining and/or providing access to patient health information/records associated with the IMD of the patient. Another one of these services can include managing access to implantable devices by different users.

In one or more embodiments, in association with managing access to implantable devices by different users, the server device 1702 and the server device authentication component 1810 can employ a secure authentication procedure to determine whether an external device 114 and/or a user of the external device 114 is authorized to conduct telemetry with an implantable device 104. According to these embodiments, the server device 1702 can issue or provide the external device 114 with access keys, security information (e.g., security information data packet 703 or session keys required for provision by the external device 114 to the implantable device 104) to establish an authorized telemetry session only after the external device/user of the external device 114 has successfully performed the authentication procedure with the server device 1702.

In an embodiment, the server device 1702 can retain or access information identifying implantable devices (e.g., unique implantable device identifiers) and the one or more external devices (e.g., via unique external device identifiers) and/or users of the external devices authorized to access the respective implantable devices. The server device authentication component 1810 can facilitate receiving authentication input at the external device 114 (e.g., username/password) identifying the external device 114 and/or the user of the external device 114 in association with a request to establish a telemetry session with an implantable device. The server device authentication component 1810 can further provide the authentication input and the telemetry request to the server device 1702.

Upon reception of the request, the server device 1702 can perform an authentication/authorization procedure to verify the identity of the external device 114/user of the external device 114 based on the authentication input and to determine whether the external device/user of the external device is authorized to conduct telemetry with the implantable device. The server device 1702 can employ various user authentication/authorization protocols to verify the identity of an external device 114 (or user of the external device 114) requesting telemetry with a particular implantable device. For example, server device 1702 can employ a username and password system, an external authorization system, a single sign-on service and/or a public key infrastructure system (PKI), etc. Upon successful authentication/authorization, the server device 1702 can issue or provide the external device 114 with a necessary access key, security information (e.g., security information data packet 703) and/or session key, required for provision by the external device 114 to the implantable device 104 to establish the authorized telemetry session.

In another embodiment, server device authentication component 1810 can restrict access to the authentication capabilities of the implantable device application component 1802 based on authentication/authorization of the user of the application with the server device 1702 (e.g., via a sign in procedure). In accordance with this embodiment, server device authentication component 1810 can control access to a personal user account associated with the implantable device application component 1802 and server device 1702 by implementing an authentication/authorization procedure (e.g., enter user name and password) prior to allowing access to the personal user account. The personal user account can include information identifying the user's implantable device and/or the unique authentication signal 702 (e.g., information identifying a unique user action based signal, a unique audio signal, a unique RF signal or a unique light signal) or security information data packet 703 (e.g., image data, password data or secret key data) associated with accessing the implantable device 104. According to this embodiment, to receive, by the external device 114/user of the external device 114, access to the information identifying the unique authentication signal or the security information, the external device 114/user of the external device 114 can first perform an authentication procedure with the server device 1702 (e.g., enter user name and password). Upon successful authentication/log in, the server device 1702 can provide the external device 114/user of the external device 114 access to the information (e.g., via the access of the user's personal user account).

Interface component 1812 is configured to generate a user interface for presentation via the display 1816 that can facilitate activation and/or utilization of the various functionalities of the external device 114. For example, the user interface can facilitate using the implantable device application component 1802, displaying information received from an implantable device 104, issuing control commands to the implantable device 104, or issuing commands to change the parameters or otherwise program or re-program the implantable device 104. In some embodiments, the interface component 1812 is configured to provide the user interface to a user of the external device 114, or to another device configured to read the user interface. For example, the display 1816 can be a touch screen display in some embodiments. In some embodiments, the display 1816 can be a component that outputs a visual, audible or other indicator of information.

Figure 19:
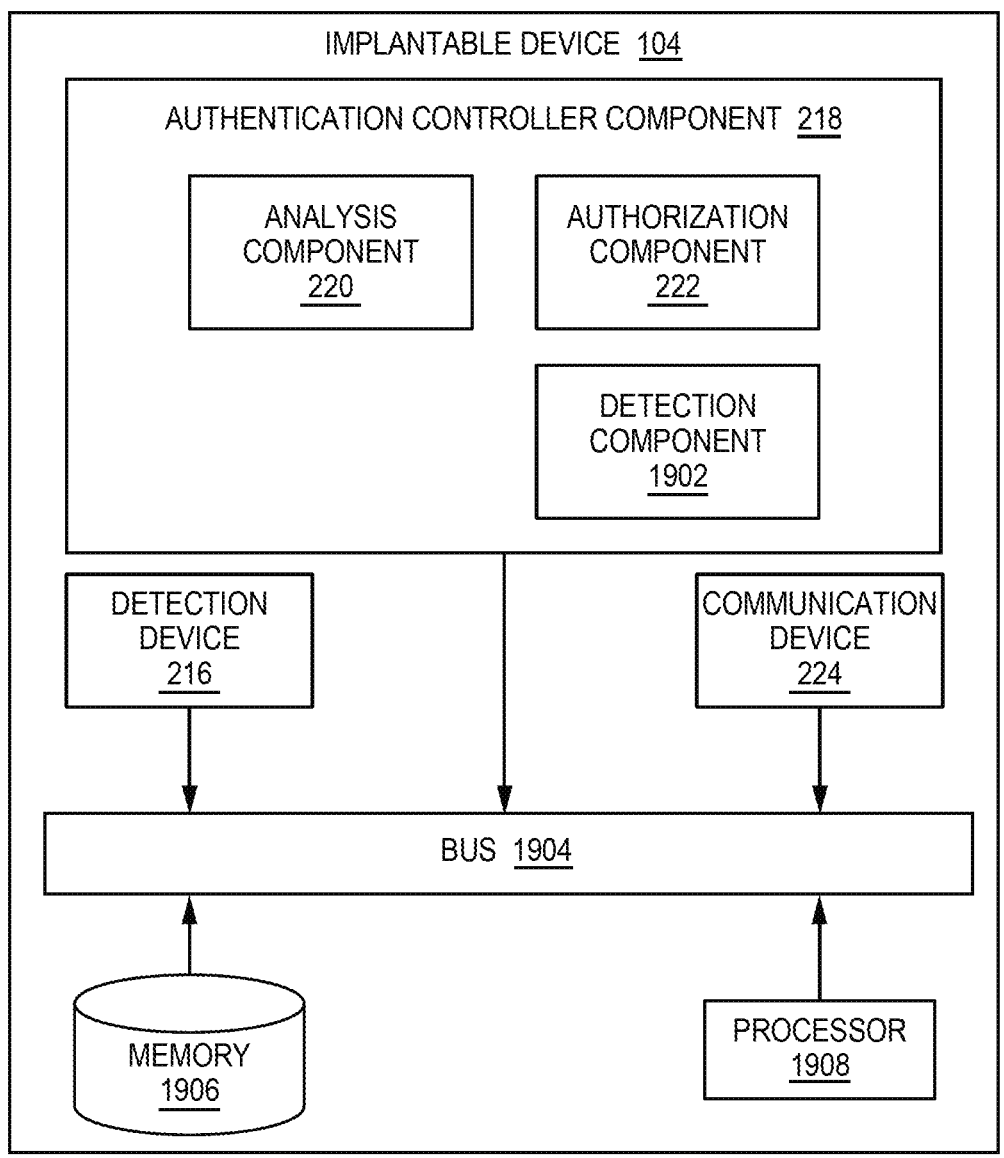
FIG. 19 illustrates an example, non-limiting block diagram of an implantable device configured to facilitate telemetry with an implantable device in accordance with one or more embodiments described herein.

FIG. 19 illustrates a non-limiting block diagram of an implantable device 104 configured to facilitate telemetry with an implantable device in accordance with one or more embodiments described herein. Implantable device 104 as presented in association with FIG. 19 can include one or more of the components and/or devices previously described with reference to FIGS. 1-17. Repetitive description of like elements employed in other embodiments described herein is omitted for sake of brevity.

Implantable device 104 can also include memory 1906 that stores computer-executable components, and a processor 1908 that executes the computer-executable components (e.g., authentication controller component 218 and/or the various components of the authentication controller component 218) stored in the memory 1906. Implantable device 104 further includes a bus 1904 that couples the various implantable device components including, but not limited to, authentication controller component 218 (and the various components of the authentication controller component 218), detection device 216, communication device 224, memory 1906 and processor 1908.

Authentication controller component 218 is configured to facilitate various operations of implantable device 104 in connection with facilitating an authorized telemetry session between the implantable device 104 and external device 114 (or between the implantable device and another external device (e.g., second external device 1302 of FIG. 13)) as previously described with reference to FIGS. 2, 7 and 14.

Figure 20:
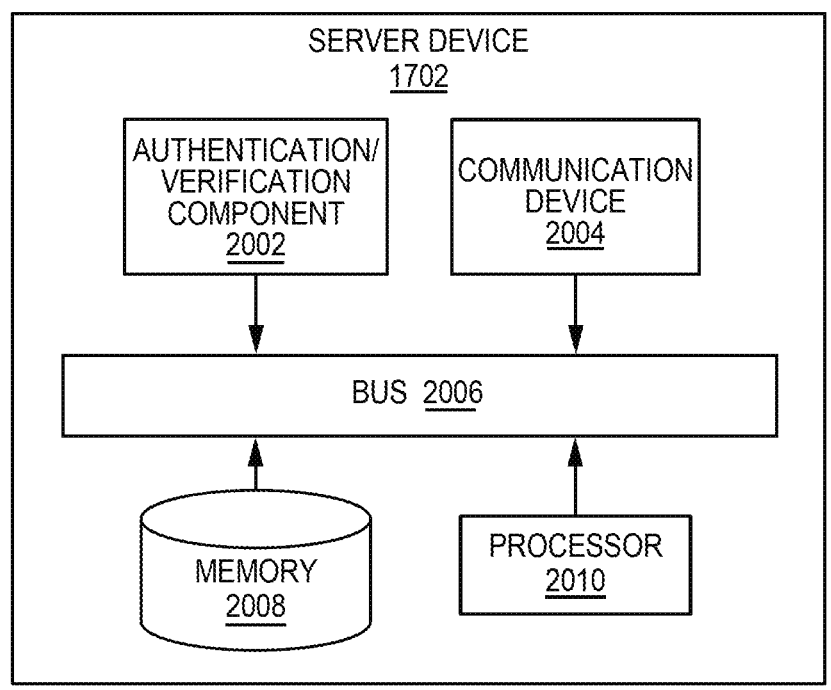
FIG. 20 illustrates an example, non-limiting block diagram of a server device configured to facilitate telemetry with an implantable device in accordance with one or more embodiments described herein.

FIG. 20 illustrates a block diagram of an example, non-limiting server device 1702 configured to facilitate telemetry with an implantable device in accordance with one or more embodiments described herein. Repetitive description of like elements employed in other embodiments described herein is omitted for sake of brevity.

The server device 1702 can include an authentication/verification component 2002 and communication device 2004. Server device 1702 can also include memory 2008 that stores computer-executable components, and a processor 2010 that executes computer-executable components stored in the memory 2008 (e.g., the authentication/verification component 2002). Server device 1702 can include a bus 2006 that couples the various components of the server device 1702 including, but not limited to, authentication/verification component 2002, communication device 2004, memory 2008, and a processor 2010.

Communication device 2004 is configured to facilitate communication between the server device 1702 and another device (e.g., external device 114 or second external device 1302). Communication device 2004 can include one or more of the features and functionalities as communication device 214. For example, communication device 2004 can include a transmitter and/or receiver configured to transmit and/or receive electrical wireless signals. For example, communication device 2004 can communicate with another device using various wireless communication protocols including, but not limited to, RF communications or other forms of communication including both proprietary and non-proprietary communication protocols.

With reference to FIGS. 18 and 20, according to some embodiments, the server device 1702 can provide additional security in association with establishing an authorized telemetry session between the implantable device 104 and the external device 114 (or another device) by using an authentication method. The authentication method can be employed between the server device 1702 and the external device 114 (or between the user of the external device 114) before allowing the implantable device application component 1802 of FIG. 18 to be activated and/or used.

For example, the server device 1702 can provide different external devices (or different users of external devices) a variety of services associated with the implantable device application component 1802 of the external device 114. For instance, in embodiments in which the implantable device 104 is or includes an IMD, one of these services can include retaining and/or providing access to patient health information/records associated with the IMD of the patient. Another of these services can include managing access to implantable devices by different users. For example, as discussed supra, server device 1702 can provide/issue an external device 114 with the security information (e.g., information defining a unique signal 702, security information data packet 703 or session keys) required for provision by the external device 114 to an implantable device 104 to establish a telemetry session, in response to performance of an authentication/authorization procedure.

In association with managing access to implantable devices by different users, the respective users can establish user accounts with the server device 1702. The users can access their respective user accounts hosted by the server device 1702 via the implantable device application component (e.g., implantable device application component 1802) provided on their respective external devices (e.g., external device 114). In an embodiment, the respective user accounts can be associated with personal information for the respective users. This personal information can include, but is not limited to, information regarding the implantable device or one or more external devices the implantable device is authorized to access. The personal information can also include, but is not limited to, information indicative of the manner in which the external device can access/communicate with the implantable device 104 (e.g., read information at the implantable device only; read information at the implantable device and program one or more aspects of the implantable device). The personal information can also include, but is not limited to, data defining a unique signal (e.g., signal 702) or security information (e.g., security information data packet 703) that is required to access the implantable device 104 or devices. The personal information can also include data defining a distinct physical action (e.g., holding breath and raising hands above head) that is utilized to access the implantable device 104 or devices (e.g., the physical action association with generation of signal 701).

In some embodiments, the server device 1702 can call for external devices (and/or users of external devices) to sign in to the respective user accounts to access the user accounts and/or personal information associated with the respective user accounts. The server device 1702 can also call for the users to sign in to the respective user accounts prior to allowing the users to access the various authorization functionality provided by the implantable device application component 1802. Server device 1702 can be configured to employ various user authentication/authorization protocols to perform the secure sign in procedure. For example, server device 1702 can employ a username and password system, an external authorization system, a single sign-on service, a PKI, etc.

Figure 21:
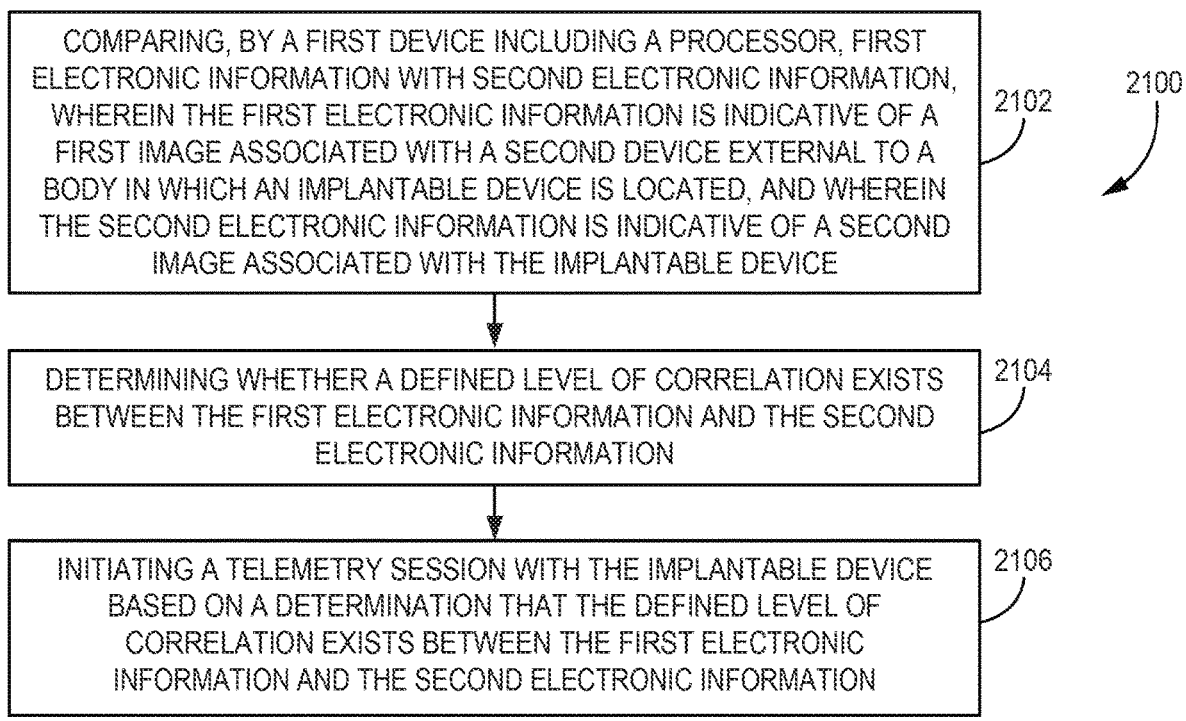
FIG. 21 illustrates a flow diagram of an example, non-limiting method facilitating authorized telemetry with an implantable device in accordance with one or more embodiments described herein.
Figure 22:
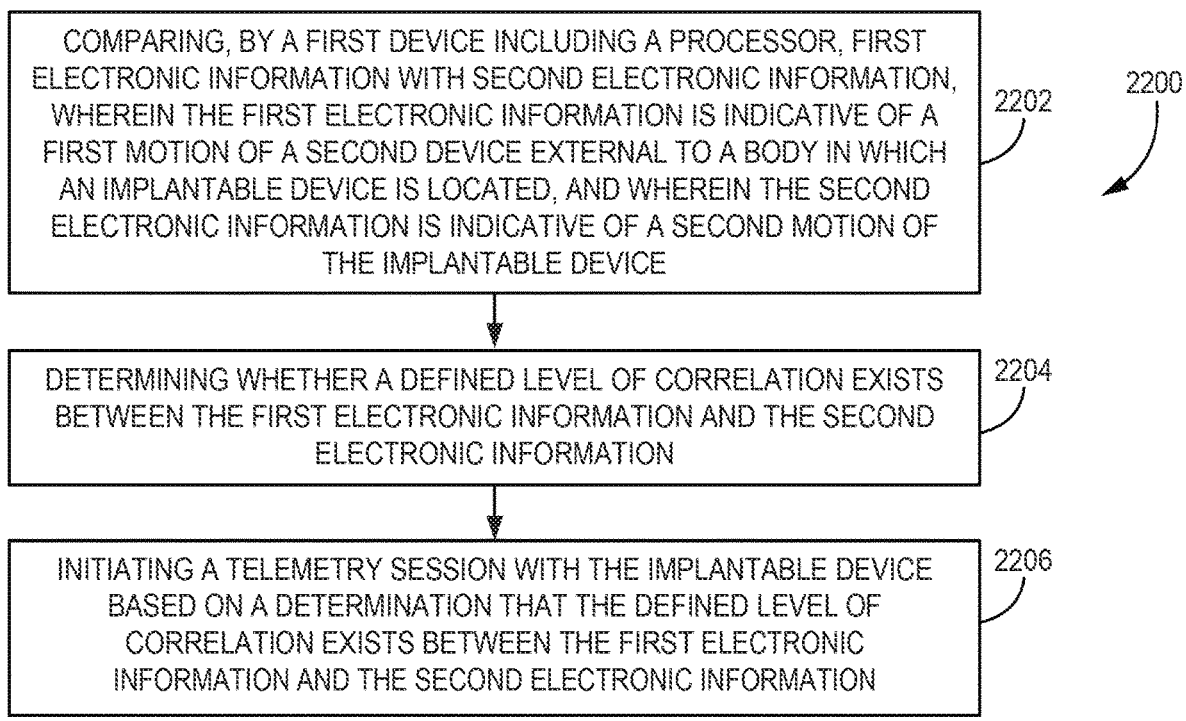
FIG. 22 illustrates a flow diagram of an example, non-limiting method facilitating authorized telemetry with an implantable device in accordance with one or more embodiments described herein.
Figure 23:
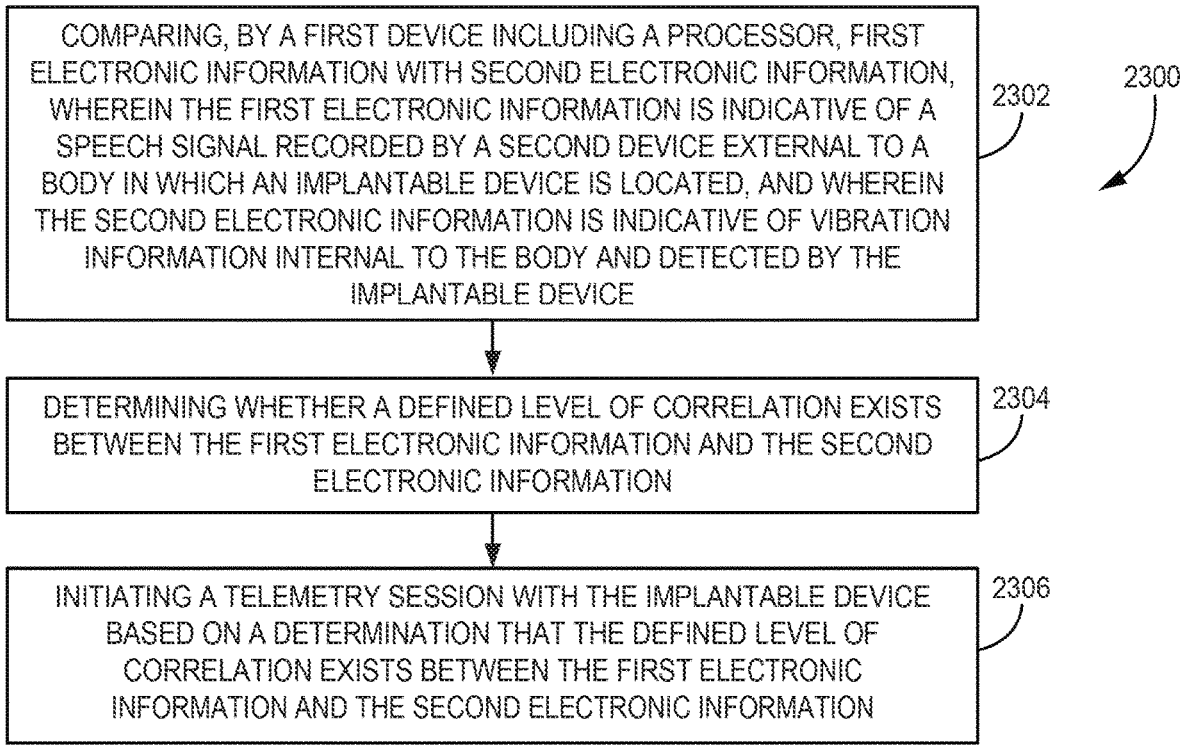
FIG. 23 illustrates a flow diagram of an example, non-limiting method facilitating authorized telemetry with an implantable device in accordance with one or more embodiments described herein.

In view of the example systems and/or devices described herein, example methods that can be implemented in accordance with the disclosed embodiments can be further appreciated with reference to flowcharts in FIGS. 21, 22 and 23. For purposes of simplicity of explanation, example methods disclosed herein are presented and described as a series of acts; however, it is to be understood and appreciated that the disclosed subject matter is not limited by the order of acts, as some acts may occur in different orders and/or concurrently with other acts from those shown and/or described herein. For example, a method disclosed herein can alternatively be represented as a series of interrelated states or events, such as in a state diagram. Moreover, interaction diagrams can represent methods in accordance with the disclosed subject matter when disparate entities enact disparate portions of the methods. Furthermore, not all illustrated acts are required to implement a method in accordance with the embodiments.

FIG. 21 illustrates a flow diagram of an example, non-limiting method 2100 facilitating authorized telemetry with an implantable device in accordance with one or more embodiments described herein. Repetitive description of like elements employed in other embodiments described herein is omitted for sake of brevity.

With reference to FIGS. 1, 7, 14 and 21, at 2102, first electronic information is compared with second electronic information by a first device including a processor (e.g., implantable device 104 or second external device 1302). The first electronic information is indicative of a first image associated with a second device (e.g., external device 114) external to a body in which an implantable device 104 is located. For example, the first electronic information can include information representative of a picture of the face, distinguishing body part, distinguishing hand symbol, distinguishing tattoo of the body in which the implantable device 104 is implanted. The second electronic information is indicative of second image associated with (e.g., stored in or accessible by) the implantable device 104. For example, the second image can include a reference image.

In some embodiments, the first electronic information and the second electronic information can be collected from the implantable device 104 and the external device 114, and compared by another device (e.g., second external device 1302). In other embodiments, the first electronic information or the second electronic information can be collected by the implantable device 104 or the external device 114 and compared by the implantable device 104 or the external device 114 to the information already detected by the implantable device 104 or the external device 114.

At 2104, a determination is made as to whether a defined level of correlation exists between the first electronic information and the second electronic information. At 2106, a telemetry session is initiated with the implantable device 104 based on a determination that the defined level of correlation exists between the first electronic information and the second electronic information.

FIG. 22 illustrates a flow diagram of an example, non-limiting method 2200 facilitating authorized telemetry with an implantable device in accordance with one or more embodiments described herein. Repetitive description of like elements employed in other embodiments described herein is omitted for sake of brevity.

With reference to FIGS. 1, 2, 14 and 22, at 2202, first electronic information is compared with second electronic information by a first device including a processor (e.g., implantable device 104 or second external device 1302). The first electronic information is indicative of a first motion of a second device (e.g., external device 114) external to the body 102 in which an implantable device 104 is located. For example, the first electronic information can include information representative of the second device in response to motion of the body 102 in which the implantable device 104 is located, wherein the second device is held, worn, or otherwise attached to the body 102 in which the implantable device 104 is implanted. The second electronic information is indicative of as a motion of the implantable device 104.

At 2204, a determination is made as to whether a defined level of correlation exists between the first electronic information and the second electronic information. At 2206, a telemetry session is initiated with the implantable device based on a determination that the defined level of correlation exists between the first electronic information and the second electronic information.

FIG. 23 illustrates a flow diagram of an example, non-limiting method 2300 facilitating authorized telemetry with an implantable device in accordance with one or more embodiments described herein. Repetitive description of like elements employed in other embodiments described herein is omitted for sake of brevity.

With reference to FIGS. 1, 2, 14 and 22, at 2302, first electronic information is compared with second electronic information by a first device including a processor (e.g., implantable device 104 or second external device 1302). The first electronic information is indicative of a speech signal recorded by a second device (e.g., external device 114) external to a body 102 in which the implantable device 104 is located. For example, the first electronic information can include information representative of speech (e.g., an audio signal indicative of a sound, a word, a phrase, a melody or a song) within the body 102 in which the implantable device 104 is implanted. The second electronic information is indicative of vibration information internal to the body 102 and detected by the implantable device 104. For example, the second electronic information can include information representative of vibrations resonating inside the body 102 associated with vibration of vocal cords of the body 102 that occurs when the speech occurs.

At 2304, a determination is made as to whether a defined level of correlation exists between the first electronic information and the second electronic information. At 2306, a telemetry session is initiated with the implantable device based on a determination that the defined level of correlation exists between the first electronic information and the second electronic information.

Figure 24:
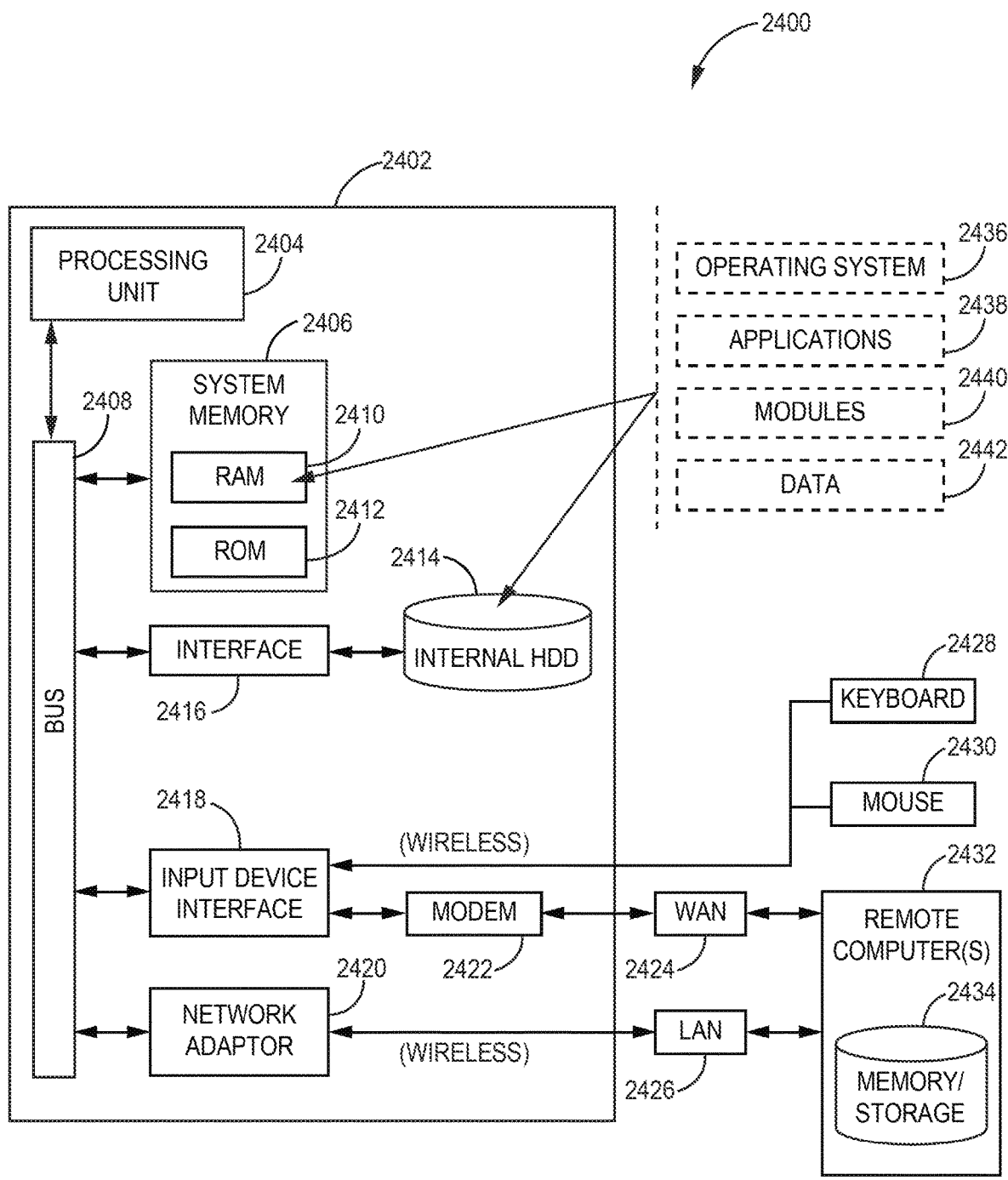
FIG. 24 illustrates a block diagram of a computer operable to facilitate telemetry with or via an implantable device in accordance with one or more embodiments described herein.

To provide additional context for one or more embodiments described herein, FIG. 24 and the following discussion are intended to provide a brief, general description of a suitable computing environment 2400 in which the one or more embodiments described herein can be implemented. For example, computing environment 2400 can be included in external device 114, implantable device 104, second external device 1302 and/or server device 1702.

Generally, program modules include routines, programs, components, data structures that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per sc.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 24, example environment 2400 for implementing one or more embodiments of the embodiments described herein includes computer 2402. Computer 2402 can include processing unit 2404, system memory 2406 and system bus 2408. System bus 2408 couples system components including, but not limited to, system memory 2406 to processing unit 2404. Processing unit 2404 can be any of various commercially available processors. Dual microprocessors and other multi-processor architectures can also be employed as processing unit 2404.

System bus 2408 can be any of several types of bus structure that can further interconnect to a memory bus (with or without a memory controller), a peripheral bus, and a local bus using any of a variety of commercially available bus architectures. System memory 2406 includes RAM 2410 and ROM 2412. A basic input/output system (BIOS) can be stored in a non-volatile memory such as ROM, erasable programmable read only memory (EPROM), EEPROM, which BIOS contains the basic routines that help to transfer information between elements within computer 2402, such as during startup. RAM 2410 can also include a high-speed RAM such as static RAM for caching data.

Computer 2402 further includes internal hard disk drive (HDD) 2414 (e.g., Enhanced Integrated Drive Electronics (EIDE), Serial Advanced Technology Attachment (SATA)). HDD 2414 can be connected to system bus 2408 by hard disk drive interface 2416. The drives and their associated computer-readable storage media provide nonvolatile storage of data, data structures, computer-executable instructions, and so forth. For computer 2402, the drives and storage media accommodate the storage of any data in a suitable digital format.

A number of program modules can be stored in the drives and RAM 2410, including operating system 2436, one or more applications 2438, other modules (e.g., program modules) 2440 and data 2442 (e.g., program data). All or portions of the operating system, applications, modules, and/or data can also be cached in RAM 2410. The systems and methods described herein can be implemented utilizing various commercially available operating systems or combinations of operating systems.

A device can enter commands and information into computer 2402 through one or more wireless input devices, e.g., keyboard 2428 (which can be wired or wireless) and a pointing device, such as mouse 2430 (which can be wired or wireless). Other input devices (not shown) can include a smart phone, tablet, laptop, wand, wearable device or the like. These and other input devices are often connected to the processing unit 2404 through input device interface 2418 that can be coupled to system bus 2408, but can be connected by other interfaces, such as a parallel port, an IEEE serial port, a game port and/or a universal serial bus (USB) port.

Computer 2402 can operate in a networked environment using logical connections via wired and/or wireless communications to one or more remote computers, such as remote computer(s) 2432. Remote computer(s) 2432 can be a workstation, a server computer, a router, a personal computer, portable computer, microprocessor-based entertainment appliance, a peer device or other common network node, and typically includes many or all of the elements described relative to computer 2402, although, for purposes of brevity, only memory/storage device 2434 is illustrated. The logical connections depicted include wired/wireless connectivity to a local area network (LAN) 2426 and/or larger networks, e.g., WAN 2424, as well as smaller PANs involving a few devices (e.g., at least two). LAN and WAN networking environments are commonplace in the home, offices (e.g., medical facility offices or hospital offices) and companies, and facilitate enterprise-wide computer networks, such as intranets, all of which can connect to a global communications network (e.g., the Internet).

When used in a LAN networking environment, computer 2402 can be connected to local network through a wired and/or wireless communication network interface or network adapter 2420. Network adapter 2420 can facilitate wired or wireless communication to LAN 2426, which can also include a wireless access point (AP) connected to the LAN 2426 for communicating with network adapter 2420.

When used in a WAN networking environment, computer 2402 can include modem 2422 or can be connected to a communications server on WAN 2424 or has other means for establishing communications over WAN 2424, such as by way of the Internet. Modem 2422, which can be internal or external and a wired or wireless device, can be connected to system bus 2408 via input device interface 2416. In a networked environment, program modules depicted relative to computer 2402 or portions thereof, can be stored in a remote memory/storage device. It will be appreciated that the network connections shown are example and other means of establishing a communications link between the computers can be used.

Computer 2402 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 MHz. NFC technology communication is typically over a range not exceeding 0.2 meters (m) and setup time can be less than 0.1 seconds. Low power (e.g., 15 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 24 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, $x=(x1, x2, x3, x4, \ldots, xn)$, to a confidence that the input belongs to a class, that is, $f(x)=$confidence (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predefined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, to optimize space usage or enhance performance of mobile device equipment. A processor can also be implemented as a combination of computing processing units.

Memory disclosed herein can include volatile memory or nonvolatile memory or can include both volatile and non-volatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages or databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the forgoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. A system comprising:
    a comparison device configured to:
        compare first electronic information received at an external device external to a body in which an implantable device is located with second electronic information associated with the implantable device, wherein the first electronic information comprises a first password received via a user interface of the external device and the second electronic information comprises a second password, wherein the first password and the second password represent secure information; and
        determine whether the first password and the second password have a defined level of correlation; and
    a communication device configured to initiate a telemetry session between the external device and the implantable device based on a determination that the first password and the second password have the defined level of correlation.

2. The system of claim 1, wherein the secure information further comprises a visual image of a body in which the implantable device is implanted.

3. The system of claim 1, wherein the external device comprises a mobile device.

4. The system of claim 1, wherein the communication device is configured to forgo pairing the external device and the implantable device based on a determination that the first password and the second password fail to have the defined level of correlation.

5. The system of claim 1, wherein the system further comprises the implantable device which includes the comparison device and the communication device.

6. The system of claim 1, wherein the system further comprises the external device which includes the comparison device and the communication device.

7. The system of claim 1, wherein the system further comprises:
    the external device, wherein the first electronic information is stored on the external device; and
    the implantable device, wherein the second electronic information is stored on the implantable device.

8. The system of claim 1, wherein the system further comprises:
    the external device, wherein the external device is communicatively coupled to a network, and wherein the first electronic information is accessible to the external device via the network.

9. A system comprising:
    a comparison device configured to:
        compare first electronic information received at an external device external to a body in which an implantable device is located with second electronic information associated with the implantable device, wherein the first electronic information comprises first image data associated with the external device, and wherein the second electronic information comprises second image data associated with the implantable device; and
        determine whether the first image data and the second image data have a defined level of correlation; and
    a communication device configured to initiate a telemetry session between the external device and the implantable device based on a determination that the first image data and the second image data have the defined level of correlation.

10. The system of claim 9, wherein the external device comprises a mobile device.

11. The system of claim 9, wherein the communication device is configured to forgo pairing the external device and the implantable device based on a determination that the first image data and the second image data fail to have the defined level of correlation.

12. The system of claim 9, wherein the first image data and the second image data are indicative of one or more electronic images of a patient having the body in which the implantable device is located.

13. The system of claim 9, wherein the external device comprises a camera, and wherein the implantable device is configured to:
  receive the first image data from the external device, wherein the first image data is generated by the camera of the external device.

14. The system of claim 9, wherein the system further comprises:
  the external device, wherein the first electronic information is stored on the external device; and
  the implantable device, wherein the second electronic information is stored on the implantable device.

15. The system of claim 9, wherein the system further comprises:
  the external device, wherein the external device is communicatively coupled to a network, and wherein the first electronic information is accessible to the external device via the network.

16. The system of claim 9, wherein the system further comprises the implantable device which includes the comparison device and the communication device.

17. The system of claim 9, wherein the system further comprises the external device which includes the comparison device and the communication device.

\* \* \* \* \*